United States Patent
Wang et al.

(10) Patent No.: US 11,993,576 B2
(45) Date of Patent: May 28, 2024

(54) N-BENZYL-N-ARYLSULFONAMIDE DERIVATIVE AND PREPARATION AND USE THEREOF

(71) Applicant: Hangzhou Yirui Pharmaceutical Technology Co., Ltd, Zhejiang (CN)

(72) Inventors: Xiaolu Wang, Zhejiang (CN); Yongzhou Hu, Zhejiang (CN); Qing Ye, Zhejiang (CN); Xiuai Hu, Zhejiang (CN)

(73) Assignee: HANGZHOU YIRUI PHARMACEUTICAL TECHNOLOGY CO., LTD, Zhejiang (CN)

( * ) Notice: Subject to any disclaimer, the term of this patent is extended or adjusted under 35 U.S.C. 154(b) by 134 days.

(21) Appl. No.: 17/424,292

(22) PCT Filed: Jan. 21, 2020

(86) PCT No.: PCT/CN2020/073367
§ 371 (c)(1),
(2) Date: Jul. 20, 2021

(87) PCT Pub. No.: WO2020/151687
PCT Pub. Date: Jul. 30, 2020

(65) Prior Publication Data
US 2022/0089555 A1    Mar. 24, 2022

(30) Foreign Application Priority Data
Jan. 22, 2019   (CN) .......................... 201910058021.1

(51) Int. Cl.
*C07D 295/205* (2006.01)
*A61P 17/06* (2006.01)
*C07D 207/14* (2006.01)
*C07D 211/46* (2006.01)
*C07D 211/52* (2006.01)
*C07D 211/54* (2006.01)
*C07D 211/58* (2006.01)
*C07D 211/74* (2006.01)
*C07D 211/88* (2006.01)
*C07D 213/42* (2006.01)
*C07D 231/12* (2006.01)
(Continued)

(52) U.S. Cl.
CPC .......... *C07D 295/205* (2013.01); *A61P 17/06* (2018.01); *C07D 207/14* (2013.01); *C07D 211/46* (2013.01); *C07D 211/52* (2013.01); *C07D 211/54* (2013.01); *C07D 211/58* (2013.01); *C07D 211/74* (2013.01); *C07D 211/88* (2013.01); *C07D 213/42* (2013.01); *C07D 231/12* (2013.01); *C07D 233/36* (2013.01); *C07D 233/64* (2013.01); *C07D 241/08* (2013.01); *C07D 277/28* (2013.01); *C07D 295/155* (2013.01); *C07D 307/52* (2013.01)

(58) Field of Classification Search
None
See application file for complete search history.

(56) References Cited

FOREIGN PATENT DOCUMENTS

| | | |
|---|---|---|
| CN | 101389622 A | 3/2009 |
| CN | 109651297 A | 4/2019 |

(Continued)

OTHER PUBLICATIONS

International Search Report dated May 6, 2020 issued in PCT/CN2020/073367.

(Continued)

*Primary Examiner* — Samantha L Shterengarts
(74) *Attorney, Agent, or Firm* — Scully, Scott, Murphy & Presser, P.C.

(57) ABSTRACT

The invention provides an N-benzyl-N-arylsulfonamide derivative, which is an N-benzyl-N-arylsulfonamide compound represented by formula (I) or a pharmaceutically acceptable salt or solvate thereof. The N-benzyl-N-arylsulfonamide derivative is obtained by condensing a substituted nitrobenzene with 5- or 6-membered nitrogen-containing aliphatic heterocycle (the ring B), reducing the nitro group to an amino group, and subjecting the amino group to reductive amination, sulfonamidation; or by subjecting a substituted nitrobenzene to nitro reduction, reductive amination and sulfonamidation, and condensing the resultant intermediate with 5- or 6-membered nitrogen-containing aliphatic heterocycle (the ring B). It has been experimentally demonstrated that the N-benzyl-N-arylsulfonamide derivative of the invention can specifically bind to Kv1.3 potassium channel and inhibit or decrease its activity, and is useful in the treatment of autoimmune diseases caused by abnormal activation of the Kv1.3 potassium channel in human or animals. The invention further provides a medicament or a pharmaceutical composition comprising the N-benzyl-N-arylsulfonamide derivative.

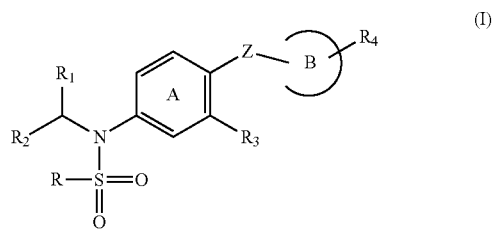

16 Claims, 1 Drawing Sheet

(51) Int. Cl.
*C07D 233/36* (2006.01)
*C07D 233/64* (2006.01)
*C07D 241/08* (2006.01)
*C07D 277/28* (2006.01)
*C07D 295/155* (2006.01)
*C07D 307/52* (2006.01)

(56) References Cited

FOREIGN PATENT DOCUMENTS

| | | |
|---|---|---|
| WO | 2004026823 A1 | 4/2004 |
| WO | 2010/023448 A1 | 3/2010 |
| WO | 2010023445 A1 | 3/2010 |
| WO | 2010130638 A1 | 11/2010 |

OTHER PUBLICATIONS

Database Registry [Online] Chemical Abstracts Service, XP055960884 (Apr. 1, 2018).
Database Registry [Online] Chemical Abstracts Service, XP055960889 (Apr. 6, 2018).
Database Registry [Online] Chemical Abstracts Service, XP055960894 (Apr. 1, 2018).
Database Registry [Online] Chemical Abstracts Service, XP055960898 (Apr. 5, 2018).
Database Registry [Online] Chemical Abstracts Service, XP055960900 (Apr. 4, 2018).
Extended European Search Report dated Sep. 22, 2022 received in European Application No. 20 744 951.3.

N-BENZYL-N-ARYLSULFONAMIDE DERIVATIVE AND PREPARATION AND USE THEREOF

TECHNICAL FIELD

The invention belongs to the field of medicine, and relates to an N-benzyl-N-arylsulfonamide derivative acting as an inhibitor of Kv1.3 potassium channel, as well as use thereof for the treatment of autoimmune diseases mediated by Kv1.3.

BACKGROUND

Kv1.3 (also referred to as KCNA3) potassium channel is an important subclass of voltage-gated potassium channel Kv1 family, and is widely distributed in human tissues including human T lymphocytes. It is involved in various physiological and pathological processes, such as, proliferation, migration and apoptosis of cells, by regulating the concentration of potassium ions [Toldi G. et al. Immunol Res., 2016,64(2):627-631].

Studies on autoimmune diseases have revealed that the voltage-gated potassium channel Kv1.3 on the cell membrane of T lymphocytes plays an important role in many autoimmune diseases [Kazama L. J Physiol Sci., 2015, 65(1):25-35]. In the process of T lymphocyte related immune response, voltage-gated potassium channel Kv1.3 and calcium-activated potassium channel Kca co-regulate membrane potential and $Ca^{2+}$ signal of T lymphocytes, thereby affecting activation, proliferation and cytokine secretion of T lymphocytes, wherein the Kv1.3 potassium channel is relevant to the body's abnormal autoimmunity [Ming Hu et al., Journal of Immunology. 2010, 26 (4): 356-361.]. For instance, in the inflammatory infiltration area of the brain in patients with multiple sclerosis, the expression of Kv1.3 potassium channels on T cells is abnormally increased. It has also been demonstrated that activation of effector memory T lymphocytes ($T_{EM}$) may be accompanied by a significant up-regulation of expression of Kv1.3 potassium channel in autoimmune diseases such as rheumatoid arthritis, psoriasis, contact dermatitis, and type I diabetes, and blockage of Kv1.3 potassium channel may in turn block activation of $T_{EM}$ and reduce corresponding immune damages. Therefore, Kv1.3 potassium channel has been considered as an important target for the treatment of many cell-related autoimmune diseases [Beeton C., PNAS., 2006, 103 (46):17414-17419.] [Koshy et al. J Biol chem 2014, 289 (18): 12623-32].

The voltage-gated channel Kv1.3 is a tetramer composed of 4α subunits. These subunits are assembled into a functional channel, in which a cavity for conducting potassium ions is located in the center of the tetramer. Each of the subunits comprises 6 transmembrane segments (S1-S6), a P ring, and intramembrane N- and C-terminus. Depolarization of cell membrane is sensed by 4 arginines located in the S4 segment, resulting in a conformational change for opening the channel. Known Kv1.3 peptide-based inhibitors all act on entrance to the conducting cavity at the outer membrane, thus inhibiting its potassium ion-conducting function [Chandy and Norton, Curr Opin Chen Biol, 2017, 38: 97-107][Zhao et. al. Toxins (Basel), 2015, 7: 1749-1764].

Kv1.3 is expressed primarily in T lymphocytes and functions together with calcium-activated Kca3.1 potassium channel, to prevent depolarization of cell membrane. When T cells are activated, outflux of potassium ions through these channels emerges, and influx of calcium ions into the cytoplasm through CRAC (Orai/Stim) channels is promoted, to balance out outflow of cations. Eventually, increase of intracytoplasmic calcium ions activates Calcineurin, which results in dephosphorylation of a transcription factor of activated T cells (NFAT) that then translocates into the nucleus, facilitating RNA transcription and producing a series of biological effects of immune activation. Therefore, Kv1.3 and Kca3.1 channels in T cells are part of cell membrane signaling complex, i.e., a cascade coupling extramembrane stimulus signals to the signals within T cells [Chandy and Norton, Curr Opin Chem Biol, 2017, 38:97-107].

It has been reported in the literature that when activated, naive T cells and central memory T cells ($T_{CM}$) up-regulate expression level of Kca3.1 while the level of Kv1.3 is not significantly changed. In contrast, terminally differentiated effector memory T cells ($T_{EM}$) and effector memory T cells expressing CD-45RA ($T_{EMRA}$) in activated state up-regulate expression level of Kv1.3 without affecting expression of Kca3.1. Therefore, selective blockage of Kca3.1 can inhibit proliferation of naive T cells and central memory T cells ($T_{CM}$) and thereby inhibit production of corresponding cytokines. On the other hand, selective blockage of Kv1.3 can inhibit proliferation of effector memory T cells ($T_{EM}$ and $T_{EMRA}$) and production of corresponding cytokines, as well as in vivo migration of T cells, without affecting the function of naive T cells and central memory T cells ($T_{CM}$) protected by Kca3.1 channels [Cahalan and Chandy, Immunol Rev, 2009, 231:59-87] [Wulff et al. J Clin Invest, 2003, 111:1703-1713].

In autoimmune diseases such as multiple sclerosis, rheumatoid arthritis, type I diabetes and psoriasis, autoantigen-specific naive T cells can escape from immune regulations. These cells will be eventually differentiated into $T_{EM}$ and $T_{EMRA}$ cells by repeated stimulations of homologous autoantigens. Therefore, the disease-related autoreactive T cells are primarily $T_{EM}$ and $T_{EMR}$ cells. Depending on the type of cytokines they produce, they can be classified into Th1 and/or Th17 cells among others [Beeton et al. PNAS 2006, 103:17414-17418]. In animal models, selective blockage of Kv1.3 channel or knockout of Kv1.3 gene can prevent and treat a variety of autoimmune diseases without impairing immune responsiveness of naive T cells and central memory T cells ($T_{CM}$) that has protective function. It has been experimentally demonstrated that when Kv1.3 is intact, $T_{EM}$ cells are transformed into effector cells after being activated, while when Kv1.3 is absent, these $T_{EM}$ cells may be transformed into cells having antigen-specific inhibitory effect after be activated. Such flexibility greatly supports targeted therapies based on Kv1.3 channel, i.e., by inhibiting detrimental autoreactive $T_{EM}$ cells and $T_{EMRA}$ cells, while promoting long-term immune tolerance by inducing production of cells having autoantigen-specific inhibitory effect [Chandy and Norton, Curr Opin Chem Biol, 2017, 38:97-107].

In recent years, several Kv1.3-specific peptide-based inhibitors (such as SHK-186 or the like) or small molecule inhibitors (such as PAP-1 or the like) have been reported and used in studies in animal models for the treatment of autoimmune diseases mediated by $T_{EM}$ cells, such as chronic multiple autoimmune encephalomyelitis (EAE), Pristane-induced arthritis, spontaneous autoimmune diabetes, and glomerulonephritis in rats. The results are greatly inspiring. For instance, blockage of Kv1.3 with SHK-186 can resist inductive occurrence of EAE and inhibit production of IFN-γ and IL-17, indicating that blockage of Kv1.3 can be used in the treatment of multiple sclerosis [Gocke et al, J Immunol 2012, 188:5877-5886]. Similarly, in a rat model of asthma induced by ovalbumin, SHK-186 can effectively inhibit proliferation of Th2 $T_{EM}$ cells with highly expressed Kv1.3 and production of cytokines [Valverde et al, J Bone Miner Res 2004, 19:155-164]. In a rat model of autoimmune glomerular basal membrane nephritis, intraperitoneal injection of a small molecule Kv1.3 inhibitor, Psora-4, can significantly decrease proteinuria and crescentic glomeruli, suggesting that Psora-4 plays an important role in the treatment of rapidly developing glomerulonephritis [Hyodo et al, Am J Physical Renal Physiol 2010, 299: F1258-69]. Another small molecule Kv1.3 inhibitor, PAP-1, can effectively inhibit allergic contact dermatitis when applied in a rat topical skin model [Azam et al, J Invest Dermatal 2007, 127(6):1419-1427]. Further, in a SCID mouse psoriasis xenograft model, injection or topical skin application of PAP-1 can reduce thickness of pathological epidermal hyperplasia by approximately 50% and reduce infiltrated $CD3^+$ lymphocytes by 85%, significantly improving psoriasis symptoms [Kun clu-Raychaudhuri et al, J Antoimmun 2014, 55:63-72]. Notably, as recently reported, both SHK-186 (Dalazatide), as a Kv1.3 peptide-based inhibitor, and PAP-1, as a small molecule inhibitor, have been used in Phase I/II clinical trials for the treatment of psoriasis, which demonstrates their safety in humans. Statistical results show that the psoriasis symptoms are improved by a rate as high as more than 90% [Tarch et al, PLoS ONE 2017, 12(7):1-19][Press Relase by Circassia, 13 Aug. 2018].

SUMMARY OF THE INVENTION

One object of the invention is to provide an N-benzyl-N-arylsulfonamide derivative, which is an N-benzyl-N-arylsulfonamide compound represented by formula (I) or a pharmaceutically acceptable salt or solvate thereof,

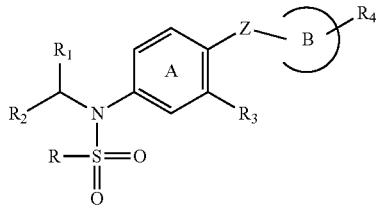

wherein:

ring A is substituted phenyl with the substituent group being selected from the group consisting of

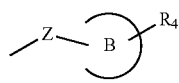

and $R_3$ group; wherein the ring A is preferably the following substituted benzene ring:

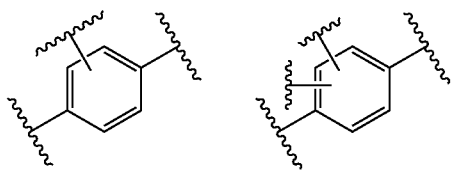

ring B is selected from the group consisting of 5- or 6-membered substituted or unsubstituted aliphatic heterocyclyl containing 1-3 heteroatoms selected from the group consisting of O, N and S, with the substituent group being selected from the group consisting of Z and $R_4$; wherein the ring B is preferably the following 5- or 6-membered aliphatic heterocyclyl containing oxygen and/or nitrogen:

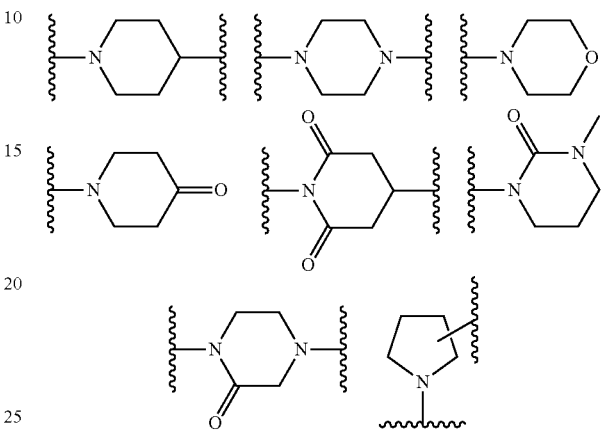

R is selected from the group consisting of substituted or unsubstituted phenyl, or 5- or 6-membered substituted or unsubstituted aromatic heterocyclyl containing 1-2 nitrogen atoms, or C1-6 linear or branched alkyl, or halogenated C1-6 linear or branched alkyl, the substitution of phenyl or aromatic heterocyclyl being mono-, di- or tri-substitution with the substituent group being Ra group;

Ra is optionally selected from the group consisting of H, halogen, nitro, cyano, C1-3 alkyl, C1-3 alkoxy, halogenated C1-3 alkyl and —C—O—C—;

$R_1$ is selected from the group consisting of substituted or unsubstituted phenyl, or 5- or 6-membered substituted or unsubstituted heteroaryl containing 1-3 heteroatoms selected from the group consisting of O, N and S, the substitution being mono-, di- or tri-substitution with the substituent group being Rb group;

Rb is selected from the group consisting of H, halogen, nitro, cyano, C1-3 alkyl, C1-3 alkoxy, halogenated C1-3 alkyl and —C—O—C—;

$R_2$ is selected from the group consisting of C1-3 liner or branched alkyl, cyclopropyl and =O;

$R_3$ is selected from the group consisting of halogen, nitro, cyano, trifluoromethyl, amido, substituted alkylamido;

$R_4$ is selected from the group consisting of H, halogen, =O, OH, $NH_2$, formate group, carbamate group, alkylacyl, acetate group, sulfonamido, pyrrolidonyl, cyclopropyl, aminoformamido, dimethylaminoethoxy, alkanoyloxy, and alkylamido;

Z is selected from the group consisting of O, S and NH, or is absent.

Unless otherwise specified, optionally substituted component as described therein may be substituted at any chemically available position.

The N-benzyl-N-arylsulfonamide derivative of the invention is preferably the following compounds:

ethyl 4-(4-(N-benzylphenylsulfonamido)-2-cyanophenyl) piperazin-1-formate, ethyl 4-(2-cyano-4-((4-fluoro-N-(4-fluorobenzyl)phenyl) sulfonamido) phenyl)piperazin-1-formate, ethyl 4-(2-cyano-4-((4-fluoro-N-(4-fluoro-3-methoxybenzyl)phenyl) sulfonamido)phenyl)piperazin-1-formate,
ethyl 4-(2-cyano-4-(N-(benzenesulfonyl)benzamido)phenyl)piperazin-1-formate,
N-benzyl-N-(3-cyano-4-(4-oxopiperidin-1-yl)phenyl)benzene sulfonamide,
N-benzyl-N-(3-cyano-4-(4-hydroxypiperidin-1-yl)phenyl) benzene sulfonamide,
N-benzyl-N-(3-cyano-4-(4-acetyloxypiperidin-1-yl)phenyl) benzene sulfonamide,
ethyl 4-(2-cyano-4-((4-fluoro-N-propylphenyl)sulfonamido)phenyl) piperazin-1-formate,
ethyl 4-(2-cyano-4-(N-(4-fluorobenzyl)propanesulfonamido)phenyl) piperazin-1-formate,
N-(3-cyano-4-morpholinylphenyl)-N-(4-fluorobenzyl)benzene sulfonamide,
4-(4-(N-benzylbenzenesulfonamido)-2-cyanophenyl)-N,N-dimethyl piperazin-1-formamide,
1-(4-(N-benzylbenzenesulfonamido)-2-cyanophenyl)-N,N-dimethyl piperidin-4-sulfonamide,
ethyl 4-(2-cyano-4-(N-isobutylphenylsulfonamido)phenyl) piperazin-1-formate,
ethyl 1-(4-(N-benzylbenzenesulfonamido)-2-cyanophenyl) piperidin-4-ylcarbamate,
N-(1-(4-(N-benzylbenzenesulfonamido)-2-cyanophenyl) pyrrolidin-3-yl)acetamide,
N-benzyl-N-(3-cyano-4-(2,6-dioxopiperidin-1-yl)phenyl) benzene sulfonamide,
N-benzyl-N-(3-cyano-4-(3-methyl-2-oxotetrahydropyrimidin-1(2H)-yl)phenyl)benzenesulfonamide,
N-benzyl-N-(3-cyano-4-(4-(2-(dimethylamino)ethoxy)piperidin-1-yl) phenyl)benzenesulfonamide,
N-(3-cyano-4-(4-hydorxypiperidin-1-yl)phenyl)-N-(4-fluorobenzyl) propane-1-sulfonamide,
N-(3-cyano-4-(4-hydorxypiperidin-1-yl)phenyl)-N-(4-fluorobenzyl) benzenesulfonamide,
4-(2-cyano-4-(N-(4-fluorobenzyl)propyl)phenyl)-N,N-dimethyl piperazin-1-formamide,
ethyl 4-(4-(N-benzylpropanesulfonamido)2-cyanophenyl) piperazin-1-formate,
ethyl 4-(2-cyano-4-(N-(3-fluorobenzyl)propanesulfonamido)phenyl) piperazin-1-formate,
ethyl 4-(4-(4-(N-(4-chlorobenzyl)propanesulfonamido)2-cyanophenyl) piperazin-1-formate,
ethyl 4-(2-cyano-4-(N-(2-fluorobenzyl)propanesulfonamido)phenyl) piperazin-1-formate,
ethyl 4-(2-cyano-4-(N-(3-methoxybenzyl)propanesulfonamido)phenyl) piperazin-1-formate,
ethyl 4-(2-cyano-4-(N-(4-methoxybenzyl)propanesulfonamido)phenyl) piperazin-1-formate,
ethyl 4-(2-cyano-4-(N-(3,4-dimethoxybenzyl)propanesulfonamido) phenyl) piperazin-1-formate,
ethyl 4-(2-cyano-4-(N-(2-fluoro-4-methoxybenzyl) propanesulfonamido)phenyl)piperazin-1-formate,
ethyl 4-(2-cyano-4-(N-(4-fluoro-2-methoxybenzyl) propanesulfonamido)phenyl)piperazin-1-formate,
ethyl 4-(2-cyano-4-(N-(pyrimidin-4-ylmethyl)propanesulfonamido) phenyl)piperazin-1-formate,
ethyl 4-(2-cyano-4-(N-(pyridin-2-ylmethyl)propanesulfonamido) phenyl)piperazin-1-formate,
ethyl 4-(2-cyano-4-(N-(furan-2-ylmethyl)propanesulfonamido)phenyl) piperazin-1-formate,
ethyl 4-(2-cyano-4-(N-(thiazol-4-ylmethyl)propanesulfonamido) phenyl) piperazin-1-formate,
ethyl 4-(2-cyano-4-(N-((1-methyl-1H-imidazol-5-yl) methyl) propanesulfonamido)phenyl)piperazin-1-formate,
ethyl 4-(2-cyano-4-(N-((1-methyl-1H-pyrazol-5-yl)methyl) propanesulfonamido)phenyl)piperazin-1-formate,
4-(2-cyano-4-((N-(4-fluorobenzyl)-2-methylpropyl)sulfonamido) phenyl)-N,N-dimethylpiperazin-1-formamide,
4-(2-cyano-4-(N-(4-fluorobenzyl)butanesulfonamido)phenyl)-N,N-dimethylpiperazin-1-formamide,
4-(2-cyano-4-((N-(4-fluorobenzyl)-3-methylbutyl)sulfonamido)phenyl)-N,N-dimethylpiperazin-1-formamide,
4-(2-cyano-4-((N-(4-fluorobenzyl)-2,2-dimethylpropyl) sulfonamido) phenyl)-N,N-dimethylpiperazin-1-formamide,
4-(2-cyano-4-(N-(pyridin-4-ylmethyl)propanesulfonamido) phenyl)-N, N-dimethylpiperazin-1-formamide,
4-(2-cyano-4-(N-(pyrimidin-4-ylmethyl)propanesulfonamido)phenyl)-N,N-dimethylpiperazin-1-formamide,
4-(2-cyano-4-(N-(4-fluorobenzyl)ethanesulfonamido)phenyl)-N,N-dimethylpiperazin-1-sulfonamide,
4-(4-(N-(4-chlorobenzyl)propanesulfonamido)-2-cyanophenyl)-N,N-dimethylpiperazin-1-sulfonamide,
4-(2-cyano-4-(N-(4-methoxybenzyl)propanesulfonamido) phenyl)-N,N-dimethylpiperazin-1-sulfonamide,
4-(2-cyano-4-((4-fluoro-N-((1-methyl-1H-pyrazol-5-yl) methyl)phenyl) sulfonamido)phenyl)-N,N-dimethylpiperazin-1-sulfonamide,
4-(2-cyano-4-((1-cyclopropyl-N-(2,4-difluorobenzyl) methyl) sulfonamido)phenyl)-N,N-dimethylpiperazin-1-sulfonamide,
4-(2-cyano-4-(—N-(4-fluorophenyl)pyridin-3-sulfonamido) phenyl)-N, N-dimethylpiperazin-1-sulfonamide,
ethyl 4-(4-(N-(4-fluorophenyl)propanesulfonamido)-2-(trifluoro methyl)phenyl)piperazin-1-formate,
ethyl 4-(2-cyano-4-((4-fluoro-N-(4-fluorobenzyl)phenyl) sulfonamido) phenyl)piperazin-1-formate,
N-(3-cyano-4-(piperidin-4-ylthio)phenyl)-N-(4-fluorobenzyl)propane sulfonamide,
N-(3-cyano-4-(piperidin-4-ylamino)phenyl)-N-(4-fluorobenzyl) propanesulfonamide,
N-(4-((1-acetylpiperidin-4-yl)oxy)-3-cyanophenyl)-N-(4-fluorobenzyl) propanesulfonamide,
N-(4-((1-acetylpiperidin-4-yl)thio)-3-cyanophenyl)-N-(4-fluorobenzyl) propanesulfonamide,
N-(4-((1-acetylpiperidin-4-yl)amino)-3-cyanophenyl)-N-(4-fluoro benzyl) propanesulfonamide,
N-(4-((1-formylpiperidin-4-yl)oxy)-3-cyanophenyl)-N-(4-fluoro benzyl) propanesulfonamide,
N-(4-((1-formylpiperidin-4-yl)thio)-3-cyanophenyl)-N-(4-fluoro benzyl) propanesulfonamide,
N-(4-((1-acetylpiperidin-4-yl)oxy)-3-cyanophenyl)-N-benzylbenzene sulfonamide,
N-(4-((1-formylpiperidin-4-yl)oxy)-3-cyanophenyl)-N-benzylbenzene sulfonamide,
N-(4-((1-formylpiperidin-4-yl)amino)-3-cyanophenyl)-N-(4-fluoro benzyl)propanesulfonamide,
and pharmaceutically acceptable salts or solvates thereof.

Another object of the invention is to provide a method for preparing the compound having formula (I). The method is embodied by the following steps:

1. If the ring A is a substituted benzene ring, and Z is absent in the compound of formula (I):

condensing 1-halo-2-$R_3$-4-nitrobenzene with 5- or 6-membered nitrogen-containing aliphatic heterocycle (the ring B) under a basic condition, reducing the nitro group to an amino group, and subjecting the amino group to reductive amination, sulfonamidation, and deprotection if necessary, to give the target compound;

alternatively, subjecting 1-halo-2-$R_3$-4-nitrobenzene to nitro reduction, reductive amination and sulfonamidation, condensing the resultant intermediate with 5- or 6-membered nitrogen-containing aliphatic heterocycle (the ring B) under a basic condition, and deprotecting the resultant condensate if necessary, to give the target compound.

The expression of "if necessary" as recited in "deprotection/deprotecting if necessary" refers to a situation in which a protecting group is present.

Compounds 1-49 and 61 are prepared according to the following synthesis scheme:

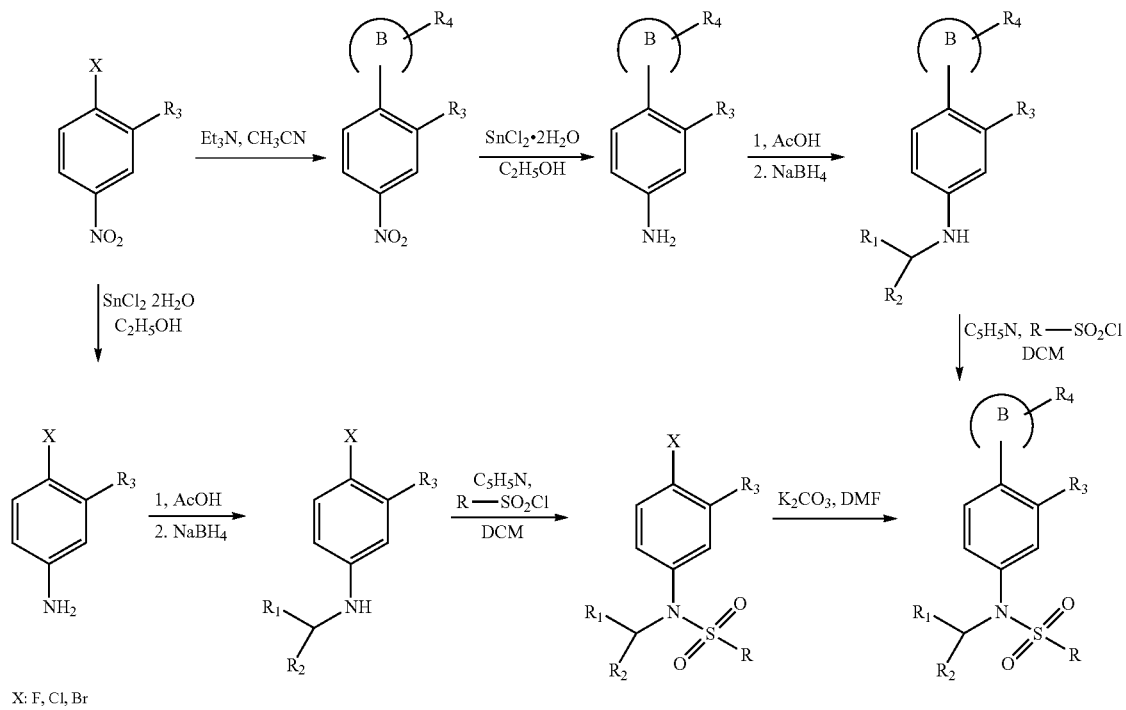

2. If the ring A is a benzene ring, the ring B is piperidine, and Z is selected from the group consisting of O, S and NH in the compound of formula (I):

reacting 1-halo-2-$R_3$-4-nitrobenzene with 4-hydroxy-, 4-mercapto- or 4-amino-piperidine under a basic condition, reducing the nitro group to an amino group, and subjecting the amino group to reductive amination and sulfonamidation, to give the target compound;

alternatively, reacting N-benzyl/alkyl-N-(3-$R_3$-4-fluro-phenyl)sulfonamide with N-Boc protected 4-hydroxy-, 4-mercapto- or 4-amino-piperidine, removing the Boc protecting group, and substituting at N-position of piperidine, to give the target compound.

Compounds 50-60 are prepared according to the following synthesis scheme:

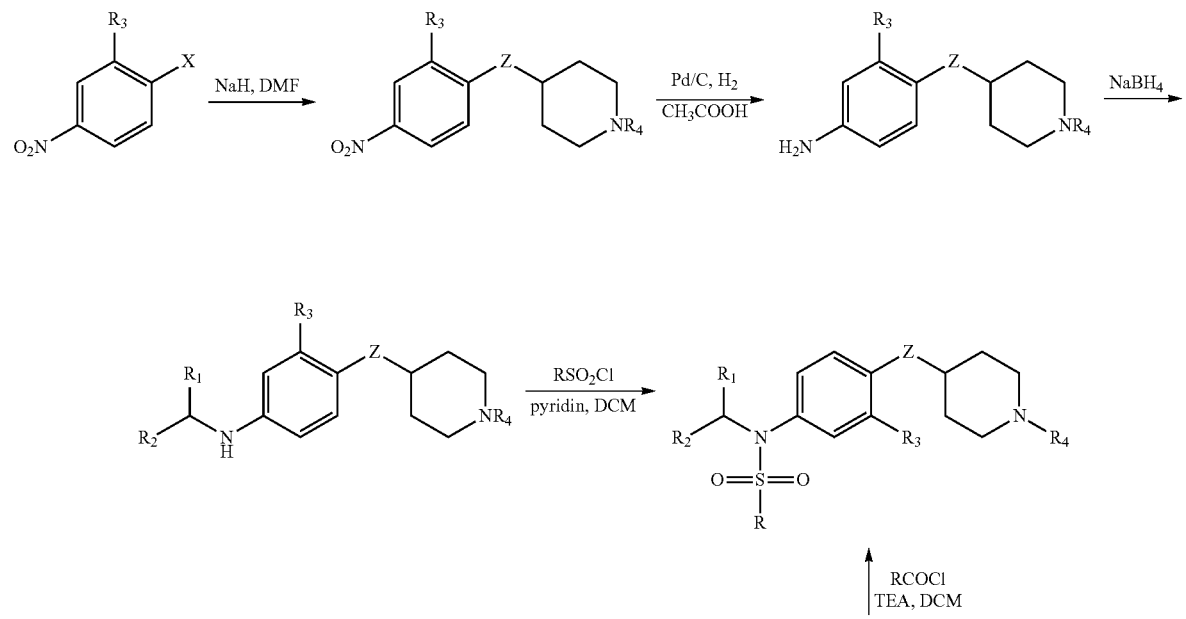

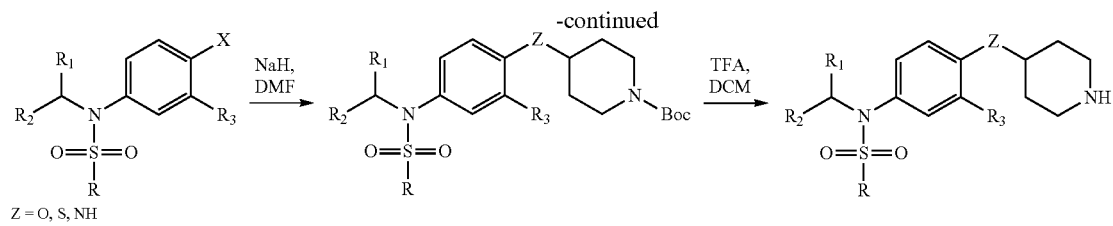

Z = O, S, NH

A further object of the invention is to provide use of N-benzyl-N-arylsulfonamide derivative in preparation of a medicament for treating autoimmune diseases. The autoimmune diseases are those medicated by Kv1.3. The N-benzyl-N-arylsulfonamide derivative provided in the invention can specifically bind to potassium channel Kv1.3, and inhibit or reduce its activity, and thus is useful as a selective inhibitor of Kv1.3 potassium channel for the treatment of autoimmune diseases.

The medicament for treating autoimmune diseases comprises at least one active component and one or more pharmaceutically acceptable carriers or excipients, wherein the active component is any one or more of N-benzyl-N-arylsulfonamide compounds of formula (I), pharmaceutically acceptable salts or solvates thereof.

The carrier or excipient comprises a diluent, filler, adhesive, wetting agent, disintegrating agent, absorption accelerator, surfactant, adsorption carrier, lubricant or the like conventionally used in the field of pharmacy. If necessary, a flavor agent, a sweetener or the like can also be added. The medicament of the invention can be formulated into various forms such as tablet, capsule, patch, emulsion, suspension, gel, powder, granule, oral liquid, injection and the like. The medicament in each of the dosage forms mentioned above can be prepared according to conventional methods in the field of pharmacy.

The salt of N-benzyl-N-arylsulfonamide compound of the invention can be prepared by a method well known to the skilled person in the art. The salt can be an inorganic acid salt, an organic acid salt, or the like. The inorganic acid salt include salts formed with hydrohalogen acid (such as hydrofluoric acid, hydrobromic acid, hydriodic acid, hydrochloric acid), nitric acid, carbonic acid, sulfuric acid, phosphoric acid, and the like. The organic acid salt include salts formed with malic acid, L-malic acid, D-malic acid, citric acid, fumaric acid, oxalic acid, lactic acid, camphor sulfonic acid, L-camphor sulfonic acid, D-camphor sulfonic acid, p-toluene sulfonic acid, methane sulfonic acid, benzoic acid and the like.

The invention further provides use of any of the compounds of formula (I) and pharmaceutically acceptable salts or solvates thereof alone or in combination with other drugs in preparation of a medicament for treating autoimmune diseases.

The invention further provides a medicament for treating autoimmune diseases, comprising any of the N-benzyl-N-arylsulfonamide compounds of formula (I) or pharmaceutically acceptable salts or solvates thereof as an active component.

The invention further provides a method for treating autoimmune diseases by administering to a patient in need of treatment of autoimmune diseases an effective amount of the N-benzyl-N-arylsulfonamide compound of formula (I) or a pharmaceutically acceptable salt or solvate thereof.

Kv1.3 potassium channel has been considered as an important target for the treatment of cell autoimmune diseases. Therefore, a selective inhibitor of Kv1.3 potassium channel is useful in the treatment of autoimmune diseases. The autoimmune diseases include psoriasis, psoriatic arthritis, allergic and irritant contact dermatitis, atopic dermatitis, vitiligo, rheumatoid arthritis, type I diabetes, multiple sclerosis, asthma, glomerulonephritis, periodontal disease, pars planitis, graft rejection, neural degeneration, obesity, hypertension.

It has been experimentally verified that the N-benzyl-N-arylsulfonamide derivative of the invention may selectively inhibit activity of Kv1.3 potassium channel, and is useful in the treatment of autoimmune diseases caused by abnormal activation of the Kv1.3 potassium channel in human or animals. The invention further provides a medicament or a pharmaceutical composition comprising such compounds.

DETAILED DESCRIPTION

Figure 1:
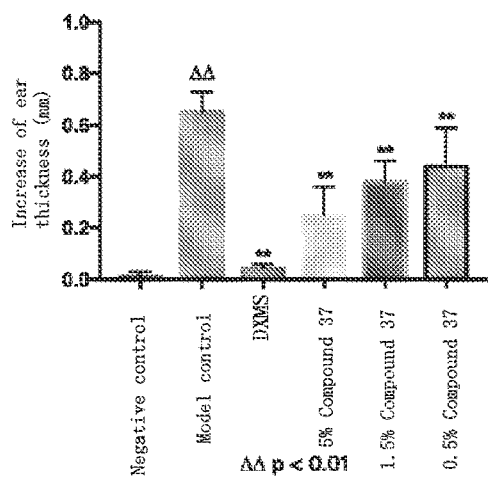
FIG. 1 is a graph showing the effect of compound 37 on a rat model of atopic dermatitis (ACD). Compound 37 significantly reduced ear inflammation in rats with atopic dermatitis (ACD) in a manifest dose-dependent manner.

The invention is further described with reference to examples. The following examples are merely illustrative of the invention, and not by way of limitation.

Preparation Example 1: Synthesis of ethyl 4-(4-(N-benzylphenyl sulfonamido)-2-cyanophenyl)piperazin-1-formate (Compound 1)

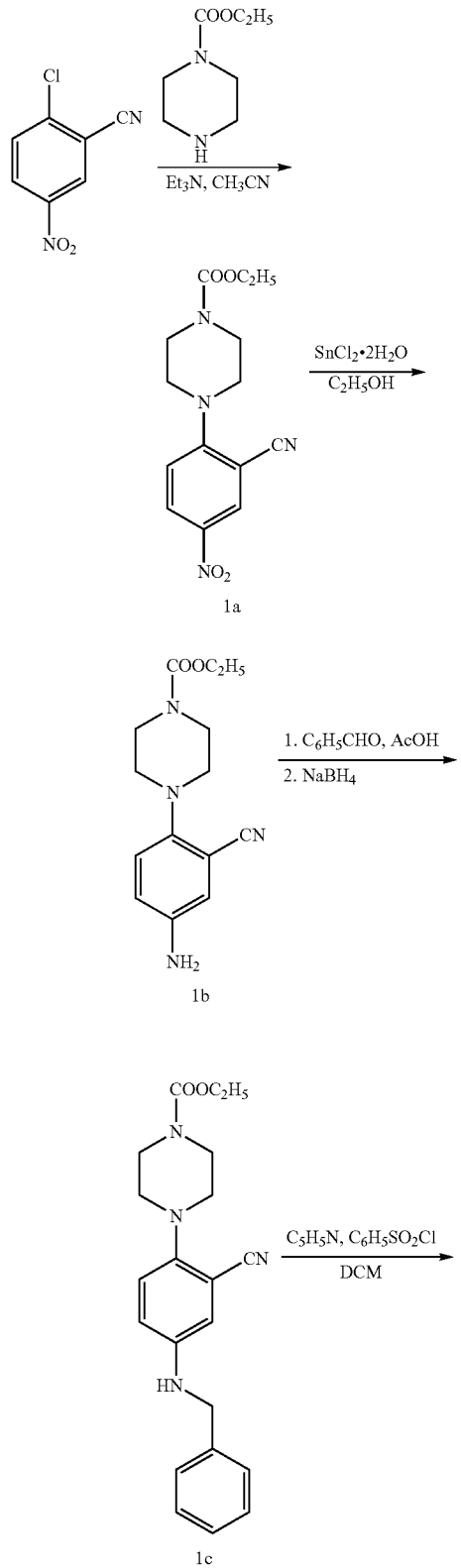

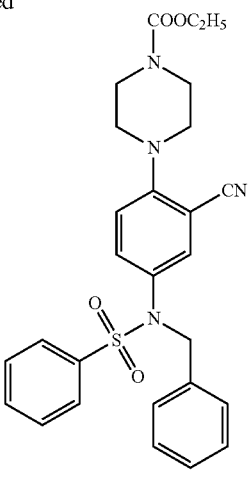

Step 1. Synthesis of ethyl 4-(2-cyano-4-nitrophenyl)piperazin-1-formate (Intermediate 1a)

To a reaction flask, 2-chloro-5-nitrobenzonitrile (0.91 g, 5.0 mmol), ethyl piperzin-1-formate (0.84 g, 5.3 mmol), triethylamine (1.1 g, 10.9 mmol) and 20 mL of acetonitrile were added, and allowed for reaction under reflux for 4.5 h. After completion of the reaction, the reaction mixture was cooled to room temperature, diluted with water, and extracted with ethyl acetate. The organic layer was dried over anhydrous sodium sulfate, filtered and concentrated. The residue was recrystallized with ethyl acetate to give 1a, with a yield of 71.7%; ESI-MS: m/z=305[M+1]$^+$.

Step 2. Synthesis of ethyl 4-(4-amino-2-cyanophenyl)piperazin-1-formate (Intermediate 1b)

To a reaction flask, 1a (2.76 g, 9.0 mmol), stannous chloride dihydrate (11.12 g, 49.3 mmol) and 130 mL of anhydrous ethanol were added, and allowed for reaction under reflux for 2 h. After completion of the reaction, the reaction mixture was cooled to room temperature, alkalized with a sodium carbonate solution, and suction-filtered. The filtrate was extracted with ethyl acetate. The organic layer was dried over anhydrous sodium sulfate, filtered and concentrated. The residue was recrystallized with ethyl acetate to give 1b, with a yield of 71.3%; ESI-MS: m/z=275 [M+1]$^+$.

Step 3. Synthesis of ethyl 4-(4-benzylamino-2-cyanophenyl)piperazin-1-formate (1c)

1b (0.27 g, 1.0 mmol) was dissolved in 1 mL of acetic acid, to which benzaldehyde (0.14 g, 1.3 mmol) was added, followed by stirring at room temperature for 1 h. The reaction mixture was cooled to 10-15° C., to which sodium borohydride (0.04 g, 1.1 mmol) was added, and allowed for reaction for 10 min with the temperature maintained. Thereafter, the reaction mixture was alkalized with a sodium carbonate solution, and extracted with ethyl acetate. The organic layer was dried over anhydrous sodium sulfate, filtered and concentrated. The residue was recrystallized with ethyl acetate to give 1e, with a yield of 86.0%; ESI-MS: m/z=365[M+1]$^+$.

Step 4. Synthesis of ethyl 4-(4-(N-benzylbenzene-sulfonamido)-2-cyanophenyl)piperazin-1-formate (Compound 1)

1e (0.31 g, 0.86 mmol) was dissolved in 3.0 mL of dichloromethane, to which pyridine (0.37 g, 4.7 mmol) and benzene sulfonyl chloride (0.18 g, 1.0 mmol) were added, followed by stirring at room temperature for 5 h. The reaction mixture was acidified with diluted HCl, and extracted with dichloromethane. The organic layer was dried over anhydrous sodium sulfate, filtered and concentrated. The residue was recrystallized with ethyl acetate to give 1, with a yield of 77.4%; $^1$H NMR (500 MHz, Chloroform-d): δ 7.71-7.63 (m, 3H), 7.56 (t, J=7.8 Hz, 2H), 7.27-7.23 (m, 3H), 7.22-7.19 (m, 2H), 7.16 (dd, J=7.9, 2.6 Hz, 1H), 7.09 (d, J=2.6 Hz, 1H), 6.81 (d, J=7.9 Hz, 1H), 4.68 (s, 2H), 4.18 (q, J=7.1 Hz, 2H), 3.70-3.62 (m, 4H), 3.18-3.10 (m, 4H), 1.29 (t, J=7.0 Hz, 3H); ESI-MS: m/z=505 [M+1]$^+$.

Preparation Example 2. Synthesis of ethyl 4-(2-cyano-4-((4-fluoro-N-(4-fluorobenzyl)phenyl)sulfo-namido)phenyl)piperazin-1-formate (Compound 2)

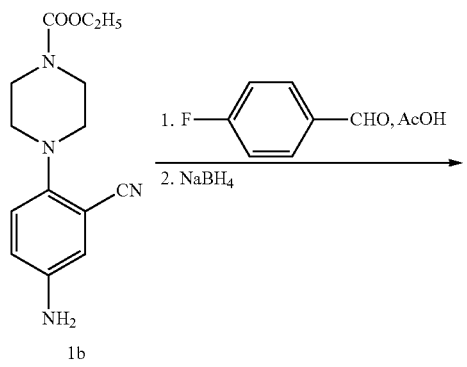

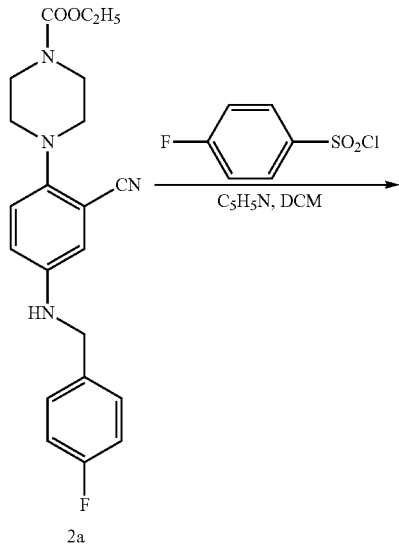

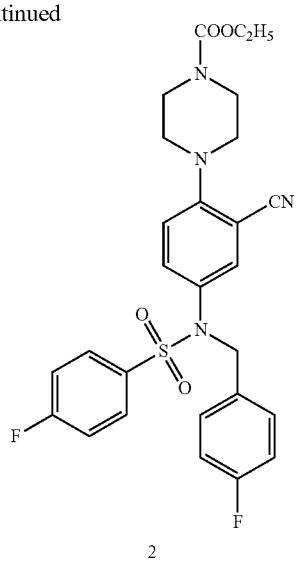

Step 1. Synthesis of ethyl 4-(2-cyano-4-((4-fluo-robenzyl)amino) phenyl)piperazin-1-formate (2a)

The synthesis was accomplished with reference to Step 3 of Example 1, except that an intermediate 1b and p-fluo-robenzaldehyde were used as raw materials to prepare compound 2a; ESI-MS: m/z=384[M+1]$^+$.

Step 2. Synthesis of ethyl 4-(2-cyano-4-((4-fluoro-N-(4-fluorobenzyl) phenyl)sulfonamido)phenyl) piperazin-1-formate (Compound 2)

The synthesis was accomplished with reference to Step 4 of Example 1, except that 2a and p-fluorobenzene sulfonyl chloride were used as raw materials to prepare compound 2, with a yield of 50.2%. $^1$H NMR (500 MHz, Chloroform-d): δ 7.72-7.65 (m, 2H), 7.22 (t, J=8.5 Hz, 2H), 7.19-7.16 (m, 2H), 7.12-7.10 (m, 2H), 6.95 (t, J=8.6 Hz, 2H), 6.83 (d, J=9.6 Hz, 1H), 4.63 (s, 2H), 4.17 (q, J=7.1 Hz, 2H), 3.70-3.60 (m, 4H), 3.20-3.11 (m, 4H), 1.28 (t, J=7.1 Hz, 3H); ESI-MS: m/z=541[M+1]$^+$.

Preparation Example 3. Synthesis of ethyl 4-(2-cyano-4-((4-fluoro-N-(4-fluoro-3-methoxybenzyl) phenyl)sulfonamido)phenyl)piperazin-1-formate (compound 3)

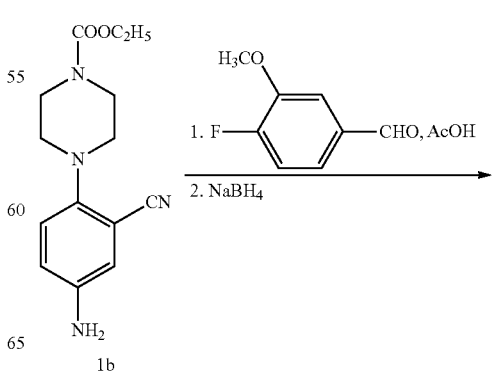

-continued

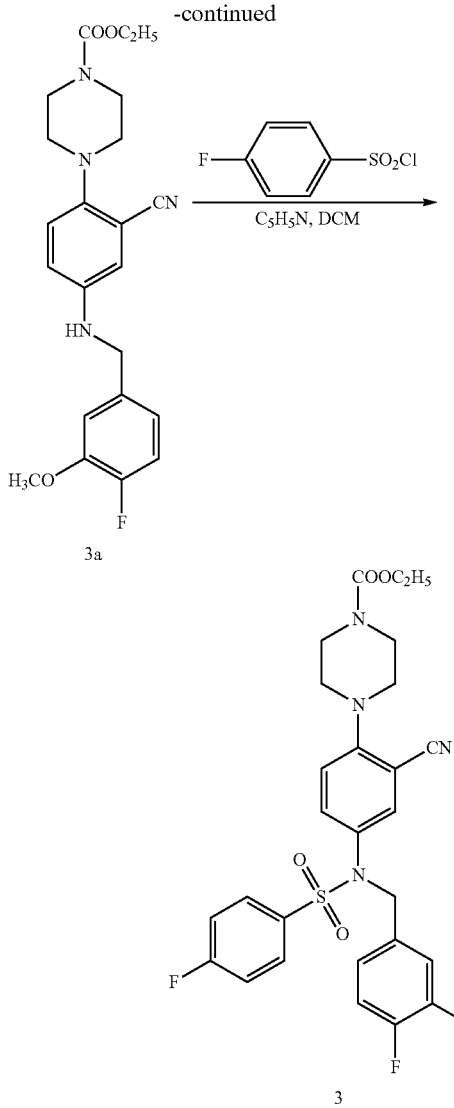

(s, 1H), 4.53 (s, 2H), 4.14 (q, J=7.2 Hz, 2H), 3.83 (s, 3H), 3.32-3.29 (m, 8H), 1.22 (t, J=7.2 Hz, 3H); ESI-MS: m/z=571 [M+1]⁺.

Preparation Example 4. Synthesis of ethyl 4-(2-cyano-4-(N-(benzene sulfonamido)benzamido)phenyl)piperazin-1-formate (Compound 4)

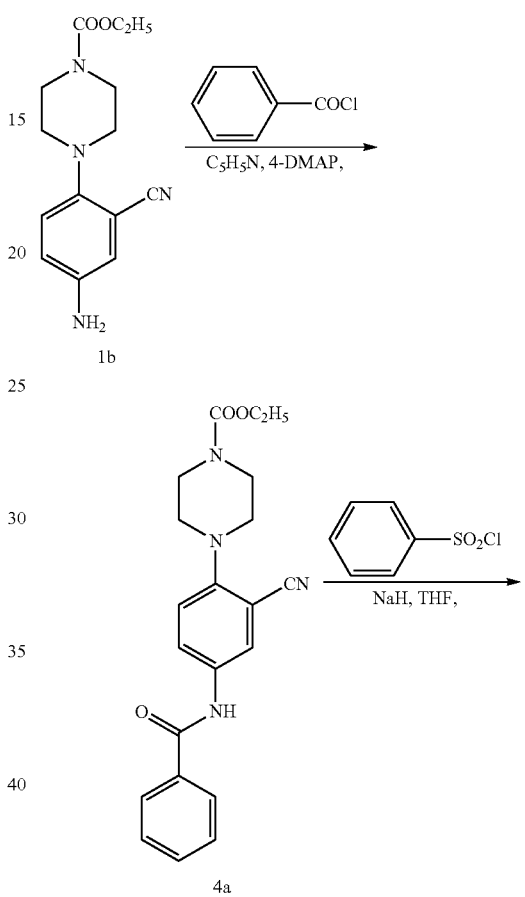

Step 1. Synthesis of ethyl 4-(2-cyano-4-((4-fluoro-3-methoxybenzyl) amino)phenyl)piperazin-1-formate (3a)

The synthesis was accomplished with reference to Step 3 of Example 1, except that an intermediate 1b and 4-fluoro-3-methoxy benzaldehyde were used as raw materials to prepare compound 3a, with a yield of 73.0%; ESI-MS: m/z=413[M+1]⁺.

Step 2. Synthesis of ethyl 4-(2-cyano-4-((4-fluoro-N-(4-fluoro-3-methoxybenzyl)phenyl)sulfonamino) phenyl)piperazin-1-formate (Compound 3)

The synthesis was accomplished with reference to Step 4 of Example 1, except that 3a and p-fluorobenzene sulfonyl chloride were used as raw materials to prepare compound 3, with a yield of 53.2%. ¹H NMR (500 MHz, Chloroform-d): δ 7.98 (m, 2H), 7.40 (dd, J=8.0, 7.5 Hz, 2H), 7.23 (dd, J=8.0, 7.5 Hz, 1H), 7.06 (d, J=7.5 Hz, 1H), 6.95 (dd, J=5.0, 1.5 Hz, 1H), 6.81 (d, J=7.5H, 1H), 6.77 (dd, J=7.5, 1.5 Hz, 1H), 6.74

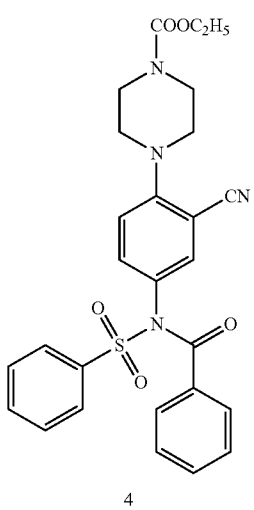

Step 1. Synthesis of ethyl 4-(4-benzamido-2-cyanophenyl)piperazin-1-formate (4a)

1b (0.5 g, 1.82 mmol) and 4-DMAP (0.025 g, 0.2 mmol) were dissolved in 3.0 mL of pyridine, to which benzoyl chloride (0.31 g, 2.19 mmol) was added, followed by stirring at room temperature for 2 h. The reaction mixture was acidified with diluted HCl, extracted with ethyl acetate, washed with saturated saline, dried over anhydrous sodium sulfate, filtered, and concentrated under reduced pressure. The residue was purified with silica gel column chromatography (PE:EA=2:1, v/v), to give compound 4a, with a yield of 88.0%; ESI-MS: m/z=379[M+1]$^+$.

Step 2. Synthesis of ethyl 4-(2-cyano-4-(N-(benzenesulfonamido) benzamido)phenyl)piperazin-1-formate (Compound 4)

4a (0.3 g, 0.79 mmol) was dissolved in 15 mL of anhydrous THF. The resultant mixture was cooled to 0° C., to which 60% sodium hydride (0.034 g, 0.85 mmol) was added and allowed for reaction for 0.5 h with the temperature maintained, and then benzene sulfonyl chloride (0.14 g, 0.79 mmol) was added thereto. Then the resultant mixture was warmed to room temperature and allowed for reaction for 2 h. The resultant reaction mixture was filtered, and the filtrate was concentrated under reduced pressure. The residue was purified with silica gel column chromatography (PE:EA=1:2, v/v), to give 4, with a yield of 61.0%. $^1$H NMR (500 MHz, Chloroform-d): δ 7.97-7.94 (m, 2H), 7.70 (t, J=7.5 Hz, 1H), 7.61-7.55 (m, 2H), 7.47-7.42 (m, 2H), 7.37 (t, J=7.5 Hz, 1H), 7.34 (dd, J=7.8, 2.6 Hz, 1H), 7.29-7.27 (m, 1H), 7.25-7.22 (m, 2H), 6.89 (d, J=7.8 Hz, 1H), 4.18 (q, J=7.1 Hz, 2H), 3.70-3.65 (m, 4H), 3.25-3.17 (m, 4H), 1.29 (t, J=7.1 Hz, 3H); ESI-MS: m/z=519[M+1]$^+$.

Preparation Example 5. Synthesis of N-benzyl-N-(3-cyano-4-(4-oxopiperazin-1-yl)phenyl)benzenesulfonamide (Compound 5)

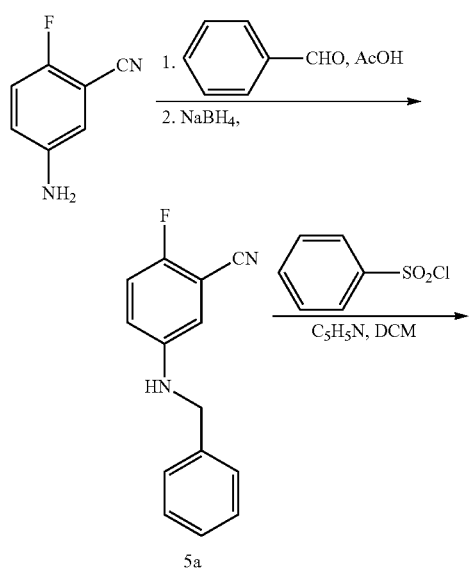

5a

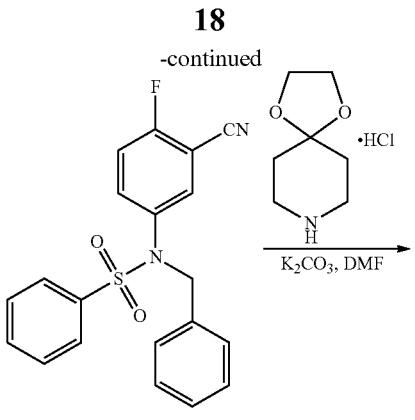

5b

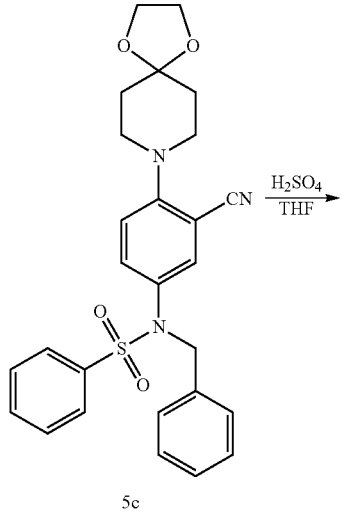

5c

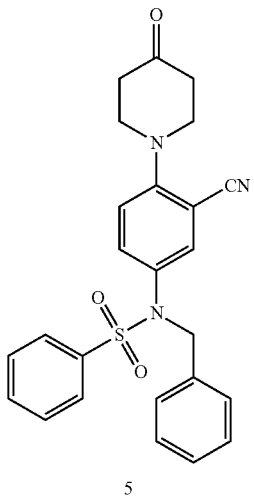 [SMILES: N#Cc1cc(N(Cc2ccccc2)S(=O)(=O)c2ccccc2)ccc1N1CCC(=O)CC1]

5

Step 1. Synthesis of 5-(benzylamino-2-fuorobenzonitrile (5a)

5-Amino-2-flurobenzonitrile (1.50 g, 11.0 mmol) was dissolved in 10 mL of acetic acid, to which benzaldehyde (1.50 g, 14.1 mmol) was added, followed by stirring at room temperature for 1 h. Thereafter, the reaction mixture was cooled to 10-15° C., to which sodium borohydride (0.44 g, 11.6 mmol) was added, followed by stirring for another 10 min with the temperature maintained. Then, the reaction mixture was alkalized with a sodium carbonate solution, and extracted with ethyl acetate. The organic layer was dried over anhydrous sodium sulfate, filtered and concentrated under vacuum. The residue was recrystallized with ethyl acetate to give 5a, with a yield of 80.2%; ESI-MS: m/z=227 [M+1]$^+$.

Step 2. Synthesis of N-benzyl-N-(3-cyano-4-fluorophenyl) benzenesulfonamide (5b)

5a (1.54 g, 6.8 mmol) was dissolved in 20 mL of dichloromethane, to which pyridine (2.96 g, 37.4 mmol) and benzene sulfonyl chloride (1.44 g, 8.2 mmol) were added, followed by stirring at room temperature for 5 h. The reaction mixture was acidified with diluted HCl, extracted with dichloromethane, washed with saturated saline, dried over anhydrous sodium sulfate, filtered, and concentrated under reduced pressure. The residue was recrystallized with ethyl acetate to give 5b, with a yield of 87.8%; ESI-MS: m/z=337[M+1]$^+$.

Step 3. Synthesis of N-benzyl-N-(3-cyano-4-(1,4-dioxa-8-azaspiro [4.5]dec-8-yl)phenyl)benzenesulfonamide (5c)

To a reaction flask, 5b (0.20 g, 0.55 mmol), 4-piperidone ethylene glycol ketal hydrochloride (0.11 g, 0.62 mmol), anhydrous potassium carbonate (0.22 g, 1.61 mmol) and 2 mL of DMSO were added, and allowed for reaction at 120° C. for 6 h. After completion of the reaction, the resultant mixture was cooled to room temperature, diluted with water, extracted with ethyl acetate, and washed with saturated saline. The organic layer was dried over anhydrous sodium sulfate, filtered and concentrated under reduced pressure. The residue was purified with silica gel column chromatography (PE:EA=2:1, v/v) to give 5c, with a yield of 86.7%; ESI-MS: m/z=490[M+1]$^+$.

Step 4. Synthesis of N-benzyl-N-(3-cyano-4-(4-oxopiperidin-1-yl)phenyl) benzenesulfonamide (Compound 5)

5c (0.20 g, 0.41 mmol) was dissolved in 3 mL of THF, to which 3 mL of 10% diluted sulfuric acid solution was added, followed by stirring at room temperature for 5 h. The reaction mixture was alkalinized with a sodium carbonate solution, extracted with ethyl acetate, washed with saturated saline, dried over anhydrous sodium sulfate, filtered, and concentrated under reduced pressure. The residue was purified with silica gel column chromatography (PE:EA=1:1, v/v) to give 50, with a yield of 87.9%. $^1$H NMR (500 MHz, Chloroform-d): δ 7.71-7.65 (m, 3H), 7.57 (t, J=7.5 Hz, 2H), 7.25-7.23 (m, 3H), 7.22-7.20 (m, 2H), 7.18 (dd, J=7.8, 2.6 Hz, 1H), 7.12 (d, J=2.6 Hz, 1H), 6.87 (d, J=7.8 Hz, 1H), 4.69 (s, 2H), 3.50 (t, J=6.0 Hz, 4H), 2.66 (t, J=6.0 Hz, 4H); ESI-MS: m/z=446[M+1]$^+$.

Preparation Example 6. Synthesis of N-benzyl-N-(3-cyano-4-(4-hydroxypiperidin-1-yl)phenyl)benzenesulfonamide (Compound 6)

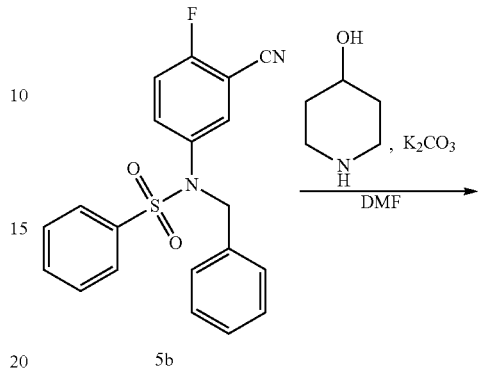

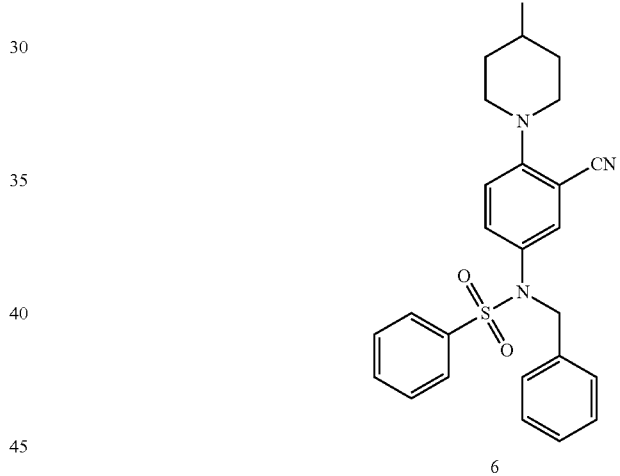

Steps: 5b (0.50 g, 1.36 mol), 4-piperidinol (1.58 g, 1.56 mmol) and potassium carbonate (0.54 g, 3.9 mmol) were dissolved in 5 mL of DMF, warmed to 100° C., and allowed for reaction for 2 h. After completion of the reaction, the reaction mixture was cooled to room temperature, diluted with water, extracted with ethyl acetate, washed with saturated saline, dried over anhydrous sodium sulfate, filtered, and concentrated under reduced pressure. The residue was purified with silica gel column chromatography (DCM:EA=10:1, v/v) to give 6, with a yield of 70.4%. $^1$H NMR (500 MHz, Chloroform-d): δ 7.71-7.63 (m, 3H), 7.55 (t, J=7.5 Hz, 2H), 7.25 (m, 1H), 7.24-7.21 (m, 2H), 7.20-7.18 (m, 2H), 7.12 (dd, J=7.9, 2.6 Hz, 1H), 7.04 (d, J=2.6 Hz, 1H), 6.82 (d, J=7.9 Hz, 1H), 4.67 (s, 2H), 4.03-3.84 (m, 1H), 3.52-3.40 (m, 2H), 3.09-2.93 (m, 2H), 2.15-1.97 (m, 2H), 1.84-1.67 (m, 2H); ESI-MS: m/z=448[M+1]$^+$.

Preparation Example 7. Synthesis of N-benzyl-N-(3-cyano-4-(4-acetyloxypiperidin-1-yl)phenyl)benzenesulfonamide (Compound 7)

Preparation Example 8. Ethyl 4-(2-cyano-4-((4-fluoro-N-propylphenyl) sulfonamido)phenyl)piperazin-1-formate (Compound 8)

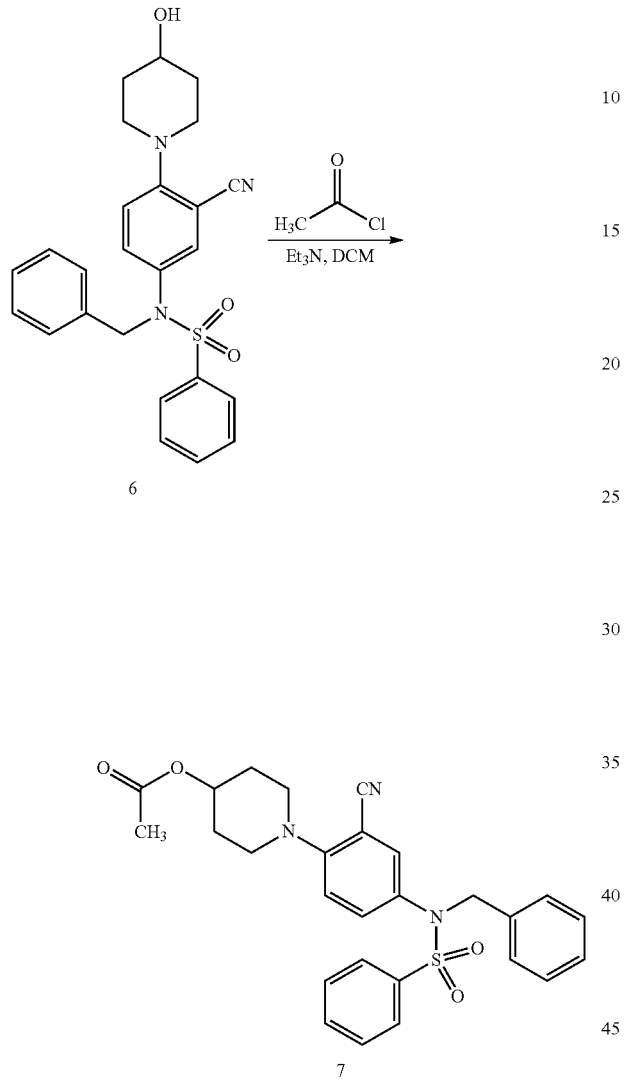

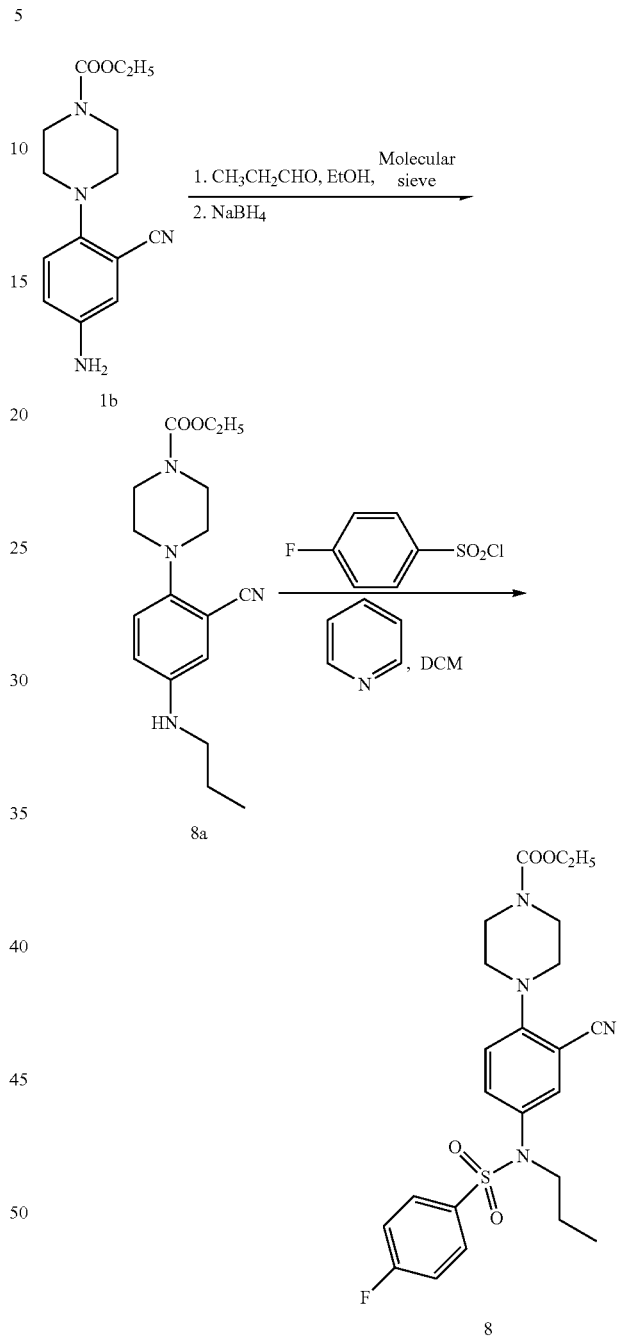

Steps: Compound 6 (0.25 g, 0.56 mmol) was dissolved in 20 mL of dichloromethane, to which triethylamine (0.084 g, 0.83 mmol) and acetyl chloride (0.052 g, 0.67 mmol) were added, followed by stirring at room temperature for 1 h. After completion of the reaction, the organic layer was washed with saturated saline, dried over anhydrous sodium sulfate, filtered, and concentrated under reduced pressure. The residue was purified with silica gel column chromatography (PE:EA=2:1, v/v) to give 7, with a yield of 51.2%. $^1$H NMR (500 MHz, Chloroform-d): δ 7.70-7.64 (m, 3H), 7.55 (t, J=7.8 Hz, 2H), 7.25-7.21 (m, 3H), 7.20-7.17 (m, 2H), 7.13 (dd, J=7.9, 2.6 Hz, 1H), 7.05 (d, J=2.6 Hz, 1H), 6.83 (d, J=7.9 Hz, 1H), 5.00-4.91 (m, 1H), 4.67 (s, 2H), 3.44-3.30 (m, 2H), 3.12-3.04 (m, 2H), 2.08 (s, 3H), 2.07-2.02 (m, 2H), 1.92-1.81 (m, 2H); ESI-MS: m/z=490[M+1]$^+$.

Step 1. Synthesis of ethyl 4-(2-cyano-4-(propylamino)phenyl)piperazin-1-formate (8a)

1b (0.3 g, 1.1 mmol) was dissolved in 30 mL of anhydrous ethanol, to which propionaldehyde (0.095 g, 1.6 mmol) and 0.3 g of molecular sieve were added, and allowed for reaction under reflux for 4 h. Thereafter, the reaction mixture was cooled to room temperature, to which sodium borohydride (0.05 g, 1.3 mmol) was added, and allowed for reaction at room temperature for another 1 h. The resultant reaction mixture was diluted with water, extracted with ethyl acetate, washed with saturated saline, dried over anhydrous sodium sulfate, and concentrated under reduced pressure. The residue was purified with silica gel column chromatography (DCM:EA=5:1, v/v) to give 8a, with a yield of 38.1%; ESI-MS: m/z=317[M+1]+.

Step 2. Synthesis of ethyl 4-(2-cyano-4-((4-fluoro-N-propylphenyl) sulfonamido)phenyl)piperazin-1-formate (Compound 8)

The synthesis was accomplished with reference to Step 4 of Example 1, except that 8a and p-fluorobenzene sulfonyl chloride were used as raw materials to prepare compound 8, with a yield of 49.3%. ¹H NMR (500 MHz, Chloroform-d): δ 7.65-7.60 (m, 2H), 7.25 (dd, J=8.8, 2.6 Hz, 1H), 7.22-7.16 (m, 3H), 6.94 (d, J=8.8 Hz, 1H), 4.19 (q, J=7.1 Hz, 2H), 3.73-3.67 (m, 4H), 3.45 (t, J=7.1 Hz, 2H), 3.24-3.18 (m, 4H), 1.50-1.38 (m, 2H), 1.30 (t, J=7.1 Hz, 3H), 0.91 (t, J=7.4 Hz, 3H); ESI-MS: m/z=475[M+1]+.

Preparation Example 9. Synthesis of ethyl 4-(2-cyano-4-(N-(4-fluorobenzyl)propanesulfonamido) phenyl)piperazin-1-formate (Compound 9)

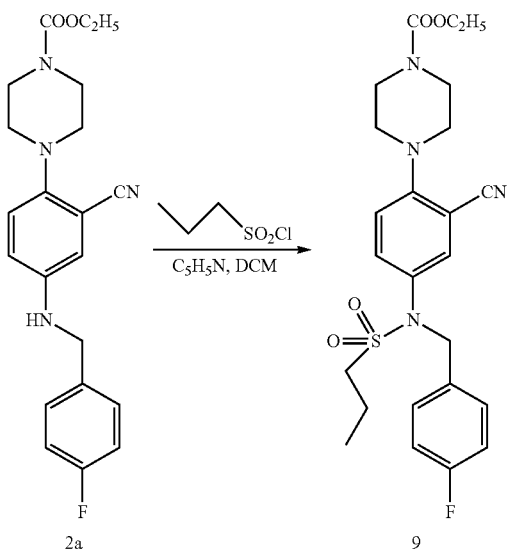

The synthesis was accomplished with reference to Step 4 of Example 1, except that 2a and propane sulfonyl chloride were used as raw materials to prepare compound 9 and the crude product was purified with silica gel column chromatography (PE:EA=2:1, v/v), with a yield of 45.1%. ¹H NMR (500 MHz, Chloroform-d): δ 7.43 (d, J=2.6 Hz, 1H), 7.31 (dd, J=7.8, 2.6 Hz, 1H), 7.23-7.18 (m, 2H), 6.97-6.94 (m, 2H), 6.89 (d, J=8.9 Hz, 1H), 4.77 (s, 2H), 4.17 (q, J=7.1 Hz, 2H), 3.69-3.63 (m, 4H), 3.19-3.14 (m, 4H), 3.05-2.99 (m, 2H), 1.98-1.85 (m, 2H), 1.28 (t, J=7.1 Hz, 3H), 1.08 (t, J=7.4 Hz, 3H); ESI-MS: m/z=489[M+1]+.

Preparation Example 10. Synthesis of N-(3-cyano-4-morpholinyl phenyl)-N-(4-fluorobenzyl)benzene-sulfonamide (compound 10)

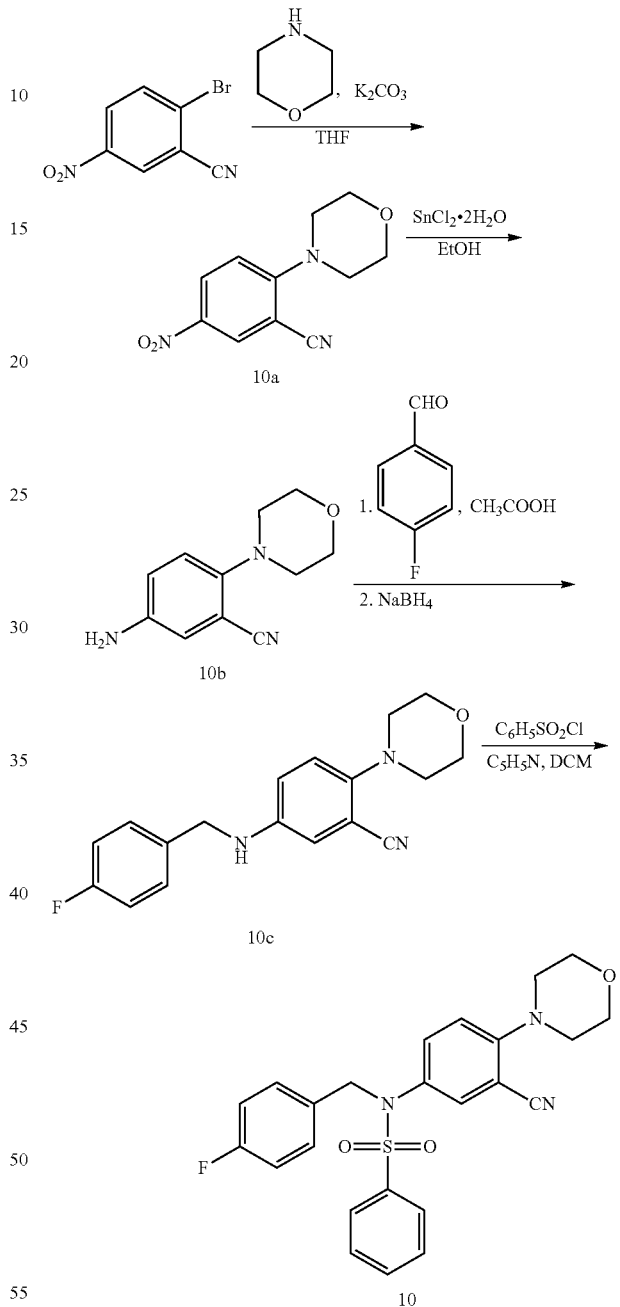

Step 1. Synthesis of 2-morpholinyl-5-nitrobenzonitrile (10a)

2-Bromo-5-nitrobenzonitrile (1.0 g, 4.4 mmol) was dissolved in 20 mL of tetrahydrofuran, to which potassium carbonate (1.22 g, 8.8 mmol) and morpholine (0.58 g, 6.6 mmol) were added. The resultant mixture was heated to reflux for 4 h. After completion of the reaction, the mixture was cooled to room temperature, and filtered. The filtrate was concentrated, and then purified with silica gel column chromatography (PE:EA=4:1, v/v) to give 10a, with a yield of 96.3%; ESI-MS: m/z=234[M+1]$^+$.

Step 2. Synthesis of 2-morpholinyl-5-aminobenzonitrile (10b)

10a (1.0 g, 4.29 mmol) was dissolved in 10 mL of anhydrous ethanol, to which stannous chloride dihydrate (4.84 g, 21.4 mmol) was added. The resultant mixture was heated to reflux for 6 h. After completion of the reaction, the reaction mixture was cooled to room temperature, alkalized with a sodium bicarbonate solution, and filtered. The filtrate was extracted with ethyl acetate. The organic layers were combined, washed with saturated saline, dried over anhydrous sodium sulfate, filtered and concentrated under reduced pressure. The residue was recrystallized with ethyl acetate, to give 10b, with a yield of 51.6%; ESI-MS: m/z=204[M+1]$^+$.

Step 3. Synthesis of 5-((4-fluorobenzyl)amino)-2-morpholinylbenzonitrile (10c)

10b (0.48 g, 2.36 mol) was dissolved in 10 mL of acetic acid, to which p-fluorobenzaldehyde (0.35 g, 2.83 mmol) was added, followed by stirring at room temperature for 1 h, and to which sodium borohydride (0.134 g, 3.54 mmol) was added at 10-15° C., and allowed for reaction for another 0.5 h with the temperature maintained. After completion of the reaction, the reaction mixture was poured into water, alkalized with a sodium bicarbonate solution, and extracted with ethyl acetate. The organic layers were combined, dried over anhydrous sodium sulfate, filtered and concentrated under reduced pressure. The residue was recrystallized with ethyl acetate to give 10c, with a yield of 27.2%; ESI-MS: m/z=312 [M+1]$^+$.

Step 4. Synthesis of N-(3-cyano-4-morpholinylphenyl)-N-(4-fluorobenzyl) benzenesulfonamide (Compound 10)

10c (0.2 g, 0.64 mmol) was dissolved in 10 mL of dichloromethane, to which pyridine (0.25 g, 3.2 mmol) and propane sulfonyl chloride (0.15 g, 0.82 mmol) were added, and allowed for reaction at room temperature for 6 h. After completion of the reaction, the resultant mixture was poured into water. The organic phase was washed with diluted HCl solution, and extracted with dichloromethane. The organic phases were combined, washed with saturated saline, dried over anhydrous sodium sulfate, filtered, and concentrated. The residue was purified with silica gel column chromatography (PE:EA=4:1, v/v), to give 10, with a yield of 74.7%. $^1$H NMR (500 MHz, Chloroform-d): δ 7.70-7.64 (m, 3H), 7.56 (t, J=7.8 Hz, 2H), 7.21-7.16 (m, 2H), 7.14 (dd, J=7.9, 2.6 Hz, 1H), 7.05 (d, J=2.6 Hz, 1H), 6.99-6.92 (m, 2H), 6.83 (d, J=8.9 Hz, 1H), 4.64 (s, 2H), 3.94-3.79 (m, 4H), 3.33-3.12 (m, 4H); ESI-MS: m/z=452[M+1]$^+$.

Preparation Example 11. Synthesis of 4-(4-(N-benzylbenzenesulfonamido)-2-cyanophenyl)-N,N-dimethylpiperazin-1-formamide (Compound 11)

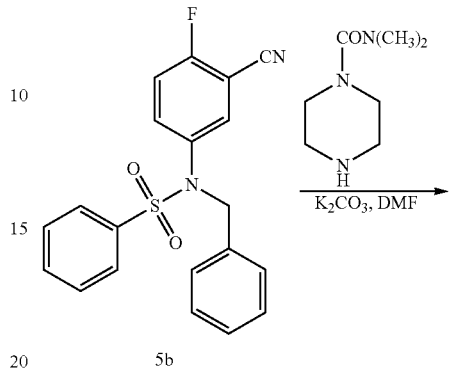

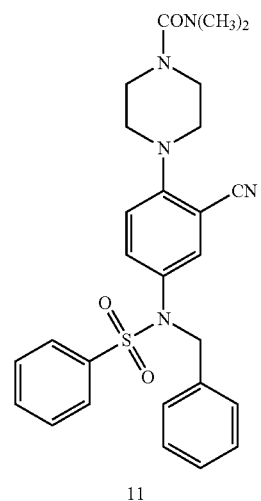

Steps: To a reaction flask, 5b (0.106 g, 0.29 mol), N,N-dimethylpiperazin-1-formamide (0.05 mg, 0.32 mmol), potassium carbonate (0.12 g, 0.87 mmol) and 2 mL of DMF were added, warmed to 100° C., and allowed for reaction for 2 h. After completion of the reaction, the reaction mixture was cooled to room temperature, diluted with water, extracted with ethyl acetate, washed with saturated saline, dried over anhydrous sodium sulfate, filtered, and concentrated. The residue was purified with silica gel column chromatography (DCM:MeOH=20:1), to give 11, with a yield of 65.2%. $^1$H NMR (500 MHz, Chloroform-d): δ 7.71-7.64 (m, 3H), 7.55 (t, J=7.8 Hz, 2H), 7.27-7.22 (m, 3H), 7.23-7.18 (m, 2H), 7.13 (dd, J=7.9, 2.6 Hz, 1H), 7.09 (d, J=2.6 Hz, 1H), 6.81 (d, J=7.9 Hz, 1H), 4.67 (s, 2H), 3.48-3.40 (m, 4H), 3.23-3.13 (m, 4H), 2.86 (s, 6H); ESI-MS: m/z=504[M+1]$^+$.

Preparation Example 12. Synthesis of 1-(4-(N-benzylbenzene sulfonamido)-2-cyanophenyl)-N,N-dimethylpiperidin-4-sulfonamide (Compound 12)

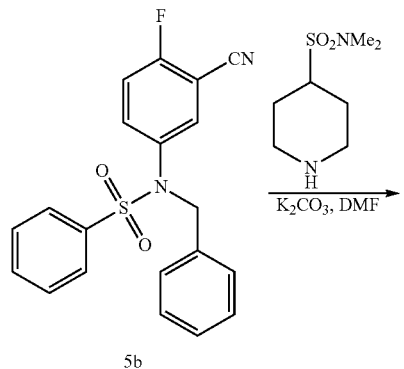

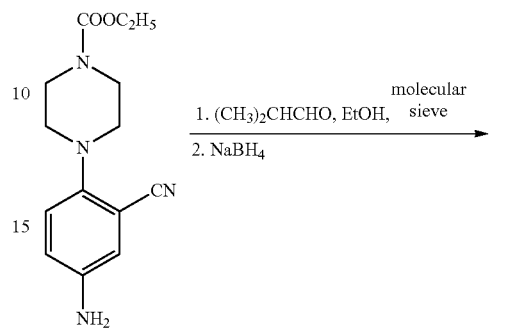

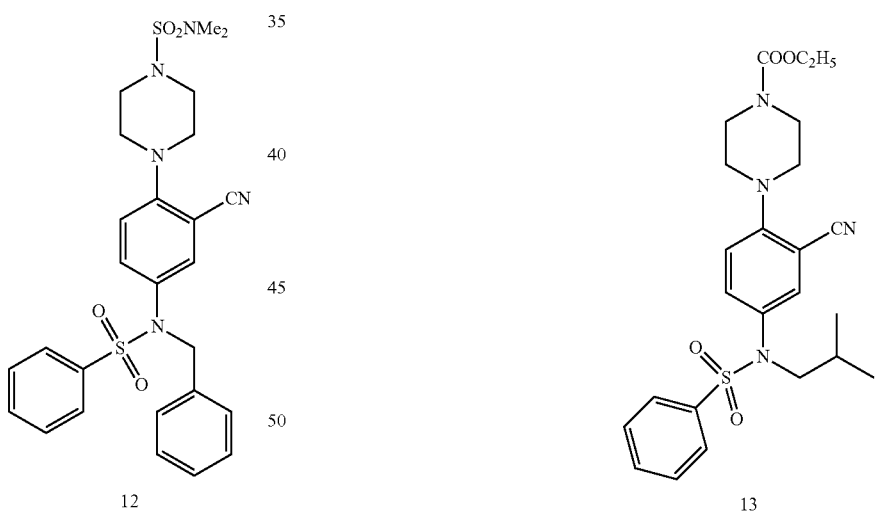

The synthesis was accomplished with reference to Example 11, except that 5b and N,N-dimethylpiperidin-4-sulfonamide were used as raw materials to prepare compound 12, with a yield of 78.0%. $^1$H NMR (500 MHz, Chloroform-d): δ 7.71-7.64 (m, 3H), 7.56 (t, J=7.8 Hz, 2H), 7.27-7.22 (m, 3H), 7.22-7.19 (m, 2H), 7.15 (dd, J=7.8, 2.6 Hz, 1H), 7.07 (d, J=2.6 Hz, 1H), 6.81 (d, J=7.8 Hz, 1H), 4.67 (s, 2H), 3.71-3.66 (m, 2H), 3.16-3.05 (m, 1H), 2.97 (s, 6H), 2.87-2.76 (m, 2H), 2.20-2.15 (m, 2H), 2.13-2.03 (m, 2H); ESI-MS: m/z=539[M+1]$^+$.

Preparation Example 13. Synthesis of ethyl 4-(2-cyano-4-(N-isobutylphenylsulfonamido)phenyl)piperazin-1-formate (compound 13)

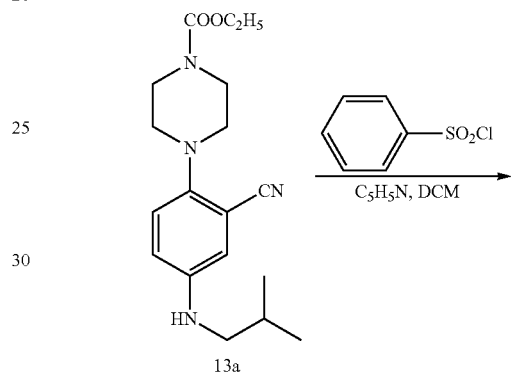

Step 1. Synthesis of ethyl 4-(2-cyano-4-(isobutylamino)phenyl) piperazin-1-formate (13a)

The synthesis was accomplished with reference to Step 1 of Example 8, except that 1b and isobutyraldehyde were used as raw materials to prepare compound 13a, and the residue was purified with silica gel column chromatography (DCM:EA=5:1, v/v), with a yield of 40.1%; ESI-MS: m/z=331[M+1]$^+$.

Step 2. Synthesis of ethyl 4-(2-cyano-4-(N-isobutylphenylsulfonamido) phenyl)piperazin-1-formate (Compound 13)

The synthesis was accomplished with reference to Step 4 of Example 1, except that 13a and benzene sulfonyl chloride were used as raw materials to prepare compound 13, with a yield of 63.4%. $^1$H NMR (500 MHz, Chloroform-d): δ 7.65-7.60 (m, 1H), 7.65-7.62 (m, 1H), 7.60-7.56 (m, 2H), 7.52-7.49 (m, 2H), 7.30-7.28 (m, 1H), 7.13 (d, J=2.6 Hz, 1H), 6.94 (d, J=7.8 Hz, 1H), 4.19 (q, J=7.1 Hz, 2H), 3.73-3.67 (m, 4H), 3.26 (d, J=7.4 Hz, 2H), 3.23-3.17 (m, 4H), 1.59-1.50 (m, 1H), 1.30 (t, J=7.1 Hz, 3H), 0.92 (d, J=6.6 Hz, 6H); ESI-MS: m/z=471[M+1]$^+$.

Preparation Example 14. Synthesis of ethyl 1-(4-(N-benzylbenzene sulfonamido)-2-cyanophenyl) piperidin-4-yl carbamate (Compound 14)

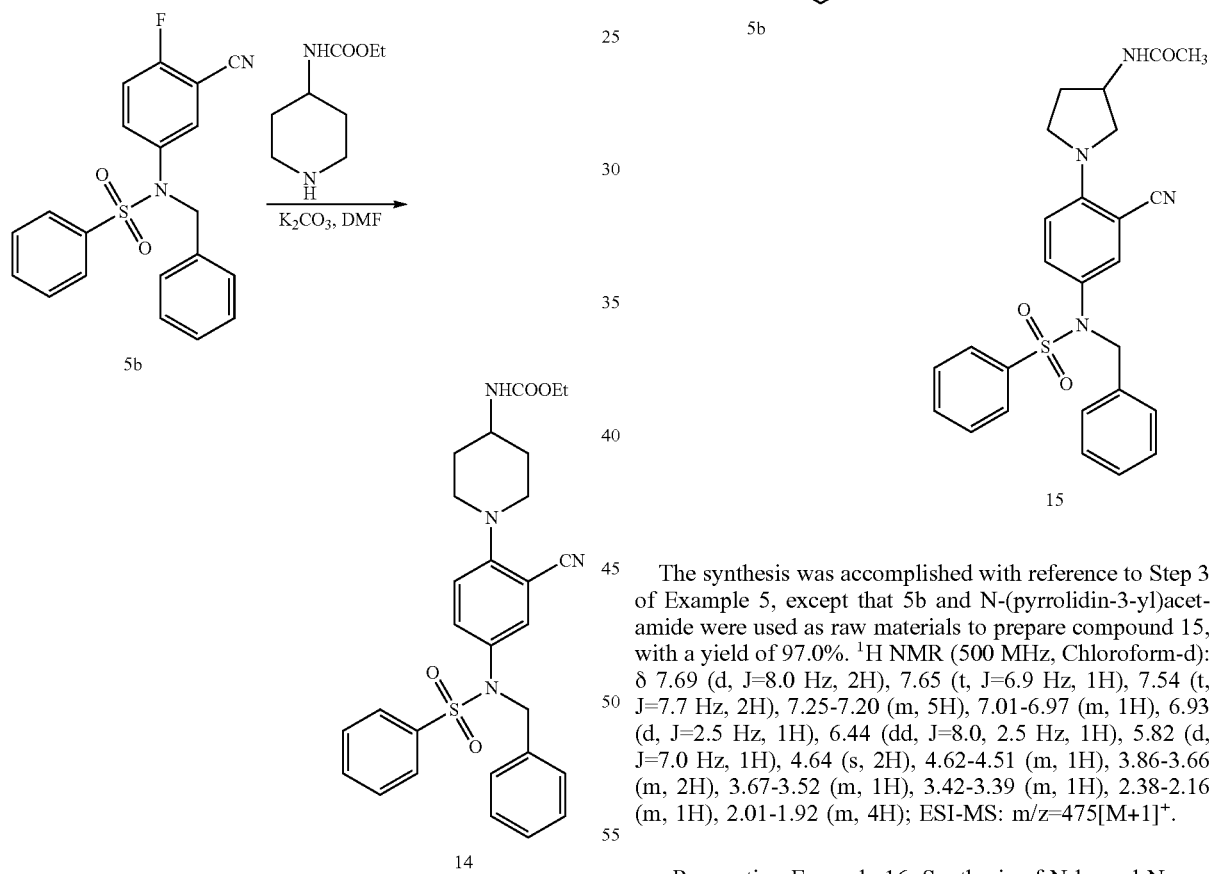

The synthesis was accomplished with reference to Step 3 of Example 5, except that 5b and ethyl piperidin-4-carbamate were used as raw materials to prepare compound 14, with a yield of 65%. $^1$H NMR (500 MHz, Chloroform-d): δ 7.70-7.63 (m, 3H), 7.55 (t, J=7.8 Hz, 2H), 7.27-7.23 (m, 3H), 7.22-7.18 (m, 2H), 7.12 (dd, J=7.9, 2.5 Hz, 1H), 7.05 (d, J=2.5 Hz, 1H), 6.81 (d, J=7.9 Hz, 1H), 4.67 (s, 2H), 4.60 (brs, 1H), 4.13 (q, J=7.0 Hz, 2H), 3.72-3.62 (m, 1H), 3.53-3.47 (m, 2H), 2.94-2.84 (m, 2H), 2.11-2.05 (m, 2H), 1.65-1.60 (m, 2H), 1.26 (t, J=7.0 Hz, 3H); ESI-MS: m/z=519 [M+1]$^+$.

Preparation Example 15. Synthesis of N-(1-(4-(N-benzylbenzene sulfonamido)-2-cyanophenyl)pyrrolidin-3-yl)acetamide (Compound 15)

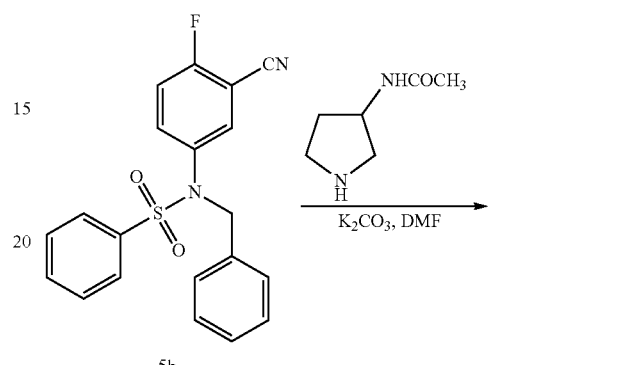

The synthesis was accomplished with reference to Step 3 of Example 5, except that 5b and N-(pyrrolidin-3-yl)acetamide were used as raw materials to prepare compound 15, with a yield of 97.0%. $^1$H NMR (500 MHz, Chloroform-d): δ 7.69 (d, J=8.0 Hz, 2H), 7.65 (t, J=6.9 Hz, 1H), 7.54 (t, J=7.7 Hz, 2H), 7.25-7.20 (m, 5H), 7.01-6.97 (m, 1H), 6.93 (d, J=2.5 Hz, 1H), 6.44 (dd, J=8.0, 2.5 Hz, 1H), 5.82 (d, J=7.0 Hz, 1H), 4.64 (s, 2H), 4.62-4.51 (m, 1H), 3.86-3.66 (m, 2H), 3.67-3.52 (m, 1H), 3.42-3.39 (m, 1H), 2.38-2.16 (m, 1H), 2.01-1.92 (m, 4H); ESI-MS: m/z=475[M+1]$^+$.

Preparation Example 16. Synthesis of N-benzyl-N-(3-cyano-4-(2,6-dioxopiperidin-1-yl)phenyl)benzenesulfonamide (Compound 16)

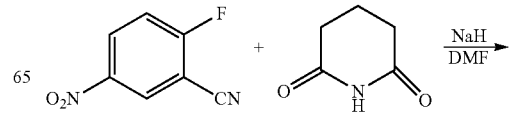

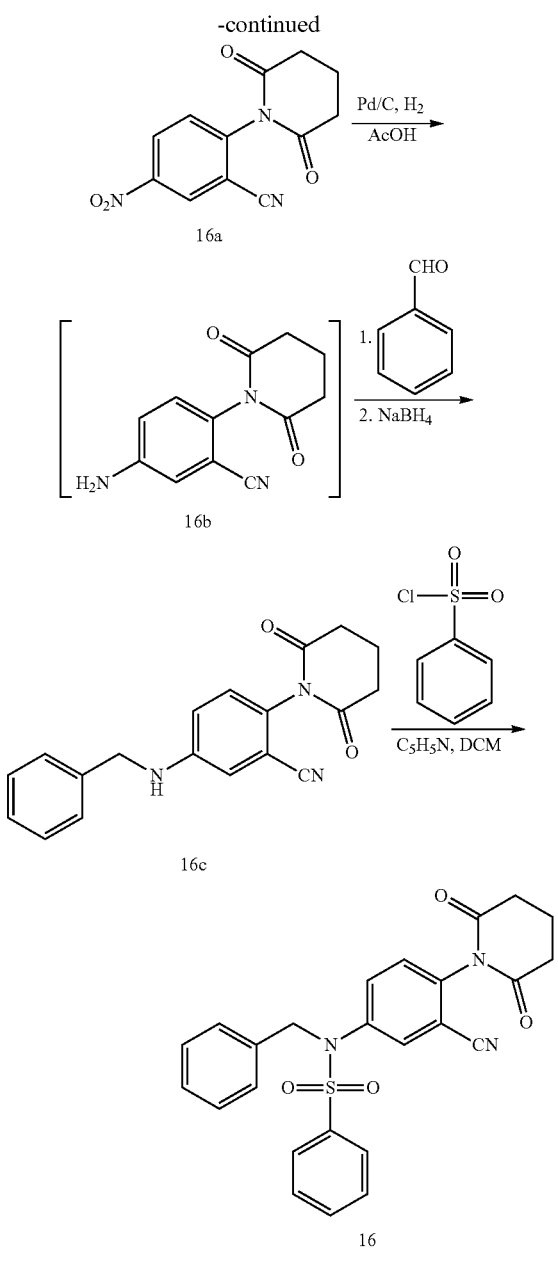

due was purified with silica gel column chromatography (PE:EA=1:1, v/v), to give 16a, with a yield of 25.1%; ESI-MS: m/z=260[M+1]+.

Step 2. Synthesis of 5-(benzylamino)-2-(2,6-dioxopiperidin-1-yl)benzonitrile (16c)

16a (0.25 g, 0.97 mmol) was dissolved in 6 mL of acetic acid, to which 0.05 g of 10% palladium on carbon was added, and allowed for reduction for 1 h at 30° C. with the addition of hydrogen. After completion of the reaction, the reaction mixture was filtered under reduced pressure. To the filtrate, benzaldehyde (0.13 g, 1.24 mmol) was added, and allowed for reaction at room temperature for 1 h, and then cooled to 10-15° C., to which sodium borohydride (0.055 g, 1.45 mmol) was added, and allowed for reaction for 0.5 h with the temperature maintained. After completion of the reaction, the reaction mixture was poured into water, alkalized with sodium bicarbonate, and extracted with ethyl acetate. The organic phases were combined, washed with saturate saline, dried over anhydrous sodium sulfate, filtered, and concentrated under reduced pressure. The residue was purified with silica gel column chromatography (DCM:EA=15:1, v/v), to give 16c. The yield for the two steps was 47.5%; ESI-MS: m/z=320[M+1]+.

Step 3. Synthesis of N-benzyl-N-(3-cyano-4-(2,6-dioxopiperidin-1-yl) phenyl)benzenesulfonamide (Compound 16)

23c (0.14 g, 0.46 mmol) was dissolved in 10 mL of dichloromethane, to which pyridine (0.2 g, 2.53 mmol) and benzene sulfonyl chloride (0.1 g, 0.59 mmol) were further added, and allowed for reaction at room temperature for 1 h. After completion of the reaction, the organic phase was washed with diluted HCl solution, and extracted with dichloromethane. The organic phases were combined, washed with saturated saline, dried over anhydrous sodium sulfate, filtered, and concentrated under reduced pressure. The residue was purified with silica gel column chromatography (PE:EA=1:1, v/v), to give 16, with a yield of 30.6%. $^1$H NMR (500 MHz, Chloroform-d): δ 7.71-7.63 (m, 3H), 7.55 (t, J=7.5, 2H), 7.37 (dd, J=8.0, 2.5 Hz, 1H), 7.34 (d, J=2.5 Hz, 1H), 7.32-7.28 (m, 1H), 7.25-7.21 (m, 4H), 7.13 (d, J=8.0 Hz, 1H), 4.76 (s, 2H), 2.95-2.84 (m, 2H), 2.84-2.71 (m, 2H), 2.29-2.07 (m, 2H); ESI-MS: m/z=460[M+1]+.

Preparation Example 17. Synthesis of N-benzyl-N-(3-cyano-4-(3-methyl-2-oxotetrahydropyrimidin-1 (2H)-yl)phenyl)benzenesulfonamide (Compound 17)

Step 1. Synthesis of 2-(2,6-dioxopiperidin-1-yl)-5-nitrobenzonitrile (16a)

Glutarimide (0.94 g, 8.31 mmol) was dissolved in 5 mL of anhydrous DMF and cooled to 0-5° C., to which 60% sodium hydride (0.33 g, 8.31 mmol) was added in batches, followed by stirring for 0.5 h with the temperature maintained, and to which 2-fluoro-5-nitrobenzonitrile (1.25 g, 7.55 mmol) was further added, warmed to 50° C., and allowed for reaction overnight. After completion of the reaction, the reaction mixture was cooled to room temperature, diluted with water, extracted with ethyl acetate, washed with saturated saline, dried over anhydrous sodium sulfate, filtered, and concentrated under reduced pressure. The resi-

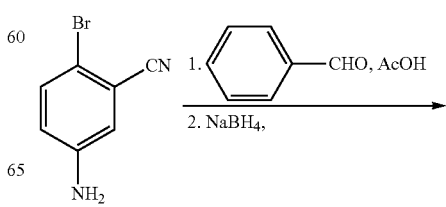

Step 3. Synthesis of N-benzyl-N-(3-cyano-4-(3-methyl-2-oxotetrahydropyrimidin-1(2H)-yl)phenyl)benzensulfonamide (Compound 17)

To a reaction flask, 17b (0.427 g, 1.0 mmol), 0.137 g (1.2 mmol) of 1-methyltetrahydro-2(1H)-pyrimidinone (0.137 g, 1.2 mmol), potassium carbonate (0.276 g, 2.0 mmol), copper iodide (0.019 g, 0.1 mmol) and trans-N,N'-dimethyl-1,2-cyclohexanediamine (0.015 g, 0.1 mmol) and 1 mL of toluene were added, and allowed for reaction at 110° C. under the protection of nitrogen gas for 24 h. After completion of the reaction, the reaction mixture was cooled to room temperature, and filtered. The filtrate was concentrated under reduced pressure. The residue was purified with silica gel column chromatography (DCM:MeOH=20:1), to give 17, with a yield of 11.1%. $^1$H NMR (500 MHz, Chloroform-d): δ 7.70-7.68 (s, 2H), 7.66 (t, J=7.5 Hz, 1H), 7.55 (t, J=7.7 Hz, 2H), 7.26-7.21 (m, 7H), 7.19 (d, J=2.4 Hz, 1H), 4.71 (s, 2H), 3.67 (t, J=6.4 Hz, 2H), 3.42 (t, J=6.1 Hz, 2H), 3.01 (s, 3H), 2.27-2.10 (m, 2H); ESI-MS: m/z=460[M+1]$^+$.

Preparation Example 18. Synthesis of N-benzyl-N-(3-cyano-4-(4-(2-(dimethylamino)ethoxy)piperidin-1-yl)phenyl)benzenesulfonamide (Compound 18)

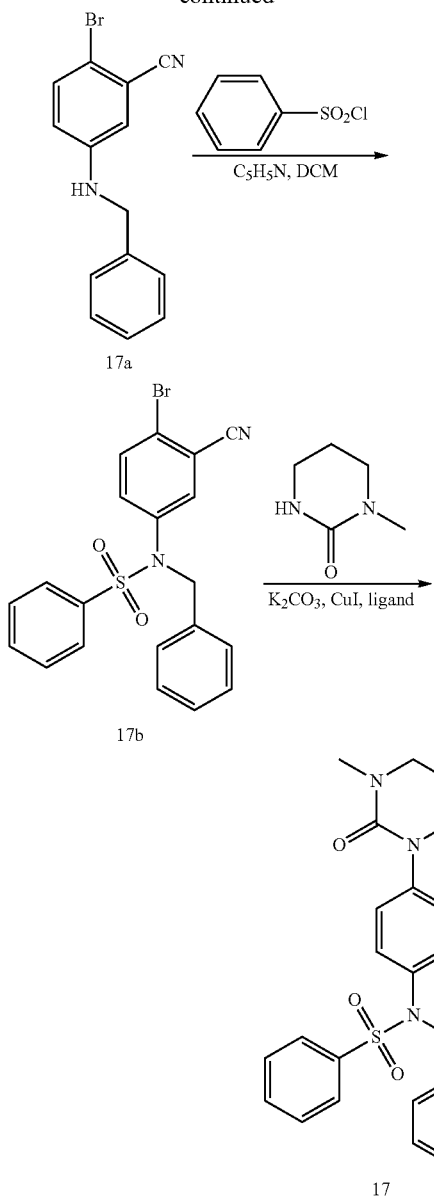

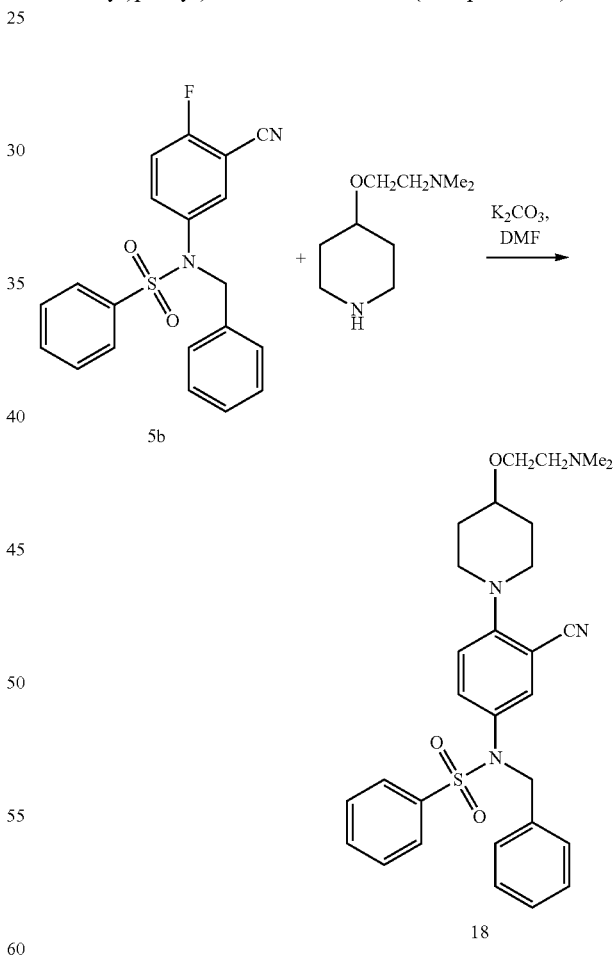

Step 1. Synthesis of 5-(benzylamino)-2-bromobenzonitrile (17a)

The synthesis was accomplished with reference to Step 3 of Example 5, except that 5-amino-2-bromobenzonitrile and benzaldehyde were used as raw materials to prepare compound 17a, with a yield of 85.8%. ESI-MS: m/z=288[M+1]$^+$.

Step 2. Synthesis of N-benzyl-N-(4-bromo-3-cyanophenyl)benzenesulfonamide (17b)

The synthesis was accomplished with reference to Step 4 of Example 5, except that 17a and benzene sulfonyl chloride were used as raw materials to prepare compound 17b, with a yield of 85.0%; ESI-MS: m/z=288[M+1]$^+$.

The synthesis was accomplished with reference to Step 3 of Example 5, except that 5b and N,N-dimethyl-2-(4-piperidyloxy)ethylamine were used as raw materials to prepare compound 18, and the residue was purified with silica gel column chromatography (DCM:MeOH:TEA=40:1:1), to give 18, with a yield of 68%. $^1$H NMR (500 MHz, Chloroform-d): δ 7.70-7.63 (m, 3H), 7.55 (t, J=7.8 Hz, 2H), 7.26-7.22 (m, 3H), 7.22-7.19 (m, 2H), 7.10 (dd, J=8.9, 2.6 Hz, 1H), 7.02 (d, J=2.6 Hz, 1H), 6.80 (d, J=8.9 Hz, 1H), 4.66 (s, 2H), 3.60 (t, J=5.9 Hz, 2H), 3.54-3.48 (m, 1H), 3.45-3.37 (m, 2H), 3.06-2.95 (m, 2H), 2.55 (t, J=5.9 Hz, 2H), 2.31 (s, 6H), 2.04-1.94 (m, 2H), 1.87-1.75 (m, 2H); ESI-MS: m/z=519[M+1]+.
Preparation Example 19. Synthesis of N-(3-cyano-4-(4-hydroxypiperidin-1-yl)phenyl)-N-(4-fluorobenzyl)propane-1-sulfonamide (Compound 19)
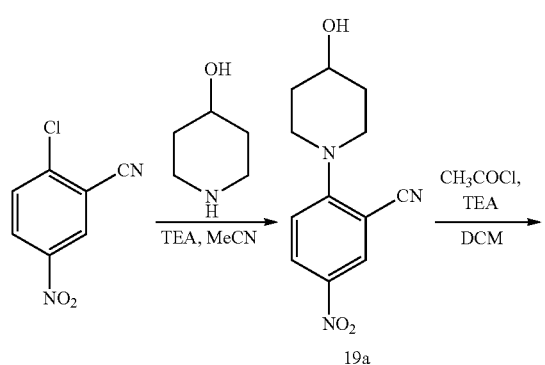
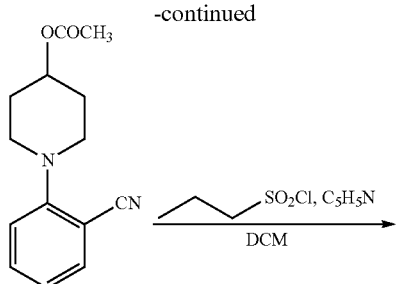
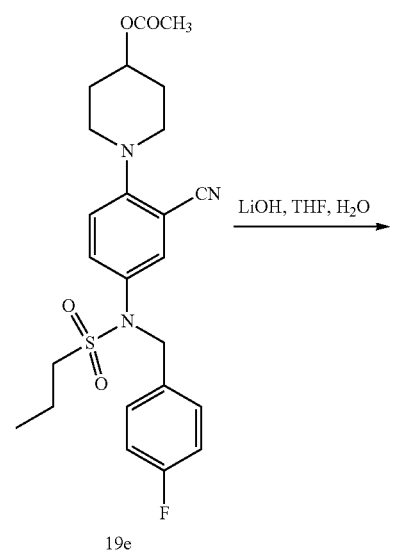
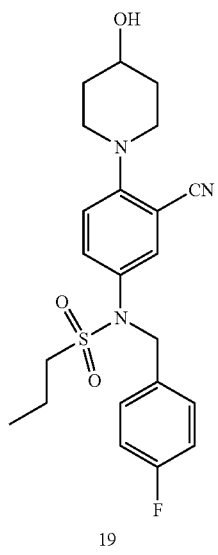

Step 1. Synthesis of 2-(4-hydroxypiperidin-1-yl)-5-nitrobenzonitrile (19a)

2-Chloro-5-nitrobenzonitrile (1.5 g, 8.21 mmol), 4-hydroxypiperidine (0.87 g, 8.63 mmol) and triethylamine (1.25 g, 12.3 mmol) were dissolved in 20 mL of acetonitrile, warmed to 80° C. and allowed for reaction for 2 h. The resultant mixture was concentrated under reduced pressure. The residue was purified with silica gel column chromatography (DCM:MeOH=20:1, v/v), to give 19a, with a yield of 74.4%; ESI-MS: m/z=248[M+1]$^+$.

Step 2. Synthesis of 1-(2-cyano-4-nitrophenyl)piperidin-4-ylacetate (19b)

19a (1.2 g, 4.85 mmol) was dissolved in 20 mL of DCM, to which triethylamine (0.74 g, 7.28 mmol) was added. The resultant mixture was then cooled to 0-5° C., to which acetyl chloride (0.46 g, 5.82 mmol) was added dropwise. Thereafter, the mixture was warmed to room temperature, and allowed for reaction for 1 h. The resultant mixture was concentrated under reduced pressure. The residue was purified with silica gel column chromatography (PE:EA=1:1, v/v), to give 19b, with a yield of 54.1%; ESI-MS: m/z=290 [M+1]$^+$.

Step 3. Synthesis of 1-(4-amino-2-cyanophenyl)piperidin-4-ylacetate (19c)

19b (0.75 g, 2.59 mmol) and stannous chloride dihydrate (2.93 g, 12.96 mmol) were dissolved in 20 mL of ethanol, and allowed for reaction under reflux for 2 h. After completion of the reaction, the reaction mixture was cooled to room temperature, alkalized with a sodium carbonate solution, and filtered. The filtrate was extracted with ethyl acetate, washed with saturate saline, dried over anhydrous sodium sulfate, filtered and concentrated under reduced pressure. The residue was purified with silica gel column chromatography (PE:EA=2:1, v/v), to give 19c, with a yield of 81.8%; ESI-MS: m/z=260[M+1]$^+$.

Step 4. Synthesis of 1-(2-cyano-4-((4-fluorobenzyl)amino)phenyl) piperidin-4-ylacetate (19d)

The synthesis was accomplished with reference to Step 3 of Example 1, except that the intermediate 19c and p-fluorobenzaldehyde were used as raw materials to prepare compound 19d, and the obtained crude product was purified with silica gel column chromatography (PE:EA=2:1, v/v), to give 19d, with a yield of 81.1%; ESI-MS: m/z=368[M+1]$^+$.

Step 5. Synthesis of 1-(2-cyano-4-(N-(4-fluorobenzyl)propylsulfonamido) phenyl)piperidin-4-ylacetate (19e)

The synthesis was accomplished with reference to Step 2 of Example 2, except that the intermediate 19d and propanesulfonyl chloride were used as raw materials to prepare compound 19e, and the obtained crude product was purified with silica gel column chromatography (PE:EA=2:1, v/v), to give 19e, with a yield of 69.8%; ESI-MS: m/z=474[M+1]$^+$.

Step 6. Synthesis of N-(3-cyano-4-(4-hydroxypiperidin-1-yl)phenyl)-N-(4-fluorobenzyl)propane-1-sulfonamide (Compound 19)

19e (0.16 g, 0.34 mmol) and lithium hydroxide (0.033 g, 1.35 mmol) were dissolved in a mixture of 4 mL of THF and 1 mL of water, followed by stirring at room temperature overnight, and then diluted with water, extracted with ethyl acetate, dried over anhydrous sodium sulfate, filtered, and concentrated under reduced pressure. The residue was purified with silica gel column chromatography (DCM:EA=10:1, v/v), to give 19, with a yield of 96.0%. 1H NMR (500 MHz, Chloroform-d): δ 7.39 (d, J=2.6 Hz, 1H), 7.24 (dd, J=7.9, 2.6, 1H), 7.24-7.19 (m, 2H), 7.00-6.96 (m, 2H), 6.90 (d, J=7.9 Hz, 1H), 4.76 (s, 2H), 4.13-3.73 (m, 1H), 3.59-3.46 (m, 2H), 3.13-2.85 (m, 4H), 2.22-1.97 (m, 2H), 2.02-1.83 (m, 2H), 1.84-1.71 (m, 2H), 1.09 (t, J=7.4 Hz, 3H); ESI-MS: m/z=432[M+1]$^+$.

Preparation Example 20. Synthesis of N-(3-cyano-4-(4-hydroxypiperidin-1-yl)phenyl)-N-(4-fluorobenzyl)benzenesulfonamide (Compound 20)

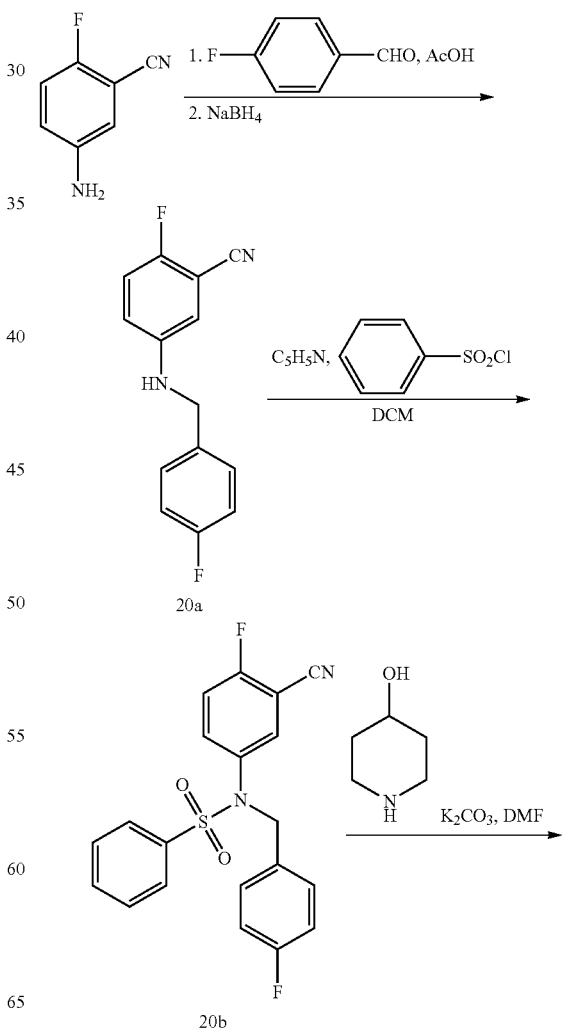

-continued

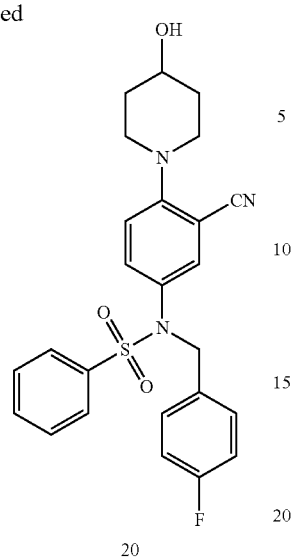
20

Step 1. Synthesis of 2-fluoro-5-((4-fluorobenzyl)amino)benzonitrile (20a)

The synthesis was accomplished with reference to Step 1 of Example 5, except that 5b and p-fluorobenzaldehyde were used as raw materials to prepare compound 20a, with a yield of 91.1%. ESI-MS: m/z=245[M+1]$^+$.

Step 2. Synthesis of N-(3-cyano-4-fluorophenyl)-N-(4-fluorobenzyl) benzenesulfonamide (20b)

The synthesis was accomplished with reference to Step 2 of Example 5, except that 5c and benzene sulfonyl chloride were used as raw materials to prepare compound 20b, with a yield of 89.0%; ESI-MS: m/z=385[M+1]$^+$.

Step 3. Synthesis of N-(3-cyano-4-(4-hydroxypiperidin-1-yl)phenyl)-N-(4-fluorobenzyl)benzenesulfonamide (Compound 20)

The synthesis was accomplished with reference to Example 11, except that 20b and 4-hydroxypiperidine were used as raw materials to prepare compound 20, and the obtained crude product was purified with silica gel column chromatography (DCM:EA=10:1, v/v), with a yield of 96%. 1H NMR (500 MHz, Chloroform-d): δ 7.71-7.62 (m, 3H), 7.59-7.51 (m, 2H), 7.21-7.15 (m, 2H), 7.11-7.04 (m, 1H), 7.04-6.99 (m, 1H), 6.98-6.90 (m, 2H), 6.83 (dd, J=7.9, 2.6 Hz, 1H), 4.63 (s, 2H), 3.95-3.81 (m, 1H), 3.63-3.41 (m, 2H), 3.11-2.93 (m, 2H), 2.14-1.98 (m, 2H), 1.84-1.67 (m, 2H); ESI-MS: m/z=466[M+1]$^+$.

Preparation Example 21. Synthesis of 4-(2-cyano-4-(N-(4-fluorobenzyl) propyl)phenyl)-N,N-dimethylpiperazin-1-formamide (Compound 21)

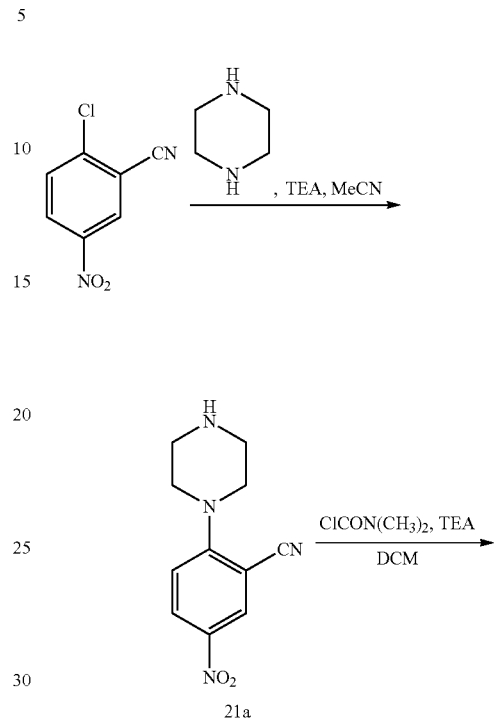

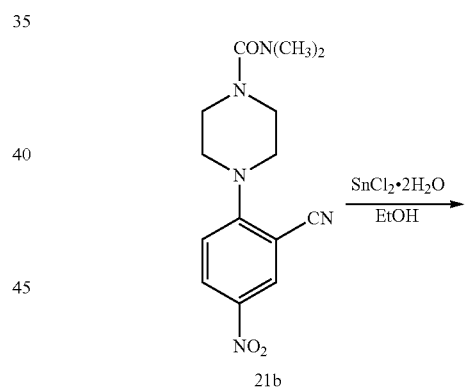

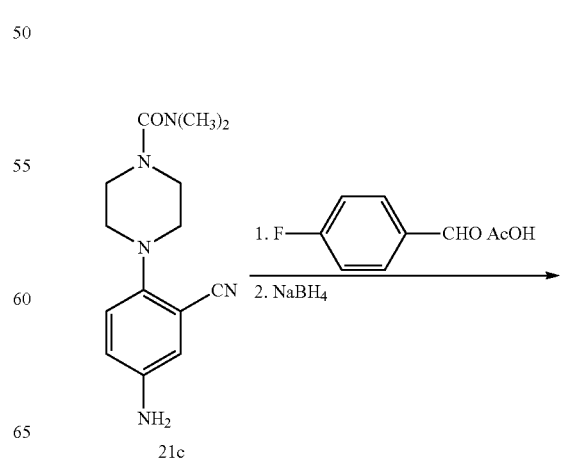

-continued

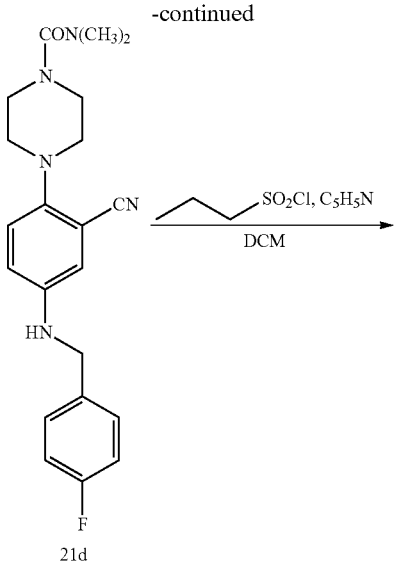

21d

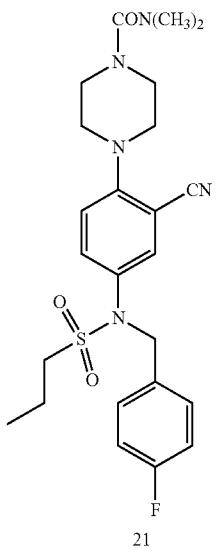

21

Step 1. Synthesis of 5-nitro-2-(piperazin-1-yl)benzonitrile (21a)

The synthesis was accomplished with reference to Step 1 of Example 1, except that 2-fluoro-5-nitrobenzonitrile and piperazine were used as raw materials to prepare compound 21a, with a yield of 98.2%. ESI-MS: m/z=233[M+1]$^+$.

Step 2. Synthesis of 4-(2-cyano-4-nitrophenyl)-N,N-dimethylpiperazin-1-formamide (21b)

21a (0.5 g, 2.15 mmol) was dissolved in 10 mL of DCM, to which triethylamine (0.65 g, 6.46 mmol) was added. The resultant mixture was cooled to 0-5° C., to which dimethylamino formal chloride (0.35 g, 3.23 mmol) was added dropwise. Thereafter, the resultant mixture was warmed to room temperature, and allowed for reaction for 2 h. After completion of the reaction, the reaction mixture was concentrated under reduced pressure. The residue was purified with silica gel column chromatography (DCM:MeOH=20:1, v/v), to give 21b, with a yield of 91%; ESI-MS: m/z=304 [M+1]$^+$.

Step 3. Synthesis of 4-(4-amino-2-cyanophenyl)-N,N-dimethylpiperazin-1-formamide (21c)

The synthesis was accomplished with reference to Step 2 of Example 1, except that 21b was used as raw material to prepare compound 21c, and the obtained crude product was purified with silica gel column chromatography (DCM:MeOH=20:1, v/v), with a yield of 87.6%; ESI-MS: m/z=248 [M+1]$^+$.

Step 4. Synthesis of 4-(2-cyano-4-((4-fluorobenzyl)amino)phenyl)-N,N-dimethylpiperazin-1-formamide (21d)

The synthesis was accomplished with reference to Step 3 of Example 1, except that 21c and p-fluorobenzaldehyde were used as raw materials to prepare compound 21d, and the obtained crude product was purified with silica gel column chromatography (DCM:MeOH=20:1, v/v), with a yield of 86.0%; ESI-MS: m/z=382[M+1]$^+$.

Step 5. Synthesis of 4-(2-cyano-4-(N-(4-fluorobenzyl)propyl)phenyl)-N,N-dimethylpiperazin-1-formamide (Compound 21)

The synthesis was accomplished with reference to Step 4 of Example 1, except that 21d and propane sulfonyl chloride were used as raw materials to prepare compound 21, and the obtained crude product was purified with silica gel column chromatography (PE:EA=2:1, v/v), with a yield of 46.9%. $^1$H NMR (500 MHz, Chloroform-d): δ 7.42 (d, J=2.5 Hz, 1H), 7.30 (dd, J=7.9, 2.5 Hz, 1H), 7.24-7.16 (m, 2H), 6.98 (t, J=8.6 Hz, 2H), 6.89 (d, J=7.9 Hz, 1H), 4.77 (s, 2H), 3.56-3.37 (m, 4H), 3.27-3.14 (m, 4H), 3.09-2.94 (m, 2H), 2.86 (s, 6H), 1.99-1.84 (m, 2H), 1.09 (t, J=7.4 Hz, 3H); ESI-MS: m/z=488[M+1]$^+$.

Preparation Example 22. Synthesis of Compounds 22-36

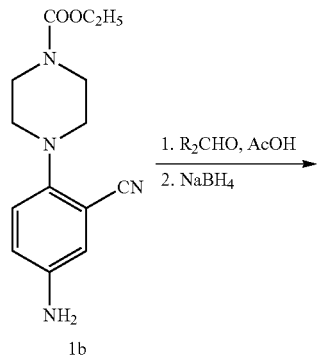

1b

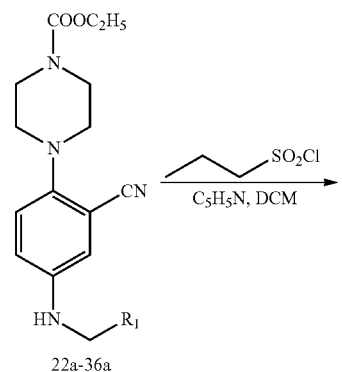

22a-36a

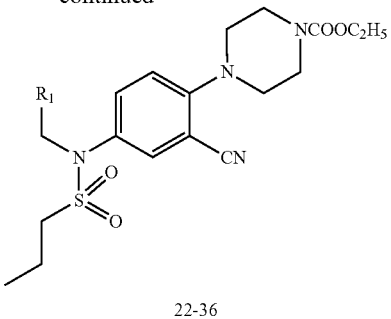

22-36

22a, 22: $R_1$ = phenyl
23a, 23: $R_1$ = 3-fluorophenyl
24a, 24: $R_1$ = 4-chlorophenyl
25a, 25: $R_1$ = 2-fluorophenyl
26a, 26: $R_1$ = 3-methoxyphenyl
27a, 27: $R_1$ = 4-methoxyphenyl
28a, 28: $R_1$ = 2,4-dimethoxyphenyl
29a, 29: $R_1$ = 2-fluoro-4-methoxyphenyl
30a, 30: $R_1$ = 2-methoxy-4-fluorophenyl
31a, 31: $R_1$ = pyrimidin-4-yl
32a, 31: $R_1$ = pyridin-4-yl
33a, 33: $R_1$ = furan-2-yl
34a, 34: $R_1$ = thiazol-4-yl
35a, 35: $R_1$ = 1-methylimidazol-5-yl
36a, 36: $R_1$ = 1-methylpyrazol-5-yl

Step 1. Synthesis of Intermediates 22a-36a

The synthesis was accomplished with reference to Step 3 of Example 1, except that 1b and corresponding aromatic aldehyde were used as raw materials to prepare compounds 22a-36a.

Step 2. Synthesis of Compounds 22-36

The synthesis was accomplished with reference to Step 3 of Example 3, except that 22a-36a and propane sulfonyl chloride were used as raw materials to prepare compounds 22-36.

TABLE 1.1

| Preparation Example Compound No. | Name and structure of the compound | $^1$H NMR and MS(ESI) |
|---|---|---|
| Compound 22 | Ethyl 4-(4-(N-benzylpropanesulfonamido)2-cyanophenyl)piperazin-1-formate | $^1$HNMR(500 MHz, Chloroform-d): δ 7.31-7.29(m, 5H), 6.81(d, J = 7.5 Hz, 1H), 6.77(d, J = 7.5 Hz, 1H), 6.74(s, 1H), 4.56(s, 2H), 4.14(q, J = 8.0 Hz, 2H), 3.32-3.29(m, 8H), 3.11(d, J = 7.1 Hz, 2H), 1.69(m, 2H), 1.22(t, J = 8.0 Hz, 3H), 1.01(t, J = 7.9 Hz, 3H); ESI-MS: m/z = 471[M + 1]$^+$ |

TABLE 1.1-continued

NMR and MS data of compounds 22-36

| Preparation Example Compound No. | Name and structure of the compound | $^1$H NMR and MS(ESI) |
|---|---|---|
| Compound 23 | Ethyl 4-(2-cyano-4-(N-(3-fluoro benzyl)propanesulfonamido)phenyl) piperazin-1-formate 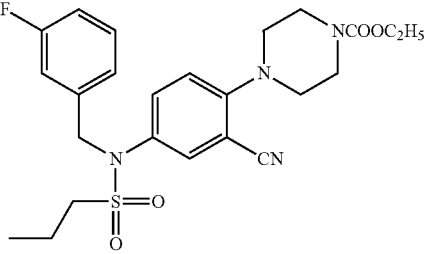 | $^1$H NMR (500 MHz, Chloroform-d): δ 7.36(m, 1H), 7.09(m, 1H), 6.97(d, J = 8.0 Hz, 1H), 6.81-6.74(m, 3H), 4.58(s, 1H), 4.15(q, J = 7.8 Hz, 2H) 3.33-3.30(m, 8H), 3.10(d, J = 7.1 Hz, 2H), 1.70(m, 2H), 1.24(t, J = 7.5 Hz, 3H), 0.99(t, J = 7.2 Hz, 3H); ESI-MS: m/z = 489 [M + 1]$^+$ |
| Compound 24 | Ethyl 4-(4-(4-(N-(4-chlorobenzyl) propanesulfonamido)2-cyanophenyl) piperazin-1-formate 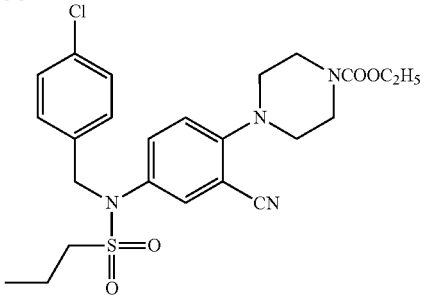 | $^1$HNMR(500 MHz, Chloroform-d): δ 7.48 (d, J = 7.5 Hz, 2H), 7.32(d, J = 7.5 Hz, 2H), 6.83(d, J = 7.5 Hz, 1H), 6.78(d, J = 7.5 Hz, 1H), 6.74(s, 1H), 4.58(s, 2H), 4.14(q, J = 7.9 Hz, 2H), 3.34-3.30(m, 8H), 3.12(d, J = 7.2 Hz, 2H), 1.70(m, 2H), 1.24(t, J = 7.2 Hz, 3H), 1.01(t, J = 7.2 Hz, 3H); ESI-MS: m/z = 506 [M + 1]$^+$ |
| Compound 25 | Ethyl 4-(2-cyano-4-(N-(2-fluoro benzyl)propanesulfonamido)phenyl) piperazin-1-formate 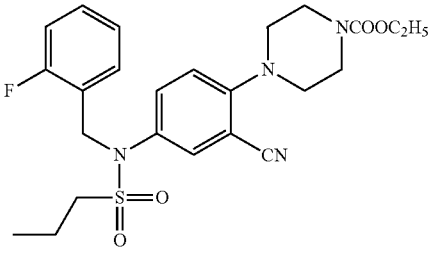 | $^1$HNMR (500 MHz, Chloroform-d): δ 7.72(m, 1H), 7.63(dd, J = 8.0, 7.5 Hz, 1H), 7.26(dd, J = 7.5, 5.0 Hz, 1H), 7.10(m, 1H), 6.82(d, J = 7.5 Hz 1H), 6.77(d, J = 7.5 Hz), 6.75(m, 1H), 4.56(s, 1H), 4.13(q, J = 7.8 Hz, 2H), 3.32-3.30 (m, 8H), 3.11(d, J = 7.1 Hz, 2H), 1.72(m, 2H), 1.25(t, J = 7.5 Hz, 3H), 1.00 (t, J = 7.2 Hz, 3H); ESI-MS: m/z = 489 [M + 1]$^+$ |
| Compound 26 | Ethyl 4-(2-cyano-4-(N-(3-methoxy benzyl)propanesulfonamido)phenyl) piperazin-1-formate 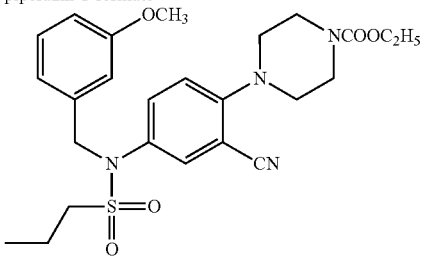 | $^1$HNMR (500 MHz, Chloroform-d): δ 7.25(m, 1H), 6.99-6.97(m, 3H), 6.81(d, J = 7.5 Hz 1H), 6.77 (d, J = 7.5 Hz), 6.74(m, 1H), 4.56(s, 2H), 4.12(q, J = 7.9 Hz, 2H), 3.70(s, 3H), 3.32-3.30 (m, 8H), 3.12(t, J = 7.2 Hz, 2H), 1.68(m, 2H), 1.21(t, J = 7.9 Hz, 3H), 0.98 (t, J = 7.8 Hz, 3H); ESI-MS: m/z = 501 [M + 1]$^+$ |

TABLE 1.1-continued

NMR and MS data of compounds 22-36

| Preparation Example Compound No. | Name and structure of the compound | $^1$H NMR and MS(ESI) |
|---|---|---|
| Compound 27 | Ethyl 4-(2-cyano-4-(N-(4-methoxybenzyl)propanesulfonamido)phenyl)piperazin-1-formate | $^1$HNMR (500 MHz, Chloroform-d): δ 7.13(d, J = 7.5 Hz, 2H), 6.89(d, J = 7.5 Hz, 2H), 6.82(d, J = 7.5 Hz 1H), 6.78 (d, J = 7.5 Hz, 1H), 6.74(s, 1H), 4.56(s, 2H), 4.12(q, J = 7.8 Hz, 2H), 3.81(s, 3H), 3.32-3.29 (m, 8H), 3.11(t, J = 7.2 Hz, 2H), 1.68(m, 2H), 1.22(t, J = 8.0 Hz, 3H), 0.99 (t, J = 8.0 Hz, 3H); ESI-MS: m/z = 531 [M + 1]$^+$ |
| Compound 28 | Ethyl 4-(2-cyano-4-(N-(3,4-dimethoxybenzyl)propanesulfonamido)phenyl)piperazin-1-formate | $^1$HNMR (500 MHz, Chloroform-d): δ 7.28(d, J = 7.5 Hz, 1H), 6.81(d, J = 7.5 Hz, 1H), 6.77(d, J = 7.5 Hz 1H), 6.75 (d, J = 7.5 Hz, 1H), 6.61(s, 1H), 6.57(d, J = 7.5 Hz, 1H), 4.55(s, 2H), 4.14(q, J = 7.9 Hz, 2H), 3.84(s, 3H), 3.72(s, 3H), 3.32-3.29 (m, 8H), 3.10(t, J = 7.2 Hz, 2H), 1.68(m, 2H), 1.23(t, J = 7.9 Hz, 3H), 0.98(t, J = 7.9 Hz, 3H); ESI-MS: m/z = 531 [M + 1]$^+$ |
| Compound 29 | Ethyl 4-(2-cyano-4-(N-(2-fluoro-4-methoxybenzyl)propanesulfonamido)phenyl)piperazin-1-formate | $^1$HNMR (500 MHz, Chloroform-d) δ 7.26(dd, J = 7.5, 5.0 Hz, 1H), 7.16(dd, J = 8.0, 1.5 Hz, 1H), 6.81(d, J = 7.5 Hz 1H), 6.77(d, J = 7.5 Hz, 1H), 6.75(s, 1H), 6.66(dd, J = 7.5, 1.5 Hz, 1H), 4.58(s, 2H), 4.11(q, J = 7.8 Hz, 2H), 3.81(s, 3H), 3.33-3.29 (m, 8H), 3.10(t, J = 7.2 Hz, 2H), 1.68(m, 2H), 1.22(t, J = 8.0 Hz, 3H), 0.97 (t, J = 8.0 Hz, 3H); ESI-MS: m/z = 519[M + 1]$^+$ |
| Compound 30 | Ethyl 4-(2-cyano-4-(N-(4-fluoro-2-methoxybenzyl)propanesulfonamido)phenyl)piperazin-1-formate | $^1$HNMR (500 MHz, Chloroform-d): δ 7.28(dd, J = 7.5, 5.0 Hz, 1H), 7.17(dd, J = 8.0, 1.5 Hz, 1H), 6.87(m, 1H), 6.82(d, J = 7.5 Hz 1H), 6.77(d, J = 7.5 Hz, 1H), 6.74(s, 1H), 4.60(s, 2H), 4.12(q, J = 8.0 Hz, 2H), 3.72(s, 3H), 3.32-3.29 (m, 8H), 3.13(t, J = 7.2 Hz, 2H), 1.69(m, 2H), 1.26(t, J = 8.0 Hz, 3H), 0.98 (t, J = 8.0 Hz, 3H); ESI-MS: m/z = 519[M + 1]$^+$ |

TABLE 1.1-continued

NMR and MS data of compounds 22-36

| Preparation Example Compound No. | Name and structure of the compound | $^1$H NMR and MS(ESI) |
|---|---|---|
| Compound 31 | Ethyl 4-(2-cyano-4-(N-(pyrimidin-4-ylmethyl)propanesulfonamido)phenyl)piperazin-1-formate 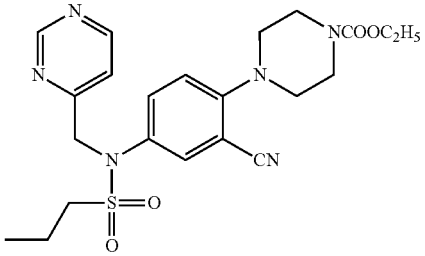 | $^1$HNMR (500 MHz, Chloroform-d): δ 9.12(s, 1H), 8.95(d, J = 7.4 Hz, 1H), 7.21(d, J = 7.4 Hz, 1H), 6.85(d, J = 7.5 Hz 1H), 6.79(d, J = 7.5 Hz, 1H), 6.75(s, 1H), 4.63(s, 2H), 4.12(q, J = 7.4 Hz, 2H), 3.72(s, 3H), 3.32-3.29 (m, 8H), 3.12(t, J = 7.2 Hz, 2H), 1.70(m, 2H), 1.26(t, J = 7.1 Hz, 3H), 0.97 (t, J = 7.1 Hz, 3H); ESI-MS: m/z = 473 [M + 1]$^+$ |
| Compound 32 | Ethyl 4-(2-cyano-4-(N-(pyridin-2-ylmethyl)propanesulfonamido)phenyl)piperazin-1-formate 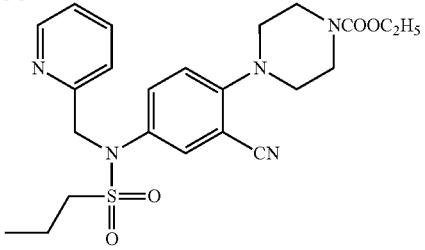 | $^1$HNMR (500 MHz, Chloroform-d): δ 8.51 (d, J = 7.4 Hz, 1H), 7.74(m, 1H), 7.31(d, J = 7.4 Hz, 1H), 7.24(m, 1H), 6.88(d, J = 7.5 Hz 1H), 6.81(d, J = 7.5 Hz, 1H), 6.80(s, 1H), 4.62(s, 2H), 4.78(q, J = 7.4 Hz, 2H), 3.52-3.39 (m, 8H), 3.12(t, J = 7.2 Hz, 2H), 1.73(m, 2H), 1.26(t, J = 7.1 Hz, 3H), 1.01 (t, J = 7.1 Hz, 3H); ESI-MS: m/z = 472 [M + 1]$^+$ |
| Compound 33 | Ethyl 4-(2-cyano-4-(N-(furan-2-ylmethyl)propanesulfonamido)phenyl)piperazin-1-formate 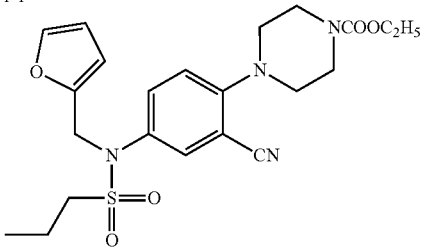 | $^1$HNMR (500 MHz,Chloroform-d): δ 7.55(d, J = 7.4 Hz, 1H), 6.88(d, J = 7.5 Hz 1H), 6.78(d, J = 7.5 Hz, 1H), 6.75(s, 1H), 6.39(m, 1H), 6.29(d, J = 7.2 Hz), 4.53(s, 2H), 4.15(q, J = 7.4 Hz, 2H), 3.35 = 3.30 (m, 8H), 3.12(t, J = 7.2 Hz, 2H), 1.70(m, 2H), 1.26(t, J = 7.1 Hz, 3H), 0.99 (t, J = 7.1 Hz, 3H); ESI-MS: m/z = 461 [M + 1]$^+$ |
| Compound 34 | Ethyl 4-(2-cyano-4-(N-(thiazol-4-ylmethyl)propanesulfonamido)phenyl)piperazin-1-formate 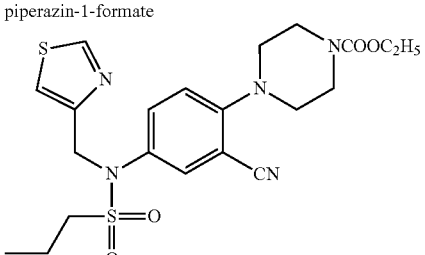 | $^1$HNMR (500 MHz, Chloroform-d): δ 9.07(s, 1H), 6.89(s, 1H), 6.88(d, J = 7.5 Hz 1H), 6.78(d, J = 7.5 Hz, 1H), 6.75(s, 1H), 4.65(s, 2H), 4.17(q, J = 7.4 Hz, 2H), 3.36-3.31 (m, 8H), 3.10(t, J = 7.2 Hz, 2H), 1.69(m, 2H), 1.22(t, J = 7.1 Hz, 3H), 0.98 (t, J = 7.1 Hz, 3H); ESI-MS: m/z = 478[M + 1]$^+$ |

TABLE 1.1-continued

NMR and MS data of compounds 22-36

| Preparation Example Compound No. | Name and structure of the compound | $^1$H NMR and MS(ESI) |
|---|---|---|
| Compound 35 | Ethyl 4-(2-cyano-4-(N-((1-methyl-1H-imidazol-5-yl)methyl)propanesulfonamido)phenyl)piperazin-1-formate | $^1$HNMR (500 MHz, Chloroform-d): δ 7.62(s,1H), 7.18(s, 1H), 6.89(d, J = 7.5 Hz 1H), 6.80(d, J = 7.5 Hz, 1H), 6.77(s, 1H), 4.68(s, 2H), 4.14(q, J = 7.4 Hz, 2H), 3.72(s, 3H), 3.35-3.30 (m, 8H), 3.13(t, J = 7.2 Hz, 2H), 1.69(m, 2H), 1.24(t, J = 7.2 Hz, 3H), 1.01 (t, J = 7.2 Hz, 3H); ESI-MS: m/z = 475[M + 1]$^+$ |
| Compound 36 | Ethyl 4-(2-cyano-4-(N-((1-methyl-1H-pyrazol-5-yl)methyl)propanesulfon-amido)phenyl)piperazin-1-formate | $^1$HNMR (500 MHz, Chloroform-d): δ 7.31(d, J = 7.4 Hz, 1H), 6.86(d, J = 7.5 Hz 1H), 6.81 (d, J = 7.5 Hz, 1H), 6.78(s, 1H), 4.63(s, 2H), 4.15(q, J = 7.4 Hz, 2H), 3.63(s, 3H), 3.32-3.29 (m, 8H), 3.11 (t, J = 7.2 Hz, 2H), 1.70 (m, 2H), 1.21(t, J = 7.2 Hz, 3H), 1.00 (t, J = 7.2 Hz, 3H); ESI-MS: m/z = 475[M + 1]$^+$ |

Preparation Example 23. Synthesis of Compounds 37-48

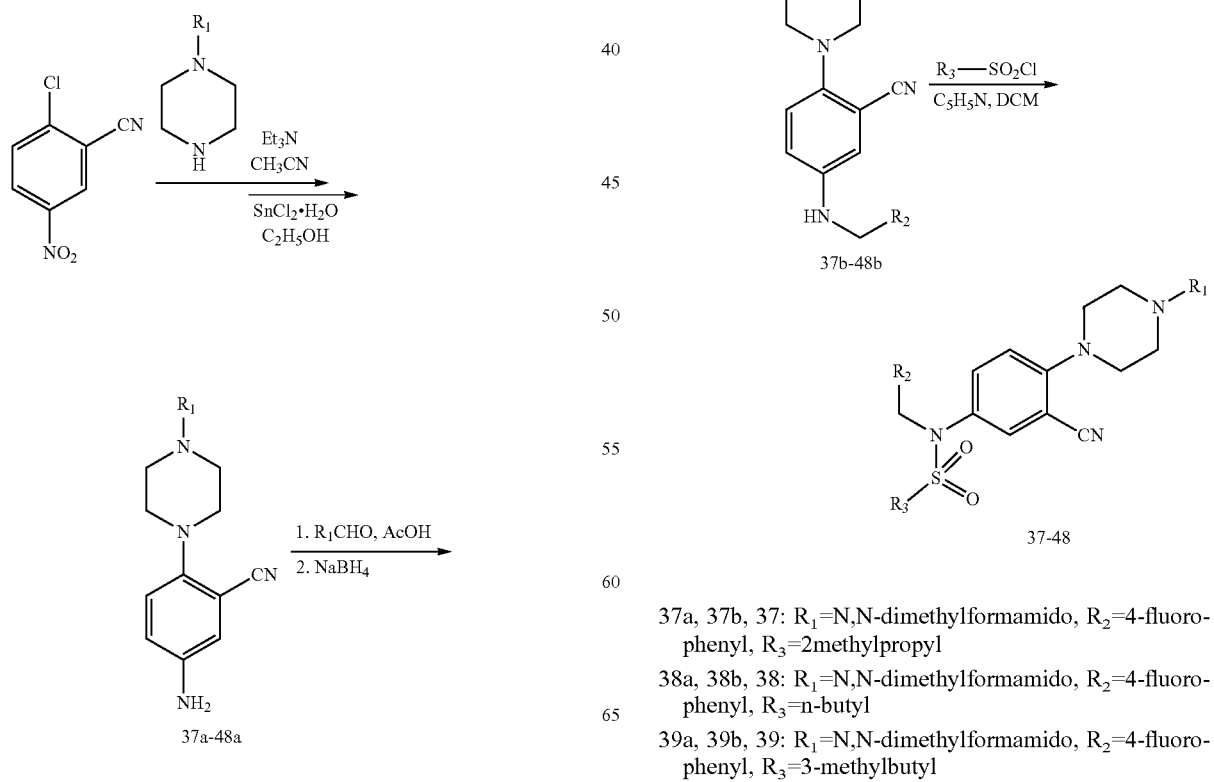

37a, 37b, 37: $R_1$=N,N-dimethylformamido, $R_2$=4-fluorophenyl, $R_3$=2methylpropyl 38a, 38b, 38: $R_1$=N,N-dimethylformamido, $R_2$=4-fluorophenyl, $R_3$=n-butyl 39a, 39b, 39: $R_1$=N,N-dimethylformamido, $R_2$=4-fluorophenyl, $R_3$=3-methylbutyl 40a, 40b, 40: $R_1$=N,N-dimethylformamido, $R_2$=4-fluorophenyl, $R_3$=2,2-dimethylpropyl 41a, 41b, 41: $R_1$=N,N-dimethylformamido, $R_2$=pyridin-4-yl, $R_3$=n-propyl 42a, 42b, 42: $R_1$=N,N-dimethylformamido, $R_2$=pyrimidin-4-yl, $R_3$=n-propyl 43a, 43b, 43: $R_1$=N,N-dimethylformamido, $R_2$=4-fluorophenyl, $R_3$=n-propyl 44a, 44b, 44: $R_1$=N,N-dimethylformamido, $R_2$=4-chlorophenyl, $R_3$=n-propyl 45a, 45b, 45: $R_1$=N,N-dimethylformamido, $R_2$=4-methoxyphenyl, $R_3$=n-propyl 46a, 46b, 46: $R_1$=N,N-dimethylformamido, $R_2$=1-methylpyrazol-5-yl, $R_3$=4-fluorophenyl 47a, 47b, 47: $R_1$=N,N-dimethylformamido, $R_2$=2,4-difluorophenyl, $R_3$=cyclopropylmethyl 48a, 48b, 48: $R_1$=N,N-dimethylformamido, $R_2$=4-fluorophenyl, $R_3$=pyridin-3-yl Step 1. Synthesis of Intermediates 37a-48a The synthesis was accomplished with reference to Steps 1-2 of Example 1, except that 2-chloro-5-nitrobenzonitrile and corresponding monosubstituted piperazine were used as raw materials to prepare compound 37a-48a via substitution and nitro reduction.

Step 2. Synthesis of Compounds 37b-48b

The synthesis was accomplished with reference to Step 3 of Example 1, except that 37a-48a and corresponding aromatic aldehyde were used as raw materials to prepare compounds 37b-48b.

Step 3. Synthesis of Compounds 37-48

The synthesis was accomplished with reference to Step 4 of Example 1, except that 37b-48b and corresponding sulfonyl chloride were used as raw materials to prepare compounds 37-48.

TABLE 1.2

NMR and MS data of compounds 37-48

| Preparation Example Compound No. | Name and structure of compound | $^1$HNMR and MS(ESI) |
|---|---|---|
| Compound 37 | 4-(2-cyano-4-((N-(4-fluorobenzyl)-2-methylpropyl)sulfonamido)phenyl)-N,N-dimethylpiperazin-1-formamide 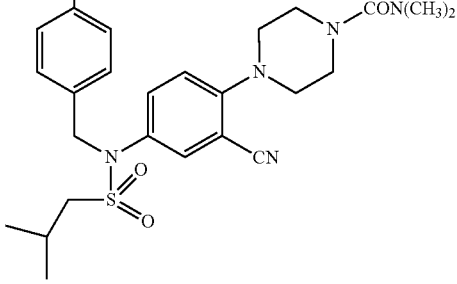 | 1HNMR (500 MHz, Chloroform-d): δ 7.56(dd, J = 7.5, 5.0 Hz, 2H), 7.21(dd, J = 8.0, 7.5 Hz, 2H), 6.81-6.74(m, 3H), 4.67(s, 2H), 3.52(m, 4H), 3.33-3.29 (m, 6H), 2.98(s, 6H), 1.72(m, 1H), 0.93(d, J = 6.8 Hz, 6H); ESI-MS: m/z = 502[M + 1]$^+$ |
| Compound 38 | 4-(2-cyano-4-(N-(4-fluorobenzyl)butanesulfonamido)phenyl)-N,N-dimethylpiperazin-1-formamide 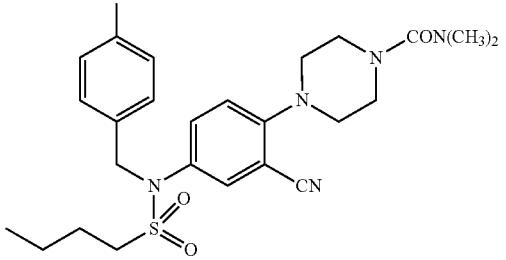 | $^1$HNMR (500 MHz, Chloroform-d): δ 7.65(ddd, J = 7.5, 4.8, 1.5 Hz, 2H), 7.23(ddd, J = 8.0, 7.4, 1.5 Hz, 2H), 7.02(d, J = 7.5 Hz, 1H), 6.88(d, J = 7.5 Hz, 1H), 6.75(s, 1H), 4.62(s, 2H), 3.53(m, 4H), 3.30(m, 4H), 3.15(t, J = 7.2 Hz, 2H), 2.99(s, 6H), 1.61(m, 2H), 1.30(m, 2H), 0.95(t, J = 7.2 Hz, 3H); ESI-MS: m/z = 502[M + 1]$^+$ |

TABLE 1.2-continued

NMR and MS data of compounds 37-48

| Preparation Example Compound No. | Name and structure of compound | ¹HNMR and MS(ESI) |
|---|---|---|
| Compound 39 | 4-(2-cyano-4-((N-(4-fluorobenzyl)-3-methylbutyl)sulfonamido)phenyl)-N,N-dimethylpiperazin-1-formamide | ¹HNMR (500 MHz, Chloroform-d): δ 7.67(ddd, J = 7.5, 5.0, 1.5 Hz, 2H), 7.25(ddd, J = 8.0, 7.5, 1.5 Hz, 2H), 7.00(d, J = 7.5 Hz, 1H), 6.86(d, J = 7.5 Hz, 1H), 6.78(s, 1H), 4.61(s, 2H), 3.51(m, 4H), 3.32(m, 4H), 3.13(t, J = 7.1 Hz, 2H), 3.00(s, 6H), 1.77(m, 2H), 1.62(m, 1H), 0.95(d, J = 7.1 Hz, 6H); ESI-MS: m/z = 516[M + 1]⁺ |
| Compound 40 | 4-(2-cyano-4-((N-(4-fluorobenzyl)-2,2-dimethylpropyl)sulfonamido)phenyl)-N,N-dimethylpiperazin-1-formamide | ¹HNMR (500 MHz, Chloroform-d): δ 7.69(ddd, J = 7.5, 5.0, 1.5 Hz, 2H), 7.27(ddd, J = 8.0, 7.5, 1.5 Hz, 2H), 7.05(d, J = 7.5 Hz, 1H), 6.90(d, J = 7.5 Hz, 1H), 4.67(s, 2H), 3.52(m, 4H), 3.30(m, 4H), 3.27(s, 2H), 2.99(s, 6H), 0.96(s, 9H); ESI-MS: m/z = 526[M + 1]⁺ |
| Compound 41 | 4-(2-cyano-4-(N-(pyridin-4-ylmethyl)propanesulfonamido)phenyl)-N,N-dimethylpiperazin-1-formamide | ¹HNMR (500 MHz, Chloroform-d): δ 6 8.55(d, J = 7.5 Hz, 2H), 7.35(d, J = 7.5 Hz, 2H), 6.91(d, J = 7.5 Hz, 1H), 6.80(d, J = 7.5 Hz, 1H), 6.78(s, 1H), 5.10(s, 2H), 3.52(m, 4H), 3.30(m, 4H), 3.12(t, J = 7.1 Hz, 2H), 2.99(s, 6H), 1.69(m, 2H), 0.98(t, J = 7.1 Hz, 3H); ESI-MS: m/z = 471[M + 1]⁺ |
| Compound 42 | 4-(2-cyano-4-(N-(pyrimidin-4-ylmethyl)propanesulfonamido)phenyl)-N,N-dimethylpiperazin-1-formamide | ¹HNMR (500 MHz,Chloroform-d): δ 9.12(s, H), 8.95(d, J = 7.5 Hz, 1H), 7.25(d, J = 7.5 Hz, 2H), 7.00(d, J = 7.5 Hz, 1H), 6.87(d, J = 7.5 Hz, 1H), 6.77(s, 1H), 458(s, 2H), 3.55(m, 4H), 3.31(m, 4H), 3.13(t, J = 7.1 Hz, 2H), 2.99(s, 6H), 1.69(m, 2H), 0.99(t, J = 7.1 Hz, 3H); ESI-MS: m/z = 472[M + 1]⁺ |

TABLE 1.2-continued

NMR and MS data of compounds 37-48

| Preparation Example Compound No. | Name and structure of compound | ¹HNMR and MS(ESI) |
|---|---|---|
| Compound 43 | 4-(2-cyano-4-(N-(4-fluorobenzyl)ethanesulfonamido)phenyl)-N,N-dimethylpiperazin-1-sulfonamide 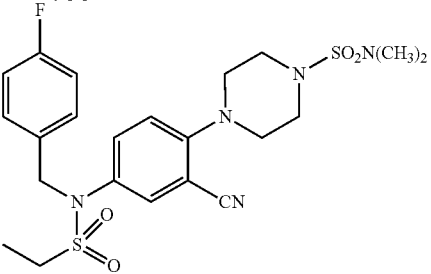 | ¹HNMR (500 MHz, Chloroform-d): δ 7.62(ddd, J = 7.5, 5.0, 1.5 Hz, 2H), 7.21(ddd, J = 8.0, 7.5, 1.5 Hz, 2H), 7.00(d, J = 7.5 Hz, 1H), 6.83(d, J = 7.5 Hz, 1H), 6.73(s, 1H), 4.62(s, 2H) 3.45(q, J = 7.1 Hz, 2H), 3.19(m, 4H), 2.68(s, 6H), 2.58(m, 4H), 1.27(t, J = 7.1 Hz, 3H); ESI-MS: m/z = 510[M + 1]⁺ |
| Compound 44 | 4-(4-(N-(4-chlorobenzyl)propanesulfonamido)-2-cyanophenyl)-N,N-dimethylpiperazin-1-sulfonamide 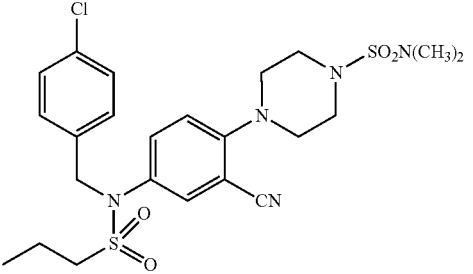 | ¹HNMR (500 MHz, Chloroform-d): δ 7.45(d, J = 7.5 Hz, 2H), 7.35(d, J = 7.5 Hz, 2H), 6.90(d, J = 7.5 Hz, 1H), 6.81(d, J = 7.5 Hz, 1H), 6.77(s, 1H), 4.63(s, 2H), 3.20(m, 4H), 3.12(t, J = 7.1 Hz, 2H), 2.67(s, 6H), 2.58(m, 4H), 1.70(m, 2H), 1.00(t, J = 7.1 Hz, 3H); ESI-MS: m/z = 541[M + 1]⁺ |
| Compound 45 | 4-(2-cyano-4-(N-(4-methoxybenzyl)propanesulfonamido)phenyl)-N,N-dimethylpiperazin-1-sulfonamide 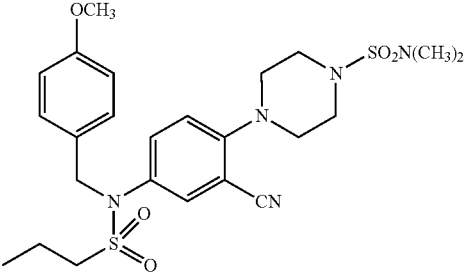 | ¹HNMR (500 MHz, Chloroform-d): δ 7.22(d, J = 7.5 Hz, 2H), 6.99(d, J = 7.5 Hz, 2H), 6.88 (d, J= 7.5 Hz, 1H), 6.79(d, J = 7.5 Hz, 1H), 6.75(s, 1H), 4.62(s, 2H), 3.81(s, 3H), 3.20(m, 2H), 3.10(t, J = 7.1 Hz, 2H), 2.67(s, 6H), 2.58(m, 4H), 1.69(m, 2H), 1.01(t, J = 7.1 Hz, 3H); ESI-MS: m/z = 536[M + 1]⁺ |
| Compound 46 | 4-(2-cyano-4-((4-fluoro-N-((1-methyl-1H-pyrazol-5-yl)methyl)phenyl)sulfonamido)phenyl)-N,N-dimethylpiperazin-1-sulfonamide 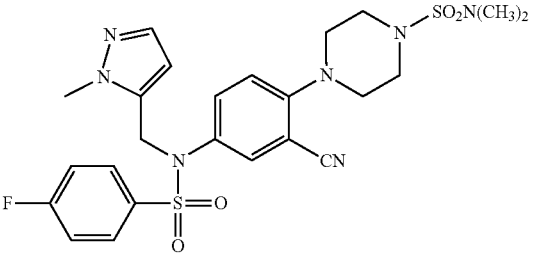 | ¹HNMR (500 MHz, Chloroform-d): δ 8.00(ddd, J = 7.5, 5.0, 1.5 Hz, 2H), 7.45(ddd, J = 8.0, 7.5, 1.5 Hz, 2H), 7.21(d, J = 7.5 Hz, 1H), 6.98(d, J = 7.5 Hz, 1H), 6.80(d, J = 7.5 Hz, 1H), 6.76(s, 1H), 6.05(d, J = 7.5 Hz, 1H), 4.63(s, 2H), 3.63(s, 1H), 3.20(m, 4H), 2.66(s, 6H), 2.58(m, 4H); ESI-MS: m/z = 562[M + 1]⁺ |

TABLE 1.2-continued

NMR and MS data of compounds 37-48

| Preparation Example Compound No. | Name and structure of compound | ¹HNMR and MS(ESI) |
|---|---|---|
| Compound 47 | 4-(2-cyano-4-((1-cyclopropyl-N-(2,4-difluorobenzyl)methyl)sulfonamido)phenyl)-N,N-dimethylpiperazin-1-sulfonamide | 1HNMR (500 MHz, Chloroform-d): δ 7.30(dd, J = 7.5, 5.0 Hz, 1H), 6.96(ddd, J = 8.0, 7.5, 1.5 Hz, 1H), 6.81(d, J = 7.5 Hz, 1H), 6.77-6.71(m, 3H), 4.60(s, 2H), 3.35(d, J = 7.1 Hz, 2H), 3.20(m, 4H), 2.66(s, 6H), 2.57(m, 4H), 1.02(m, 1H), 0.80-0.40(m, 4H); ESI-MS: m/z = 554[M + 1]⁺ |
| Compound 48 | 4-(2-cyano-4-(-N-(4-fuorophenyl)pyridin-3-sulfonamido)phenyl)-N,N-dimethylpiperazin-1-sulfonamide | ¹HNMR (500 MHz, Chloroform-d): δ 8.95(s, 1H), 8.88(d, J = 7.5, 5.0 Hz, 7H), 8.46(d, J = 7.4H, 1H), 7.63(m, 2H), 7.38(dd, J = 7.5, 5.0 Hz, 2H), 7.16(dd, J = 8.0, 7.5 Hz, 2H), 6.85(d, J = 7.5 Hz, 1H), 6.79(d, J = 7.5 Hz, 1H), 6.76(s, 1H), 4.65(s, 1H), 3.22(m, 4H), 2.66(s, 6H), 2.58(m, 4H); ESI-MS: m/z = 559[M + 1]⁺ |

Preparation Example 24. Synthesis of ethyl 4-(4-(N-(4-fluorophenyl) propanesulfonamido)-2-(trifluoromethyl)phenyl)piperazin-1-formate (Compound 49)

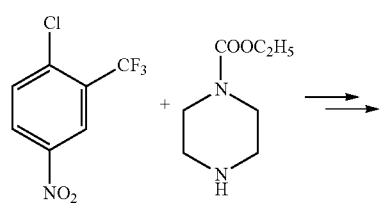

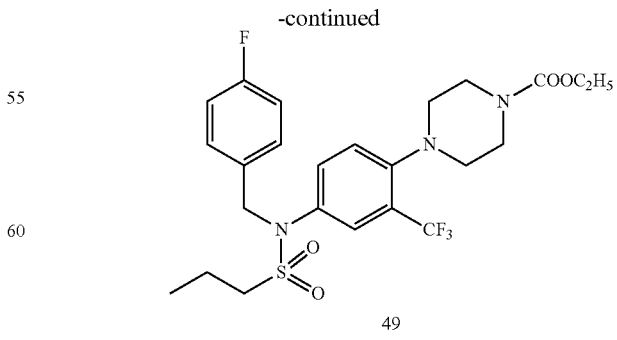

49

The synthesis was accomplished with reference to Steps 1-4 of Example 1, except that 1-chloro-4-nitro-2-(trifluoromethyl)benzene and corresponding monosubstituted piperazine were used as raw materials to prepare compound 49 via substitution, nitro reduction, reductive amination and sulfonamidation. $^1$H NMR (500 MHz, Chloroform-d): δ 7.64-7.61 (m, 2H), 7.25 (dd, J=8.8, 2.6 Hz, 2H), 6.87 (s, 1H), 6.56 (d, J=7.5 Hz, 1H), 6.49 (d, J=7.4 Hz, 1H), 4.63 (s, 2H), 4.15 (q, J=7.1 Hz, 2H), 3.32-3.29 (m, 8H), 3.15 (t, J=7.1 Hz, 2H), 1.70 (m, 2H), 1.30 (t, J=7.1 Hz, 3H), 0.91 (t, J=7.4 Hz, 3H); ESI-MS: m/z=532[M+1]$^+$.
Preparation Example 25. Synthesis of Compounds 50-58
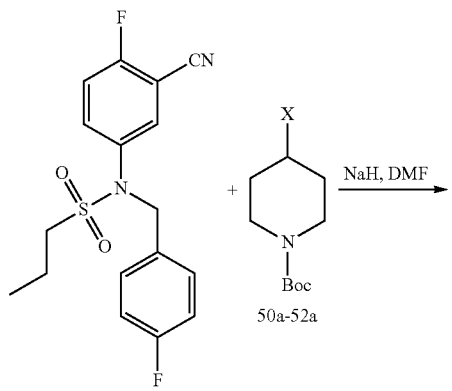
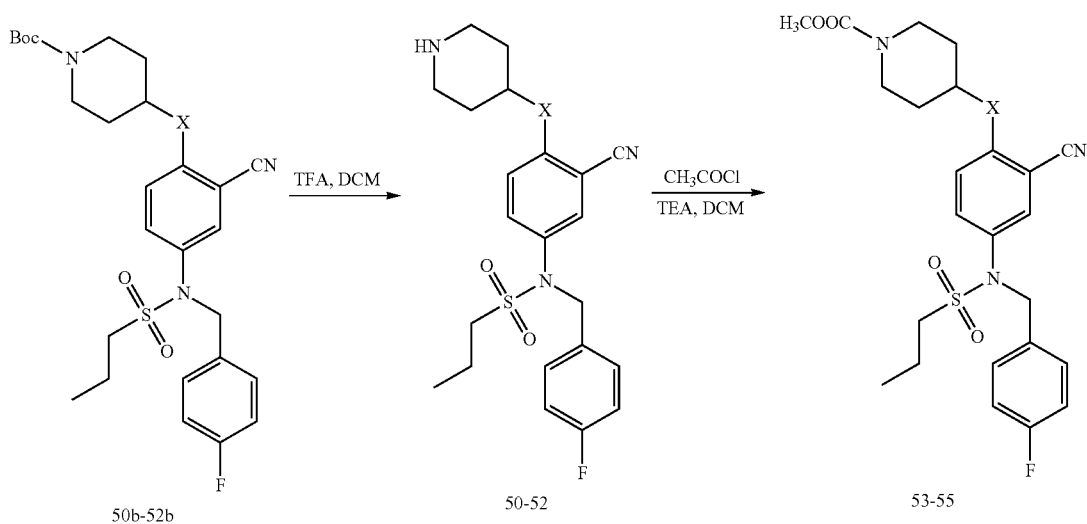

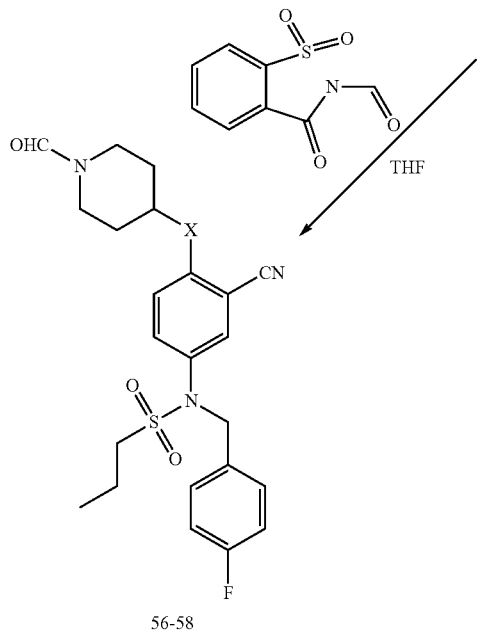

50a: X = OH, 51a: X = SH
52a: X = NH₂
50, 53, 56: X = O
51, 54, 57: X = S
52, 54, 58: X = NH

Compounds 50-58 were prepared using parallel synthesis method well-known to those skilled in the art. The starting material, N-(3-cyano-4-fluorophenyl)-N-(4-fluorobenzyl)propanesulfonamide, was prepared with reference to the synthesis procedure of 5b in Steps 1 and 2 of Preparation Example 5.

Step 1. Synthesis of Intermediates 50b-52b 50a-52a (2.5 mmol) were placed into three parallel reaction flasks, respectively, and were dissolved with anhydrous DMF. The resultant mixtures were each cooled to 0° C., to which 60% sodium hydride (0.12 g, 3.0 mmol) was added, and stirred for 0.5 h with the temperature maintained, and to which N-(3-cyano-4-fluorophenyl)-N-(4-fluorobenzyl)propanesulfonamide (1.0 g, 2.7 mmol) was further added, warmed to room temperature, and allowed for reaction for 1 h. After completion of the reaction, the reaction mixtures were each poured into water, extracted with ethyl acetate, washed with saturated saline, dried over anhydrous sodium sulfate, filtered, and concentrated under reduced pressure. The residues were each purified with silica gel column chromatography (PE:EA=2:1, v/v), to give 50b-52b.

Step 2. Synthesis of Compounds 50-52

Intermediates 50b-52b (1.5 mmol) were dissolved in 30 mL of DCM, respectively, to which trifluoroacetic acid (5.0 g, 43.1 mmol) was added, followed by stirring at room temperature for 1 h. The resultant mixtures were each alkalized with a sodium carbonate solution, extracted with dichloromethane, dried over anhydrous sodium sulfate, filtered, and concentrated under reduced pressure. The residues were each purified with silica gel column chromatography (DCM:MeOH=20:1, v/v), to give compounds 50-52.

Step 3. Synthesis of Compounds 53-55

50-52 (0.45 mmol) were dissolved in 5 mL of DCM, respectively, to which triethylamine (0.05 g, 0.49 mmol) and then acetyl chloride (0.053 g, 0.67 mmol) were added sequentially, followed by stirring at room temperature for 1 h, and then concentration under reduced pressure. The residues were each purified with silica gel column chromatography (DCM:MeOH=20:1, v/v), to give compounds 53-55.

Step 4. Synthesis of Compounds 56-58

N-formyl saccharin (0.047 g, 0.22 mmol) was added to 1 mL of THF, to which 50-52 (0.22 mmol) were then added, respectively, followed by stirring at room temperature for 15 min. The resultant mixtures were each alkalized with a sodium carbonate solution, extracted with ethyl acetate, dried over anhydrous sodium sulfate, filtered, and concentrated under reduced pressure. The residues were each purified with silica gel column chromatography (DCM:MeOH=20:1, v/v), to give compounds 56-58.

Preparation Example 26. Synthesis of Compounds 59 and 60

The synthesis was accomplished with reference to Steps 1-4 of Example 25, except that 5b was used as raw material to prepare compounds 59 and 60 via substitution, deprotection of Boc, and N-acetylation/formylation.

TABLE 1.3

NMR and MS data of Compounds 50-60

| Preparation Example compound No. | Name of compound | NMR and MS data |
| --- | --- | --- |
| Compound 50 | N-(3-cyano-4-(piperidin-4-yloxy)phenyl)-N-(4-fluorobenzyl)propanesulfonamide | $^1$HNMR (500 MHz, Chloroform-d): δ 7.63(dd, J = 7.5, 5.0 Hz, 2H), 7.32(d, J = 7.4 Hz, 1H), 7.25 (ddd, J = 8.0, 7.5, 1.5 Hz, 2H), 7.04(d, J = 7.4 Hz, 1H), 6.95(s, 1H), 4.56(s, 2H), 4.23(br, 1H), 3.70(m, 1H), 3.12(t, J = 7.2 Hz, 2H), 2.80-2.69(m, 4H), 2.00-1.75 (m, 4H), 1.68(m, 2H), 0.97(t, J = 7.2 Hz, 3H); ESI-MS: m/z = 432[M + 1]$^+$ |
| Compound 51 | N-(3-cyano-4-(piperidin-4-ylthio)phenyl)-N-(4-fluorobenzyl)propanesulfonamide | $^1$HNMR (500 MHz, Chloroform-d): δ 7.66(dd, J = 7.5, 5.0 Hz, 2H), 7.44(d, J = 7.5 Hz, 1H), 7.23(dd, J = 8.0, 7.5 Hz, 2H), 6.85-6.82(m, 2H), 4.63(s, 2H), 4.15(br, 1H), 3.11(t, J = 7.2 Hz, 2H), 2.89(m, 1H), 2.81-2.70(m, 4H), 1.99-1.74(m, 4H), 1.68(m, 1H), 1.01(t, J = 7.2 Hz, 3H); ESI-MS: m/z = 478[M + 1]$^+$ |
| Compound 52 | N-(3-cyano-4-(piperidin-4-ylamino)phenyl)-N-(4-fluorobenzyl)propanesulfonamide | $^1$HNMR (500 MHz, Chloroform-d): δ 7.56(dd, J = 7.5, 5.0 Hz, 2H), 7.22(dd, J = 8.0, 7.5 Hz, 2H), 6.85-6.82(m, 2H), 6.75(d, J = 7.5 Hz, 1H), 4.60(br, 1H), 4.53(s, 2H), 3.55(br, 1H), 3.10(t, J = 7.1 Hz, 2H), 2.79-2.63(m, 5H), 1.81-1.56(m, 6H), 0.97(t, J = 7.1 Hz, 3H),; ESI-MS: m/z = 431[M + 1]$^+$ |

TABLE 1.3-continued

NMR and MS data of Compounds 50-60

| Preparation Example compound No. | Name of compound | NMR and MS data |
|---|---|---|
| Compound 53 | N-(4-((1-acetylpiperidin-4-yl)oxy)-3-cyanophenyl)-N-(4-fluorobenzyl) propanesulfonamide 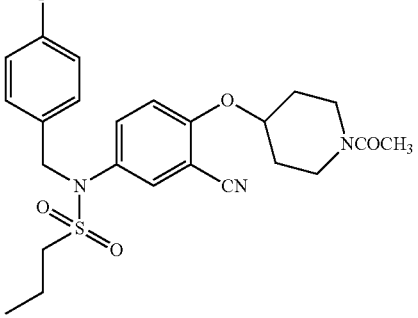 | $^1$HNMR (500 MHz, Chloroform-d): δ 7.63(dd, J = 7.5, 5.0 Hz, 2H), 7.38(d, J = 7.5 Hz, 1H), 7.22(dd, J = 8.0, 7.5 Hz, 2H), 7.04(d, J = 7.5 Hz, 1H), 6.92(s, 1H), 4.67(s, 2H), 3.76(m, 1H), 3.59-3.49(m, 4H), 3.11(t, J = 7.2 Hz, 2H), 2.15-1.90(m, 4H), 2.10(s, 3H), 1.68(m, 2H), 0.98(t, J = 7.2 Hz, 3H); ESI-MS: m/z = 474[M + 1]$^+$ |
| Compound 54 | N-(4-((1-acetylpiperidin-4-yl)thio)-3-cyanophenyl)-N-(4-fluorobenzyl) propanesulfonamide 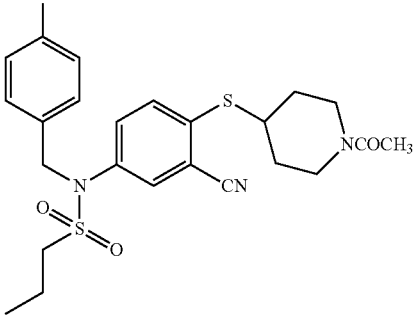 | $^1$HNMR (500 MHz, Chloroform-d): δ 7.65(dd, J = 7.5, 5.0 Hz, 2H), 7.44(d, J = 7.5 Hz, 1H), 7.21(dd, J = 8.0, 7.5 Hz, 2H), 6.88(d, J = 7.5 Hz, 1H), 6.82(s, 1H), 4.66(s, 2H), 3.59-3.49(m, 4H), 3.11(t, J = 7.2 Hz, 2H), 2.94(m, 1H), 2.13-1.88(m, 4H), 2.11(s, 3H), 1.69(m, 2H), 1.69(m, 2H), 1.00(t, J = 7.2 Hz, 3H); ESI-MS: m/z = 490[M + 1]$^+$ |
| Compound 55 | N-(4-((1-acetylpiperidin-4-yl) amino)-3-cyanophenyl)-N-(4-fluorobenzyl)propanesulfonamide 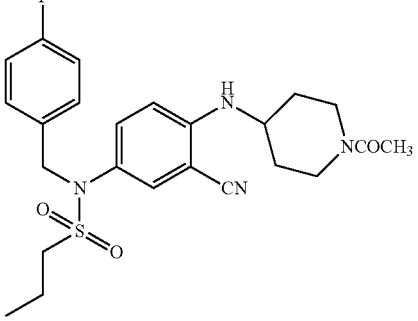 | $^1$HNMR (500 MHz, Chloroform-d): δ 7.60(dd, J = 7.5, 5.0 Hz, 2H), 7.23(dd, J = 8.0, 7.5 Hz, 2H), 6.85-6.82(m, 2H), 6.75(d, J = 7.5 Hz, 1H), 4.71 (br, 1H), 4.62(s, 2H), 3.60-3.50(m, 4H), 3.09(t, J = 7.1 Hz, 2H), 2.68(m, 1H), 2.10(s, 3H), 1.97-1.72 (m, 6H), 0.98(t, J = 7.2 Hz, 3H); ESI-MS: m/z = 473[M + 1]$^+$ |

TABLE 1.3-continued

NMR and MS data of Compounds 50-60

| Preparation Example compound No. | Name of compound | NMR and MS data |
|---|---|---|
| Compound 56 | N-(4-((1-formylpiperidin-4-yl)oxy)-3-cyanophenyl)-N-(4-fluorobenzyl)propanesulfonamide 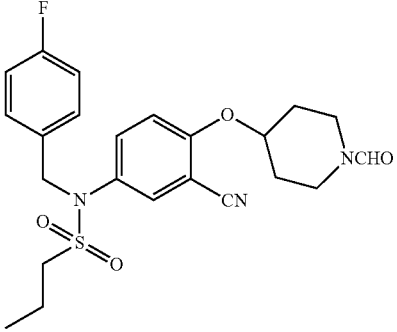 | $^1$HNMR (500 MHz, Chloroform-d): δ 8.05(s, 1H), 7.59(dd, J = 7.5, 5.0 Hz, 2H), 7.32(d, J = 7.5 Hz, 1H), 7.22(dd, J = 8.0, 7.5 Hz, 2H), 4.62(s, 2H), 3.76(m, 1H), 3.59-3.48(m, 4H), 3.10(t, J = 7.1 Hz, 2H), 2.15-1.90(m, 4H), 1.68(m, 1H), 0.96(t, J = 7.1 Hz, 3H); ESI-MS: m/z = 460[M + 1]$^+$ |
| Compound 57 | N-(4-((1-formylpiperidin-4-yl)thio)-3-cyanophenyl)-N-(4-fluorobenzyl)propanesulfonamide 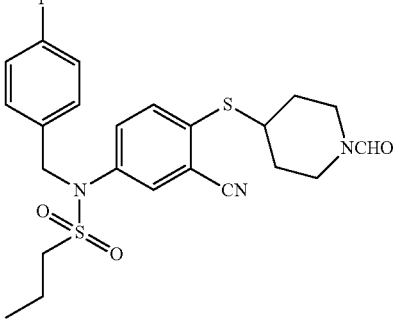 | $^1$HNMR (500 MHz, Chloroform-d): δ 8.04(s, 1H), 7.63(dd, J = 7.5, 5.0 Hz, 2H), 7.44(d, J = 7.5 Hz, 1H), 7.38(dd, J = 8.0, 7.5 Hz, 2H), 6.85-6.83(m, 2H), 4.66(s, 2H), 3.60-3.51(m, 4H), 3.12(t, J = 7.2 Hz, 2H), 2.95(m, 1H), 2.14-1.89(m, 4H), 1.70(m, 2H), 1.00(t, J = 7.2 Hz, 3H); ESI-MS: m/z = 476[M + 1]$^+$ |
| Compound 58 | N-(4-((1-formylpiperidin-4-yl)amino)-3-cyanophenyl)-N-(4-fluorobenzyl)propanesulfonamide 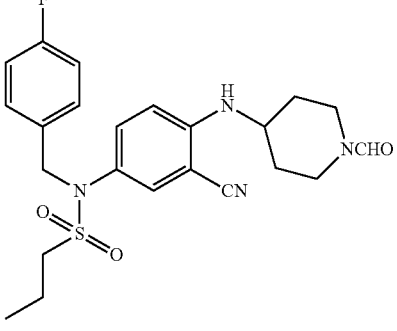 | $^1$HNMR (500 MHz, Chloroform-d): δ 8.08(s, 1H), 7.65(dd, J = 7.5, 4.9 Hz, 2H), 7.25(dd, J = 8.0, 7.5 Hz, 2H), 6.84-6.83(m, 2H), 6.75(d, J = 7.5 Hz, 1H), 4.67(s, 2H), 4.55(br, 1H), 3.59-3.50(m, 4H), 3.12(t, J = 7.1 Hz, 2H), 2.68(m, 1H), 1.97-1.73(m, 6H), 0.95(t, J = 7.1 Hz, 3H); ESI-MS: m/z = 459[M + 1]$^+$ |

TABLE 1.3-continued

NMR and MS data of Compounds 50-60

| Preparation Example compound No. | Name of compound | NMR and MS data |
|---|---|---|
| Compound 59 | N-(4-((1-acetylpiperidin-4-yl)oxy)-3-cyanophenyl)-N-benzylbenzenesulfonamide | $^{1}$HNMR (500 MHz, Chloroform-d): δ 7.71-7.65 (m, 3H), 7.57 (t, J =7.8 Hz, 2H), 7.27-7.18 (m, 6H), 7.05 (d, J = 2.6 Hz, 1H), 6.81 (d, J = 9.1 Hz, 1H), 4.68 (s, 2H), 4.66-4.61 (m, 1H), 3.91-3.81 (m, 1H), 3.75-3.67 (m, 1H), 3.64-3.54 (m, 1H), 3.54-3.43 (m, 1H), 2.13 (s, 3H), 1.94-1.83 (m, 4H); ESI-MS: m/z = 490[M + 1]$^+$ |
| Compound 60 | N-(4-((1-formylpiperidin-4-yl)oxy)-3-cyanophenyl)-N-benzylbenzenesulfonamide | $^{1}$H NMR (500 MHz, Chloroform-d): δ 8.06 (s, 1H), 7.71-7.65 (m, 3H), 7.57 (t, J = 7.8 Hz, 2H), 7.28-7.22 (m, 4H), 7.22-7.19 (m, 2H), 7.06 (d, J = 2.6 Hz, 1H), 6.82 (d, J = 9.1 Hz, 1H), 4.72-4.69 (m, 1H), 4.68 (s, 2H), 3.89-3.76 (m, 1H), 3.69-3.61 (m, 1H), 3.58-3.48 (m, 1H), 3.43-3.36 (m, 1H), 1.99-1.84 (m, 4H); ESI-MS: m/z = 476[M + 1]$^+$ |

Preparation Example 27. Synthesis of ethyl 4-(4-(N-benzylpropane sulfonamido)2-cyanophenyl)-3-oxopiperazin-1-formate (Compound 61)

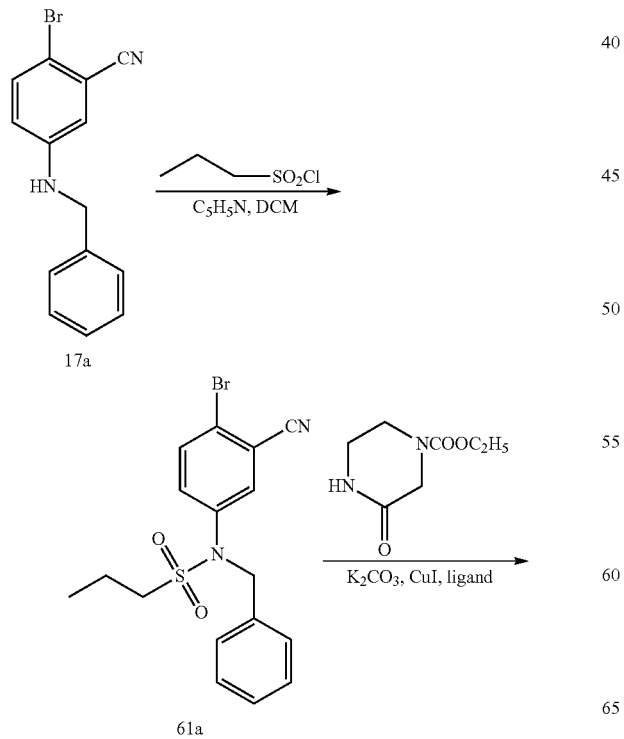

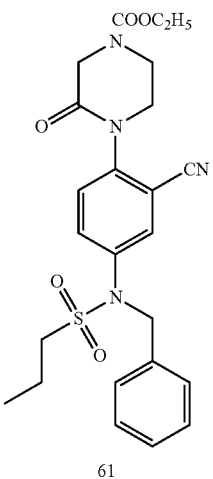

Step 1. Synthesis of intermediate N-benzyl-N-(4-bromo-3-cyanophenyl)propanesulfonamide (61a)

The synthesis was accomplished with reference to Step 2 of Example 17, except that 17a and propane sulfonyl chloride were used as raw materials to prepare compound 61a, ESI-MS: m/z=394[M+1]$^+$.

Step 2. Synthesis of ethyl 4-(4-(N-benzylpropane-sulfonamido)2-cyano phenyl)-3-oxopiperazin-1-formate (Compound 61)

The synthesis was accomplished with reference to Step 3 of Example 17, except that 61a and ethyl 3-oxopiperazin-1-formate were used as raw materials to prepare compound 61. $^1$H NMR (500 MHz, Chloroform-d): δ 7.43 (d, J=7.5 Hz, 2H), 7.31-7.29 (m, 3H), 7.25 (d, J=7.5 Hz, 2H), 7.21 (d, J=7.5 Hz, 1H), 6.97 (s, 1H), 4.65 (s, 2H), 4.14 (q, J=7.1 Hz, 2H), 3.79 (s, 2H), 3.64 (t, J=7.1 Hz, 2H), 3.24 (t, J=7.1 Hz, 2H), 3.10 (t, J=7.1 Hz, 2H), 1.70 (m, 2H), 1.22 (t, J=7.2 Hz, 3H), 0.99 (t, J=7.2 Hz, 3H); ESI-MS: m/z=485[M+1]$^+$.

Example 28 Biological Assessments

I. IonWorks Automated Patch Clamp Assay of Inhibitory Activity Against Kv1.3

The principle and method for Kv1.3 IonWorks assay can be found in Schroeder et al. [Schroeder et al. J Biomol Screen 2003, 8(1):50-64]

1. Cell Culture

Inhibitory activity of the compounds against Kv1.3 was assessed using a CHO-K1 recombinant cell line stably expressing human Kv1.3 (Charles River, Calif.). The cells were cultured in an F-12K culture medium containing 5% calf serum (Invitrogen, Carlsbad. Calif.) in an incubator at 37° C. and under air humidity with 6% $CO_2$. Prior to be fed in the IonWorks system, the adherent cells were treated with Versene at 37° C. for 6-7 min. After gently beating the culture flask, the cells were re-suspended in a PBS phosphate buffer, and then were centrifuged at 50×g for 4 min. After a short grinding, the cells were eventually re-suspended in an external recording solution at a density of approximately 1×10$^6$/mL.

2. Preparation of Plates for Assay of Compounds

The compounds were dissolved in DMSO to formulate a final assay concentration of 300× on the master plate. The final gradient assay concentrations were 0.00384, 0.00192, 0.096, 0.048, 0.24, 1.2, 6 and 30 μM. All 300× stock solutions of each compound in DMSO were transferred to a 384-well plate with 2 μl per well. The plates were sealed and stored at −80° C. until the day of assay.

On the day of assay, the plates were each thawed at room temperature. After centrifugation, 198 μl of the external recording solution (with the components of: 130 mM Na-Gluconate, 20 mM NaCl, 4 mM KCl, 1 mM $MgCl_2$, 1.8 mM $CaCl_2$, 5 mM Glucose and 10 mM HEPES, pH7.3) was added and mixed thoroughly. This step provided a 1:100 dilution for the compounds. After addition of cells to IonWorks, a further 1:3 dilution was carried out, resulting in a total dilution of 1:300. At least 8 wells were reserved as blank control on each of the plates, i.e., containing only 0.3% DMSO. In addition, at least 8 wells were reserved as positive control to detect the specificity to cell signals. Fluoxetine, a compound as the positive control, was assayed at its maximum blocking concentration (100 μm) and secondary maximum blocking concentration (10 μm). In addition, an internal recording solution used in the assay (with the components of: 100 mM K-gluconate, 40 mM KCl, 1 mM $MgCl_2$, 1 mM EGTA and 10 mM HEPES, pH7.3) contained Amphotericin B at a final concentration of 200 μg/mL to gain current channels inside the cells. The osmotic pressure of the solution was adjusted with sucrose.

3. Experimental Procedures and Data Analysis

Experimental procedures were carried out following the protocols as set by IonWorks Quattro system (Molecular Devices, San Jose, CA). The current of human Kv1.3 was elicited to 0 millivolt (mV) for four times by a pulse lasting 1 second. A potential of −80 mV was maintained between pulses, for 5 seconds. First, a early voltage application program was started in the IonWorks Quattro system, and then the compounds were added and incubated for 600 seconds. Next, a late voltage application program was started until completion of all assays.

The maximum peak outward currents both before and after addition of the compounds as well as the average tail current elicited when the fourth pulse rose to 0 mV were measured. The inhibitory activity of the compounds against Kv1.3 can be calculated by dividing the measured current amplitude after addition of the compounds by the measured current amplitude before addition of the compounds.

All data was calibrated by a data filtration program of the IonWorks Quattro system. The filtration standard was that: seal quality >30 MΩ, decrease of seal resistance <50% and current amplitude >200 pA.

TABLE 2.1

The inhibitory activity of compounds against Kv1.3 (automated patch clamp method)

| Compound No. | Kv1.3 (IC$_{50}$, μM) |
|---|---|
| 1 | 0.265 |
| 2 | 0.131 |
| 3 | 0.107 |
| 4 | 12.90 |
| 5 | 0.186 |
| 6 | 0.193 |
| 7 | 0.312 |
| 8 | 9.301 |
| 9 | 0.134 |
| 10 | 0.098 |
| 11 | 0.195 |
| 12 | 0.234 |
| 13 | 6.400 |
| 14 | 0.129 |
| 15 | 0.310 |
| 16 | 1.260 |
| 17 | 0.190 |
| 18 | 0.101 |
| 19 | 0.130 |
| 20 | 0.090 |
| 21 | 0.097 |
| 22 | 0.333 |
| 23 | 0.176 |
| 24 | 0.086 |
| 25 | 0.321 |
| 26 | 0.420 |
| 27 | 0.239 |
| 28 | 0.676 |
| 29 | 0.439 |
| 30 | 0.288 |
| 31 | 0.412 |
| 32 | 0.165 |
| 33 | 0.839 |
| 34 | 0.645 |
| 35 | 0.201 |
| 36 | 0.130 |
| 37 | 0.092 |
| 38 | 0.101 |
| 39 | 0.155 |
| 40 | 0.206 |
| 41 | 0.131 |
| 42 | 0.167 |
| 43 | 0.124 |
| 44 | 0.096 |
| 45 | 0.224 |
| 46 | 0.356 |
| 47 | 0.124 |
| 48 | 0.145 |
| 49 | 0.160 |

TABLE 2.1-continued

The inhibitory activity of compounds against
Kv1.3 (automated patch clamp method)

| Compound No. | Kv1.3 (IC$_{50}$, μM) |
|---|---|
| 50 | 0.370 |
| 51 | 0.412 |
| 52 | 0.139 |
| 53 | 0.291 |
| 54 | 0.389 |
| 55 | 0.160 |
| 56 | 0.250 |
| 57 | 0.254 |
| 58 | 0.279 |
| 59 | 0.441 |
| 60 | 0.332 |
| 61 | 0.092 |

II. Conventional Patch Clamp Assay of Inhibitory Activity Against Kv1.3

In order to compare the influence of different assay methods on the inhibitory activity of a compound, the conventional patch clamp method was used to assay the inhibitory activities of compounds 21, 37, 44, 61 against Kv1.3. The principle and method for the conventional patch clamp method can be found in Grissmer et al. [Grissmer et al. Molecular Pharmacology 1994, 45:1227-1234].

1. Cell Culture

Inhibitory activity of the compounds against Kv1.3 was assessed using a CHO-K1 recombinant cell line stably expressing human Kv1.3 (Charles River, California). The cells were cultured in an F-12K culture medium containing 5% calf serum (Invitrogen, Carlsbad.ca) in an incubator at 37° C. and under air humidity with 6% $CO_2$.

During the experiment, adherent cells were placed in a recording chamber under an inverted microscope. All the experiments were performed at room temperature. Each of the cells used itself as the control.

2. Assay of the Compounds

The test compounds were formulated to their final concentrations on the day of assay, and then dissolved in an extracellular fluid. The extracellular fluid (mM) was: NaCl, 137; KCl, 4; $CaCl_2$, 1.8; $MgCl_2$, 1; HEPES, 10; glucose 10; pH 7.4 (NaOH titration). All the solutions of the test compounds and the control compounds contained 0.3% of DMSO.

Each of the compounds was perfused by a gravity-driven perfusion system. At least two cells were tested for each of the concentrations of a compound. After the current was stable, the blocking effect of the compounds was calculated by comparing the change in the current before and after administration of the compounds. 1000 μM 4-AP was used as a positive control.

3. Electrophysiology

The cells were transferred to a perfusion chamber, and were perfused with the extracellular fluid. Intracellular fluid (mM): K-aspartate, 130; $MgCl_2$, 5; EGTA 5; HEPES, 10; pH 7.2 (KOH titration). The intracellular fluid was stored in a small amount in a refrigerator at −80° C. in batches, and was thawed on the day of the experiment. The electrodes were drawn by PC-10 (Narishige, Japan). A whole-cell patch-clamp recording was performed, with the noise being filtered by one-fifth of the sampling frequency.

4. Process of Assay and Analysis of Results

The cells were clamped at −80 mV and then depolarized to 0 mV with square waves lasting for 2 seconds to obtain a Kv1.3 current. This process was repeated every 20 seconds. The maximum current elicited by the square waves was detected. After the maximum current became stable, the test compounds were perfused. After the reaction was stable, the blocking strength was calculated.

Data was collected and analyzed using pCLAMP 10 (Molecular Devices, Union City, CA). A stable current meant a current which varies within a limited range over time. The value of the stable current was used to calculate the effect of a compound at this solubility.

TABLE 2.2

Inhibitory activity of certain compounds against
Kv1.3 (conventional patch-clamp method)

| Compound No. | Kv1.3 (IC$_{50}$, μM) |
|---|---|
| 21 | 0.141 |
| 37 | 0.108 |
| 44 | 0.111 |
| 61 | 0.130 |

III. Conventional Patch Clamp Assay of Inhibitory Activity Against Kv1.5

The principle and method for the conventional patch clamp method can be found in Grissmer et al. [Grissmer et al. Molecular Pharmacology 1994, 45:1227-1234].

1. Cell Culture

Inhibitory activity of a compounds against Kv1.5 was assessed using a CHO-K1 recombinant cell line stably expressing human Kv1.5 (Charles River, Calif.). The cells were cultured in an F-12K culture medium containing 5% calf serum (Invitrogen, Carlsbad.ca) in an incubator at 37° C. and under air humidity with 6% $CO_2$.

During the experiment, adherent cells were placed in a recording chamber under an inverted microscope. All the experiments were performed at room temperature. Each of the cells used itself as the control.

2. Assay of the Compounds

The test compounds were formulated to their final concentrations on the day of assay, and then dissolved in an extracellular fluid. The extracellular fluid (mM) was: NaCl, 137; KCl, 4; $CaCl_2$, 1.8; $MgCl_2$, 1; HEPES, 10; glucose 10; pH 7.4 (NaOH titration). All the solutions of the test compounds and the control compounds contained 0.3% of DMSO.

Each of the compounds was perfused by a gravity-driven perfusion system. At least two cells were tested for each of the concentrations of a compound. After the current was stable, the blocking effect of the compounds was calculated by comparing the change in the current before and after administration of the compounds.

1000 μM 4-AP was used as a positive control.

3. Electrophysiology

The cells were transferred to a perfusion chamber, and were perfused with the extracellular fluid. Intracellular fluid (mM): K-aspartate, 130; $MgCl_2$, 5; EGTA 5; HEPES, 10; pH 7.2 (KOH titration). The intracellular fluid was stored in a small amount in a refrigerator at −80° C. in batches, and was thawed on the day of the experiment. The electrodes were drawn by PC-10 (Narishige, Japan). A whole-cell patch-clamp recording was performed, with the noise being filtered by one-fifth of the sampling frequency.

4. Process of Assay and Analysis of Results

The cells were clamped at −80 mV and then depolarized to 20 mV with square waves lasting for 2 seconds to obtain a Kv1.5 current. This process was repeated every 20 seconds. The maximum current elicited by the square waves was detected. After the maximum current became stable, the test compounds were perfused. After the reaction was stable, the blocking strength was calculated.

Data was collected and analyzed using pCLAMP 10 (Molecular Devices, Union City, CA). A stable current meant a current which varies within a limited range over time. The value of the stable current was used to calculate the effect of a compound at this solubility.

TABLE 2.2

Inhibitory activity of certain compounds against Kv1.5 (conventional patch-clamp method)

| Compound No. | Kv1.5 ($IC_{50}$, µM) |
|---|---|
| 21 | 2.816 |
| 37 | 3.65 |
| 44 | 7.895 |
| 61 | 2.108 |

IV. Effects of Compound 37 on a Rat Model of Allergic Contact Dermatitis (ACD Model)
1. Laboratory Animal
   SPF SD female rats with body weight of 130-150 g were used.
2. Drugs and Agents
   Dexamethasone (DXMS) sodium phosphate injection, 5 mg/ml/injection (Shiyao Yinhu Pharmaceutical Co., Ltd.); 1-chloro-2,4-dinitrobenzene (DNCB) (TCI Shanghai); vehicle and negative control: acetone/DMSO 9:1 (Vehicle, Model group).
3. Experimental Procedures
   3.1 The animals were randomly divided into 6 groups based on body weight with 10 animals per group: blank control group, model control group, positive control group (dexamethasone sodium phosphate injection 5 mg/mL), 5% Compound 37 group, 1.5% Compound 37 group and 0.5% Compound 37 group.
   3.2 Modeling and administration: a rat model of allergic contact dermatitis (ACD) was established by sensitizing and stimulating the rat's skin with a DNCB solution in acetone and DMSO (acetone-DMSO 9:1). The rats were normally fed in a SPF barrier system for 1 week. Long hair was removed with a razor and short hair was removed with depilatory cream within an area of about 2 cm×2 cm from abdomen of the rats one day before the experiment. On day 1 of the experiment, the depilation site was uniformly applied with 50 µL of 7% DNCB solution in acetone and DMSO for sensitization. On day 2 of the experiment, 50 µL of 1% DNCB solution in acetone and DMSO was used repeatedly to strengthen the sensitization. From day 5 of the experiment, for each of the rats, the right ear was stimulated by applying 20 µL of 1% DNCB solution in acetone and DMSO, and the left ear was stimulated by applying 20 µL of acetone-DMSO (acetone-DMSO 9:1) solution as the control; for the negative control group, the same site was only applied with 20 µL of acetone-DMSO solution (9:1) as the control, for 3 days. An ACD rat model induced by DNCB was established in rats with manifest erythema and swelling in ears. The drugs were administered to the right ear by wiping. The first administration was 6~8 h before stimulation. After the stimulation, the drugs were administered by wiping three times a day, with 25 µl each time, for 4 days. For the negative control group and the model control group, a blank medium of equal volume was administered to the right ear of the rats by wiping.
   3.3 Measurement of difference between ear thicknesses: before the stimulation and after the final administration, the thickness of central parts of left and right ears of the rats in each of the groups was measured with electronic digital calipers. The measurements were performed twice in parallel and averaged to calculate the difference between ear thicknesses (right ear thickness−left ear thickness).
4. Conclusion: Compound 37 significantly reduced ear inflammation in rats with atopic dermatitis (ACD) in a dose-dependent manner. The experimental results were shown in FIG. 1.

V. Effects of Compound 24 on a Rat Model of Psoriasis Induced by Imiquimod
1. Laboratory Animal
   SPF Wista female rats with body weight of around 200 g were used.
2. Drugs and Formulations
   Dexamethasone (DXMS) sodium phosphate injection, 5 mg/ml/injection (Shiyao Yinhu Pharmaceutical Co., Ltd.); 5% imiquimod cream, 0.25 g/pack (Sichuan MED-SHINE Pharmaceutical Co., Ltd.); $3\times10^6$ U recombinant human interferon α-2a injection, 1.0 ml/vial (Shenyang Sunshine Pharmaceutical Co., Ltd.); vehicle and negative control: acetone/DMSO 9:1 (Vehicle).
3. Experimental Procedures
   3.1 The animals were randomly divided into 6 groups based on body weight with 10 animals per group: normal control group, model control group, positive control group (dexamethasone sodium phosphate injection 5 mg/mL), 1% Compound 24 group, 0.3% Compound 24 group and 0.1% Compound 24 group.
   3.2 Modelling and administration: after adaptive feeding for several days, for each of the rats, hair in central area of the back (2 cm×2 cm) was shaved, and then the surface short hair was shaved with mild depilatory cream, washed and dried. If hair on the back grew out again during the experiment, the hair was removed with a razor. Every morning, for the rats in model control group and administration groups, 5% imiquimod cream was evenly applied on the back at 20 mg/cm² (0.25 g/pack, for 3 rats), and after 10 min, recombinant human interferon α-2a injection was injected intraperitoneally at 10,000 U/500 g; for the normal control group, the rats were not treated, once a day, for 10 days. In the afternoon, for the rats in the administration groups, drugs were applied at a corresponding dose (drugs with corresponding concentrations were applied on the back at 100 µL/rat, twice, 50 µL each time) once a day for 10 days.
   3.3 Psoriasis Area and Severity Index (PASI) score: according to PASI scoring standard, a score of 0-4 was given for erythema, scale and epidermal thickening of infiltration in the lesional skin of rats. The scoring criteria was as follows: 0, none; 1, mild; 2, moderate; 3, severe; 4, extremely severe. For the rats in each of the groups, the scores were averaged and changes in skin lesions of the rats were observed.
   3.4 HE staining: after completion of modeling (on day 11), the tissues with skin lesions on the back of rats were collected, fixed with 4% neutral formaldehyde, embedded in paraffin, and sectioned. After HE staining, changes in skin histomorphology were observed under a microscope, and Baker scoring was performed. The specific criteria for Baker scoring were as follows: Munro's microabscess as found in the epidermis: a score of 2.0; hyperkeratosis: a score of 0.5; parakeratosis: a score of 1.0; thinning or disappearing of the granular layer: a score of 1.0; acanthosis: a score of 1.0;

mild, moderate and severe lengthening and clubbing of rete ridges: scores of 0.5, 1.0 and 1.5, respectively; mild, moderate and severe infiltration of mononuclear or multinuclear cells in the dermis: scores of 0.5, 1.0 and 1.5, respectively; thinning above papillae: a score of 0.5; capillarectasis: a score of 0.5.

3.5 Statistical Methods: all data was expressed as mean±standard deviation (x±s). SPSS 20.0 statistical software was used to process the data. One-way ANOVA was used to compare the mean values of multiple samples. P<0.05 was considered statistically significant. A rank sum test was used for the data that is not normally distributed or of unequal variance.

Figure 2:
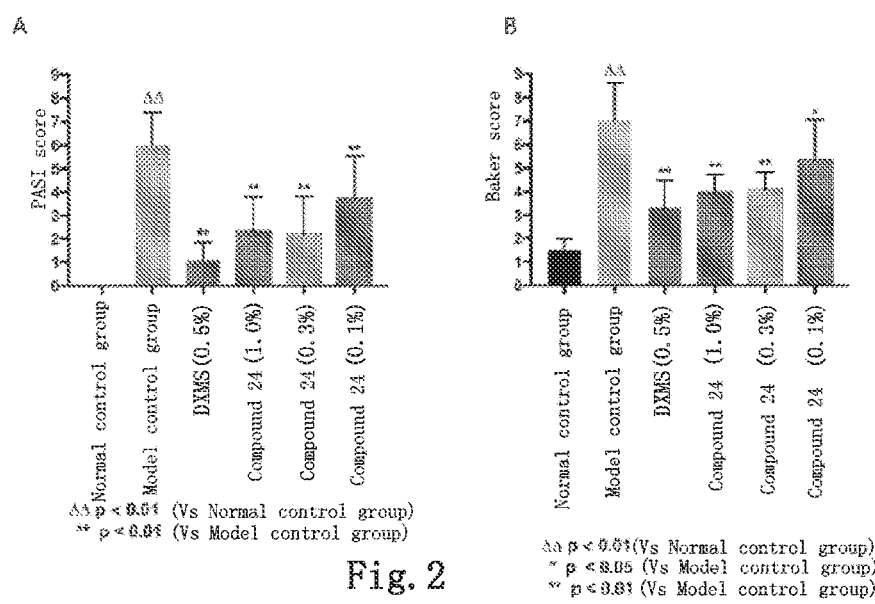
FIG. 2 is a graph showing the effect of compound 24 on a rat model of imiquimod induced psoriasis. Figure A shows the result of PASI score and Figure B shows the result of Baker score. Compound 24 exhibited a significant efficacy on psoriasis in a dose-dependent manner.
Figure 3:
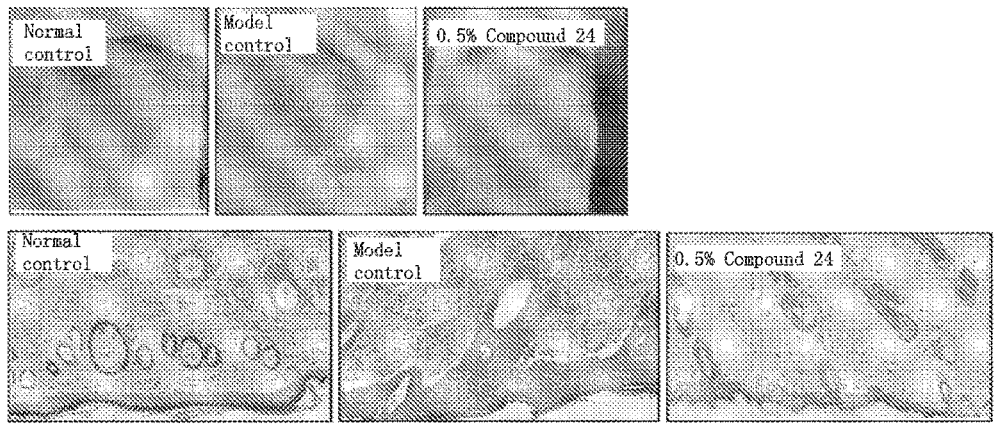
FIG. 3 is a graph showing the pathological analysis of the effect of compound 24 on a rat model of psoriasis (HE×100), in which 1) in the normal control group, the skin structure was intact and clear, without hyperkeratosis, acanthosis, capillarectasis, and with a small amount of infiltration of inflammatory cells in the dermis; 2) in the model control group, it was observed that the granular layer thinned or even disappeared, with acanthosis, thinning above papillae, and a large amount of infiltration of inflammatory cells in the dermis; 3) in the groups of compound 24, the skin structure was intact, the granular layer was visible, the skin was partly lengthened and clubbed, no acanthosis was observed, and a small amount infiltration of inflammatory cells was observed in the dermis.

4. Conclusion: all the results of PASI and Baker scores, and pathological analysis demonstrated that Compound 24 had a significant effect on psoriasis in a dose-dependent manner. The experimental results were shown in FIGS. 2 and 3.

What is claimed is:

1. An N-benzyl-N-arylsulfonamide derivative, characterized in that it is an N-benzyl-N-arylsulfonamide compound represented by formula (I) or a pharmaceutically acceptable salt or solvate thereof

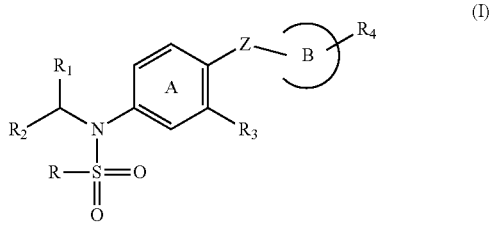

(I)

wherein:
ring A is a benzene ring;
ring B is selected from the group consisting of:

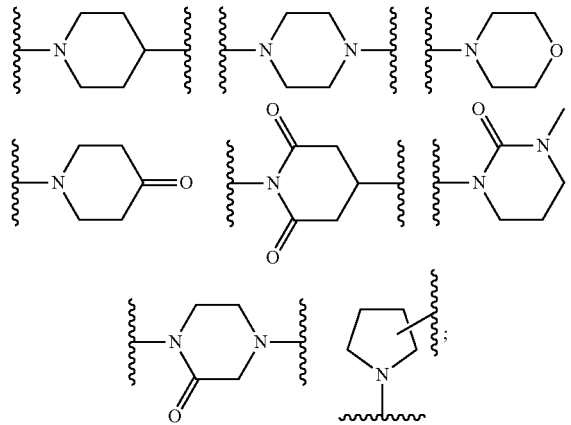

R is selected from the group consisting of C1-6 linear or branched alkyl and halogenated C1-6 linear or branched alkyl;
$R_1$ is selected from the group consisting of substituted or unsubstituted phenyl, and 5- or 6-membered substituted or unsubstituted heteroaryl containing 1-3 heteroatoms selected from the group consisting of O, N and S, the substitution being mono-, di- or tri-substitution with the substituent group being Rb group;

Rb is selected from the group consisting of H, halogen, nitro, cyano, C1-3 alkyl, C1-3 alkoxy, halogenated C1-3 alkyl and —C—O—C—;
$R_2$ is selected from the group consisting of H, C1-3 linear or branched alkyl, cyclopropyl and =O;
$R_3$ is selected from the group consisting of halogen, nitro, cyano, trifluoromethyl, amido, and substituted alkylamido;
$R_4$ is selected from the group consisting of H, halogen, =O, OH, $NH_2$, formate group, carbamate group, alkylacyl, acetate group, sulfonamido, pyrrolidonyl, cyclopropyl, aminoformamido, dimethylaminoethoxy, alkanoyloxy and alkylamido; and
Z is selected from the group consisting of O, S and NH, or is absent.

2. An N-benzyl-N-arylsulfonamide derivative selected from the group consisting of the following compounds:
ethyl 4-(2-cyano-4-(N-(4-fluorobenzyl)propanesulfonamido)phenyl) piperazin-1-formate,
N-(3-cyano-4-(4-hydroxypiperidin-1-yl)phenyl)-N-(4-fluorobenzyl) propane-1-sulfonamide,
4-(2-cyano-4-(N-(4-fluorobenzyl)propyl)phenyl)-N,N-dimethyl piperazin-1-formamide,
ethyl 4-(4-(N-benzylpropanesulfonamido)2-cyanophenyl)piperazin-1-formate,
ethyl 4-(2-cyano-4-(N-(3-fluorobenzyl)propanesulfonamido)phenyl) piperazin-1-formate,
ethyl 4-(4-(4-(N-(4-chlorobenzyl)propanesulfonamido)2-cyanophenyl) piperazin-1-formate,
ethyl 4-(2-cyano-4-(N-(2-fluorobenzyl)propanesulfonamido)phenyl) piperazin-1-formate,
ethyl 4-(2-cyano-4-(N-(3-methoxybenzyl)propanesulfonamido)phenyl) piperazin-1-formate,
ethyl 4-(2-cyano-4-(N-(4-methoxybenzyl)propanesulfonamido)phenyl) piperazin-1-formate,
ethyl 4-(2-cyano-4-(N-(3,4-dimethoxybenzyl)propanesulfonamido)phenyl)piperazin-1-formate,
ethyl 4-(2-cyano-4-(N-(2-fluoro-4-methoxybenzyl) propanesulfonamido)phenyl)piperazin-1-formate,
ethyl 4-(2-cyano-4-(N-(4-fluoro-2-methoxybenzyl) propanesulfonamido)phenyl)piperazin-1-formate,
ethyl 4-(2-cyano-4-(N-(pyrimidin-4-ylmethyl)propanesulfonamido) phenyl)piperazin-1-formate,
ethyl 4-(2-cyano-4-(N-(pyridin-2-ylmethyl)propanesulfonamido) phenyl)piperazin-1-formate,
ethyl 4-(2-cyano-4-(N-(furan-2-ylmethyl)propanesulfonamido)phenyl) piperazin-1-formate,
ethyl 4-(2-cyano-4-(N-(thiazol-4-ylmethyl)propanesulfonamido) phenyl)piperazin-1-formate,
ethyl 4-(2-cyano-4-(N-((1-methyl-1H-imidazol-5-yl) methyl) propanesulfonamido)phenyl)piperazin-1-formate,
ethyl 4-(2-cyano-4-(N-((1-methyl-1H-pyrazol-5-yl) methyl) propanesulfonamido)phenyl)piperazin-1-formate,
4-(2-cyano-4-((N-(4-fluorobenzyl)-2-methylpropyl) sulfonamido) phenyl)-N,N-dimethylpiperazin-1-formamide,
4-(2-cyano-4-(N-(4-fluorobenzyl)butanesulfonamido) phenyl)-N,N-dimethylpiperazin-1-formamide,
4-(2-cyano-4-((N-(4-fluorobenzyl)-3-methylbutyl)sulfonamido)phenyl)-N,N-dimethylpiperazin-1-formamide,
4-(2-cyano-4-((N-(4-fluorobenzyl)-2,2-dimethylpropyl) sulfonamido) phenyl)-N,N-dimethylpiperazin-1-formamide,
4-(2-cyano-4-(N-(pyridin-4-ylmethyl)propanesulfonamido)phenyl)-N,N-dimethylpiperazin-1-formamide, 4-(2-cyano-4-(N-(pyrimidin-4-ylmethyl)propanesulfonamido)phenyl)-N,N-dimethylpiperazin-1-formamide,
4-(2-cyano-4-(N-(4-fluorobenzyl)ethanesulfonamido)phenyl)-N,N-dimethylpiperazin-1-sulfonamide,
4-(4-(N-(4-chlorobenzyl)propanesulfonamido)-2-cyanophenyl)-N,N-dimethylpiperazin-1-sulfonamide,
4-(2-cyano-4-(N-(4-methoxybenzyl)propanesulfonamido)phenyl)-N,N-dimethylpiperazin-1-sulfonamide,
4-(2-cyano-4-((1-cyclopropyl-N-(2,4-difluorobenzyl)methyl) sulfonamido)phenyl)-N,N-dimethylpiperazin-1-sulfonamide,
ethyl 4-(4-(N-(4-fluorophenyl)propanesulfonamido)-2-(trifluoro methyl)phenyl)piperazin-1-formate,
N-(3-cyano-4-(piperidin-4-yloxy)phenyl)-N-(4-fluorobenzyl)propane sulfonamide,
N-(3-cyano-4-(piperidin-4-ylthio)phenyl)-N-(4-fluorobenzyl)propane sulfonamide,
N-(3-cyano-4-(piperidin-4-ylamino)phenyl)-N-(4-fluorobenzyl) propanesulfonamide,
N-(4-((1-acetylpiperidin-4-yl)oxy)-3-cyanophenyl)-N-(4-fluorobenzyl) propanesulfonamide,
N-(4-((1-acetylpiperidin-4-yl)thio)-3-cyanophenyl)-N-(4-fluorobenzyl) propanesulfonamide,
N-(4-((1-acetylpiperidin-4-yl)amino)-3-cyanophenyl)-N-(4-fluoro benzyl)propanesulfonamide,
N-(4-((1-formylpiperidin-4-yl)oxy)-3-cyanophenyl)-N-(4-fluoro benzyl)propanesulfonamide,
N-(4-((1-formylpiperidin-4-yl)thio)-3-cyanophenyl)-N-(4-fluoro benzyl)propanesulfonamide,
N-(4-((1-formylpiperidin-4-yl)amino)-3-cyanophenyl)-N-(4-fluoro benzyl)propanesulfonamide, and
ethyl 4-(4-(N-benzylpropanesulfonamido)2-cyanophenyl)-3-oxopiperazin-1-formate,
and pharmaceutically acceptable salts or solvates thereof.

3. A method for preparing the N-benzyl-N-arylsulfonamide compound represented by formula (I) among the N-benzyl-N-arylsulfonamide derivative according to claim 1, the ring A being a substituted benzene ring and Z is absent in formula (I), wherein the preparation method comprises the steps of:
condensing 1-halo-2-$R_3$-4-nitrobenzene with a 6-membered nitrogen-containing aliphatic heterocycle (the ring B) under a basic condition, reducing the nitro group to an amino group, subjecting the amino group to reductive amination, sulfonamidation, and deprotection if necessary, to give the target compound;

alternatively, subjecting 1-halo-2-$R_3$-4-nitrobenzene to nitro reduction, reductive amination and sulfonamidation, condensing the resultant intermediate with a 6-membered nitrogen-containing aliphatic heterocycle (the ring B) under a basic condition, and deprotecting the resultant condensate if necessary, to give the target compound, wherein the preparation method is performed according to the following synthesis scheme:

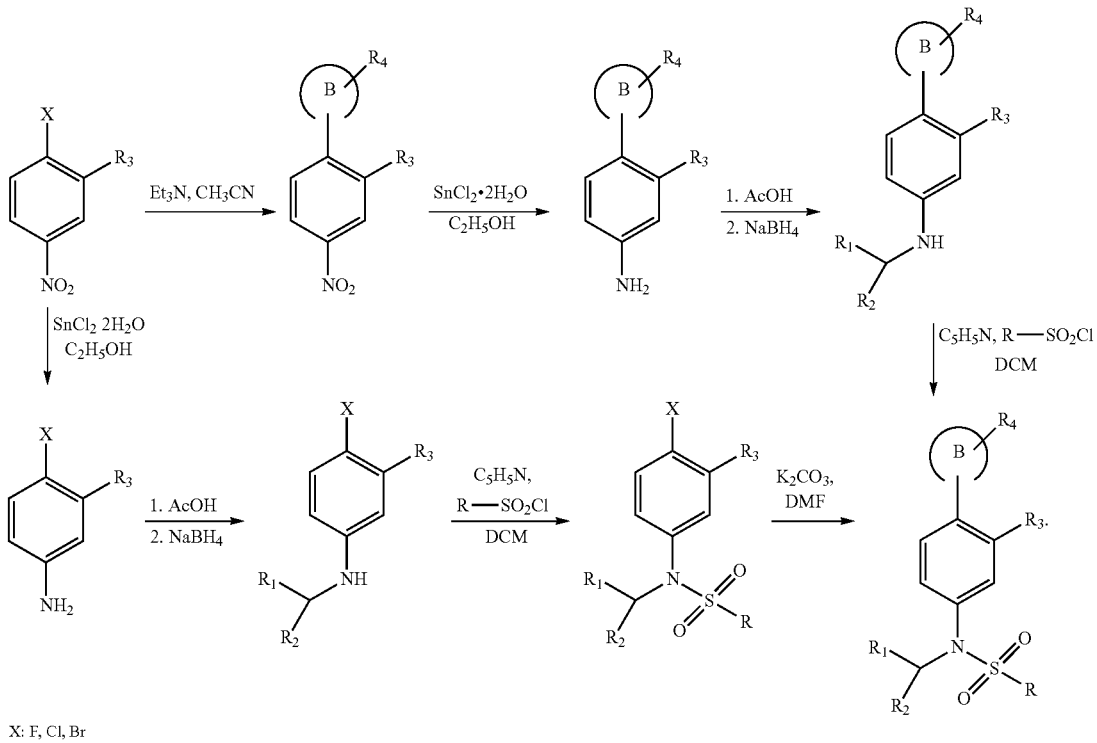

X: F, Cl, Br

4. A method for preparing the N-benzyl-N-arylsulfonamide compound represented by formula (I) among the N-benzyl-N-arylsulfonamide derivative according to claim 1, the ring B is piperidine, and Z is selected from the group consisting of O, S and NH in formula (I), the preparation method is characterized in comprising the steps of:
reacting 1-halo-2-$R_3$-4-nitrobenzene with 4-hydroxy-, 4-mercapto- or 4-amino-piperidine under a basic condition, reducing the nitro group to an amino group, and subjecting the amino group to reductive amination and sulfonamidation, to give the target compound;

alternatively, reacting N-benzyl/alkyl-N-(3-R₃-4-fluro-phenyl)sulfonami de with N-Boc protected 4-hydroxy-, 4-mercapto- or 4-amino-piperidine, removing the Boc protecting group, and substituting at N-position of piperidine, to give the target compound,
the preparation method is performed according to the following synthesis scheme:

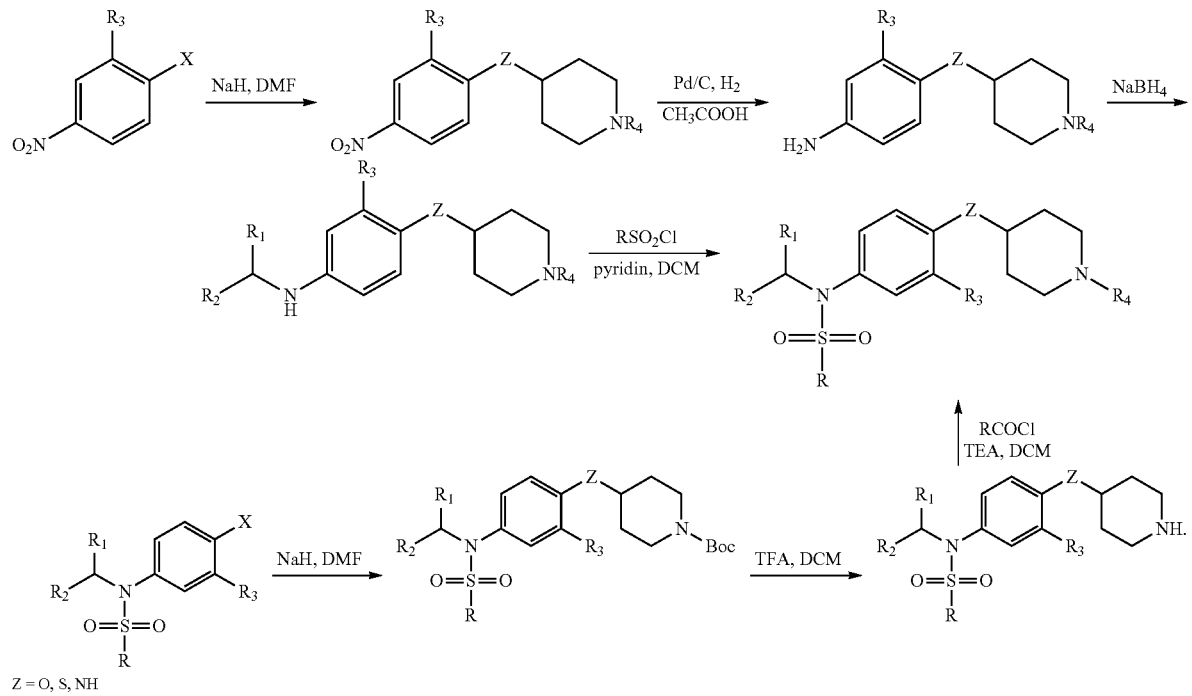

Z = O, S, NH

5. A method of treating autoimmune disease in a subject comprising administering to the subject the N-benzyl-N-arylsulfonamide derivative or a pharmaceutically acceptable salt or solvate thereof according to claim 1 as a selective inhibitor of Kv1.3 potassium channel.

6. The method according to claim 5, characterized in that the N-benzyl-N-arylsulfonamide derivative or the pharmaceutically acceptable salt or solvate thereof is provided in a medicament comprising with at least one pharmaceutically acceptable carrier or excipient.

7. The method according to claim 6, characterized in that the carrier or excipient is any one or more selected from the group consisting of a diluent, filler, adhesive, wetting agent, disintegrating agent, absorption accelerator, surfactant, adsorption carrier, lubricant, flavor agent and sweetener conventionally used in the field of pharmacy.

8. The method according to claim 6, characterized in that the medicament for treating autoimmune diseases is in a dosage form of tablet, capsule, patch, emulsion, suspension, gel, powder, granule, oral liquid or injection.

9. The method according to claim 6, characterized in that the salt of N-benzyl-N-arylsulfonamide compound is an inorganic acid salt or an organic acid salt, the inorganic acid salt is any one or more salts selected from the salts formed with hydrohalogen acid, nitric acid, carbonic acid, sulfuric acid and phosphoric acid, and the organic acid salt is any one or more salts selected from the salts formed with malic acid, L-malic acid, D-malic acid, citric acid, fumaric acid, oxalic acid, lactic acid, camphor sulfonic acid, L-camphor sulfonic acid, D-camphor sulfonic acid, p-toluene sulfonic acid, methane sulfonic acid and benzoic acid.

10. The method according to claim 5, characterized in that the autoimmune disease is psoriasis, psoriatic arthritis, allergic and irritant contact dermatitis, atopic dermatitis, vitiligo, rheumatoid arthritis, type I diabetes, multiple sclerosis, asthma, glomerulonephritis, periodontal disease, pars planitis, graft rejection, neurodegenerative disease, obesity, or hypertension.

11. A medicament for treating autoimmune diseases, characterized in that the medicament comprises the N-benzyl-N-arylsulfonamide derivative according to claim 1 as an active ingredient.

12. The medicament according to claim 11, characterized in that the medicament comprises at least one active component and one or more pharmaceutically acceptable carriers or excipients, and the active component is any one or more of N-benzyl-N-arylsulfonamide compounds represented by formula (I), pharmaceutically acceptable salts or solvate thereof.

13. The medicament according to claim 12, characterized in that the carrier or excipient is any one or more selected from the group consisting of a diluent, filler, adhesive, wetting agent, disintegrating agent, absorption accelerator, surfactant, adsorption carrier, lubricant, flavor agent and sweetener conventionally used in the field of pharmacy.

14. The medicament according to claim 12, characterized in that the medicament is in a dosage form of tablet, capsule, patch, emulsion, suspension, gel, powder, granule, oral liquid or injection.

15. The medicament according to claim 12, characterized in that the salt of N-benzyl-N-arylsulfonamide compound is an inorganic acid salt or an organic acid salt, the inorganic acid salt is any one or more salts selected from the group consisting of the salts formed with hydrohalogen acid, nitric acid, carbonic acid, sulfuric acid and phosphoric acid, and the organic acid salt is any one or more salts selected from the group consisting of the salts formed with malic acid, citric acid, fumaric acid, oxalic acid, lactic acid, camphor sulfonic acid, p-toluene sulfonic acid, methane sulfonic acid and benzoic acid.

16. The medicament according to claim 11, characterized in that the autoimmune disease is psoriasis, psoriatic arthritis, allergic and irritant contact dermatitis, atopic dermatitis, vitiligo, rheumatoid arthritis, type I diabetes, multiple sclerosis, asthma, glomerulonephritis, periodontal disease, pars planitis, graft rejection, neurodegenerative disease, obesity, or hypertension.

* * * * *